US008075484B2

(12) United States Patent (10) Patent No.: US 8,075,484 B2
Moore-Ede (45) Date of Patent: Dec. 13, 2011

(54) SYSTEMS AND METHODS FOR ASSESSING EQUIPMENT OPERATOR FATIGUE AND USING FATIGUE-RISK-INFORMED SAFETY-PERFORMANCE-BASED SYSTEMS AND METHODS TO REPLACE OR SUPPLEMENT PRESCRIPTIVE WORK-REST REGULATIONS

(76) Inventor: Martin Moore-Ede, Wellesley, MA (US)

( * ) Notice: Subject to any disclaimer, the term of this patent is extended or adjusted under 35 U.S.C. 154(b) by 1398 days.

(21) Appl. No.: 11/365,137

(22) Filed: Mar. 1, 2006

(65) Prior Publication Data

US 2006/0200008 A1 Sep. 7, 2006

Related U.S. Application Data

(60) Provisional application No. 60/657,750, filed on Mar. 2, 2005.

(51) Int. Cl.
 *A61B 5/16* (2006.01)
(52) U.S. Cl. .......................... 600/300; 128/898; 128/920
(58) Field of Classification Search .......... 600/300–301; 128/898, 920; 434/262
 See application file for complete search history.

(56) References Cited

U.S. PATENT DOCUMENTS 5,433,223 A * 7/1995 Moore-Ede et al. .......... 128/898
2001/0010028 A1 * 7/2001 Thibault ........................ 701/35

OTHER PUBLICATIONS

Moore-Ede, M. Schlesinger, B. "Scientific Basis for Challenges to Work-Rest & Hours-of-Service Regs," Journal of Transportation Law, Logistics & Policy, Spring 2004, vol. 71, No. 3, pp. 262-279.

Moore-Ede, M. Circadian Technologies, "Fatigue in Transportation Operations," Clinics in Occupational and Environmental Medicine, 2002, pp. 11-27.
Pilcher, J. and Huffcutt, A. "Effects of Sleep Deprivation on Performance: A Meta-Analysis," American Sleep Disorders Association and Sleep Research Society, 1996, pp. 318-326.
Lenne, M. Triggs, T. Redman, J. "Interactive Effects of Sleep Deprivation, Time of Day, and Driving Experience on a Driving Task", Sleep, vol. 1, No. 1998, pp. 38-44.
Borbely, A. and Ackermann, P. "Concepts and Models of Sleep Regulation: An Overview," Journal of Sleep Research, vol. 1, Feb. 25, 1992, pp. 63-79.
Moore-Ede, M. Sulzman, F. Fuller, C. "The Clocks That Time Us: Physiology of the Circadian Timing System," Ch. 3-4, Harvard University Press, 1982.
Moore-Ede, M, "The Twenty Four Hour Society: Understanding Human Limits in a World That Never Stops," Addison-Wesley Publishing Co., 1993.

(Continued)

*Primary Examiner* — Sam Yao
*Assistant Examiner* — Bobby Soriano
(74) *Attorney, Agent, or Firm* — Lathrop & Gage LLP; Steven M. Mills, Esq.

(57) ABSTRACT

In a system and method for assessing and modifying fatigue, an input device receives current work-rest pattern and/or sleep data from an individual. A data aggregation and processing platform combines the current work-rest pattern and/or sleep data with previous data related to the individual to generate a fatigue assessment result, a diagnostic assessment result, and a corrective intervention result. At least one output display outputs the fatigue assessment result, diagnostic assessment result and corrective intervention result in a user-readable format to a user. The user uses this information to revise the work-rest pattern to reduce or control future fatigue risk.

30 Claims, 36 Drawing Sheets

OTHER PUBLICATIONS

Langlois, P. Smolensky, M. Hsi, B. Weir, F. "Temporal Patterns of Reported Single-Vehicle Car and Truck Accidents in Texas, U.S.A. During 1980-1983," Chronobiology International, vol. 2, No. 2, Feb. 1985, pp. 131-146.

Akerstedt, T. "Work Hours, Sleepiness and the Underlying Mechanisms", Journal of Sleep research, vol. 4, Suppl. 2, 1995, pp. 15-22.

Moore-Ede, M. Guttkuhn, R. Heitmann, A. Trutschel, U. "Automatic Detection of Microsleep Events Using a Neural-Fuzzy Hybrid System", Conference on Ocular Measures of Driver Alertness, FHWA-MC-99-136, 1999, pp. 98-107.

Carskadon, M. and Dement, W. "Cumulative Effects of Sleep Restriction on Daytime Sleepiness", Psychophysiology, vol. 18, No. 2, 1981, pp. 107-113.

Van Dongen, H. Maislin, G. Mullington, J. Dinges, D. "The Cumulative Cost of Additional Wakefulness: Dose-Response Effects on Neurobehavioral Functions and Sleep Physiology From Chronic Sleep Restriction and Total Sleep Deprivation," Sleep, vol. 26, No. 2, Jan. 2003, pp. 117-126.

FMCSA-2004-19608, "Proposed Rules: Hours of Service Drivers," Federal Register, vol. 70, No. 14, Jan. 24, 2005, pp. 3344.

Alvarez, A. "The Impact of Daily Sleep Duration on Health: A Review of the Literature," 2004.

Spiegel, K. Leproult, R. Van Cauter, E. "Impact of Sleep Debt on Metabolic and Endocrine Function," Early Report, vol. 354, Oct. 23, 1999, pp. 1435-1439.

Taheri, S. Lin L. Austin, D. Young, T. Mignot, E. "Short Sleep Duration is Associated with Reduced Leptin, Elevated Ghrelin, and Increased Body Mass Index," PLOS Medicine, vol. 1, Issue 3, Dec. 2004, pp. 1-8.

Spiegel, K. Tasali, E. Penev, P. Van Cauter, E. "Brief Communication: Sleep Curtailment in Healthy Young Men Is Associated with Decreased Leptin Levels, Elevated Ghrelin Levels, and Increased Hunger and Appetite," vol. 141, No. 11, Dec. 7, 2004, pp. 847-850.

Horne, J. "Is There a Sleep Debt?" Sleep, vol. 27, No. 6, 2004, pp. 1047-1049.

Mitler, M. Miller, J. Lipsitz, J. Walsh, J. Wylie, D. "The Sleep of Long-Haul Truck Drivers," New England Journal of Medicine, Sep. 1997, vol. 337, No. 11, pp. 755-761.

Kripke DF, Garfinkel L, Wingard DL, Klauber MR, Marler MR, "Mortality Associated with Sleep Duration and Insomnia," Arch. Gen. Psychiatry, vol. 59, No. 2, Feb. 2002.

Ayas, White, Al-Delaimy, Manson, Stampfer, Speizen, Patel, Hu, "A Prospective Study of Self-Reported Sleep Duration and Incident Diabetes in Women," vol. 26, No. 2, 2003, pp. 380-384.

"2002 'Sleep in America' Poll," National Sleep Foundation, Prepared by WB:A Market Research, Mar. 2002.

Czeisler, C. "Rotating Shift Work Schedules That Disrupt Sleep Are Improved by Applying Circadian Principles,"Science, vol. 217, No. 4558, Jul. 30, 1982, pp. 460-463.

Knauth, P. "Speed and Direction of Shift Rotation", vol. 4, Suppl. 2, 1995, pp. 41-46.

Czeisler, C. Weitzman, E. Moore-Ede, M. Zimmerman, J. Knauer, R. "Human Sleep: Its Duration and Organization Depend on Its Circadian Phase," Reprint Seriers, vol. 210, Dec. 12, 1980, pp. 1264-1267.

Dijk, D. Czeisler, C. "Contribution of the Circadian Pacemaker and the Sleep Homeostat to Sleep Propensity, Sleep Structure, Electroencephalographic Slow Waves, and Sleep Spindle Activity in Humans", Journal of Neuroscience, May 1995, 15(5): pp. 3526-3538.

Akerstedt, T. Gillberg, M. "A Dose-Response Study of Sleep Loss and Spontaneous Sleep Termination," Society for Psychophysiological Research, Inc., vol. 23, No. 3, 1986, pp. 293-297.

Carskadon, M. Acebo, C. Jenni, O. "Regulation of Adolescent Sleep: Implications for Behavior. Ann N.Y. Acad. Sci." Sep. 15, 2004, pp. 1-19.

Rosekind, M. "Managing Safety, Alertness and Performance Through Federal Hours of Service Regulations: Opportunities and Challenges," Mar. 2005, pp. 1-35.

Rogers, N. Dorrian, J. Dinges, D. "Sleep, Waking and Neurobehavioural Performance", Frontiers in Bioscience 8, Mar. 2005, pp. 1056-1067.

Moline, M. Pollak, C. Monk, T. Lester, L. Wagner, D. Zendell, S. Graeber, R. Salter, C. Hirsch, E. "Age-Related Differences in Recovery from Simulated Jet Lag," Sleep, 15(1), 1992, pp. 28-40.

Czeisler, C. Kronauer, R. Allan, J. Duffy, J. Jewett, M. Brown, E. Ronda, J. "Bright Light Induction of Strong (Type 0) Resetting of the Human Circadian Pacemaker", Sleep, vol. 244, Jun. 1989, pp. 1328-1333.

Aeschbach, D. Matthews, J. Postolache, T. Sher, L. Giesen, J. Jackson, M. Weir, T. "Differences in the Timing of the Circadian Rhythm of Plasma Cortisol Between Short Sleepers and Long Sleepers," Sleep, vol. 22, 1999, pp. S141-S142.

Duffy, J. Rimmer, D. Silva, E. Czeisler, C. "Correlation of Intrinsic Circadian Period with Morningness-Eveningness in Young Men," Sleep, vol. 22, 1999, p. S92.

Costa, G. Lievore, F. Casaletti, G. Gaffuri, E. "Circadian Characteristics Influencing Interindividual Differences in Tolerance and Adjustment to Shiftwork", Ergonomics, vol. 32, No. 4, 1989, pp. 373-385.

Akerstedt, T. "Psychological and Psychophysiological Effects of Shift Work", Scand J Work Environ Health, vol. 16, Suppl. 1, 1990, pp. 67-73.

Radosevic-Vidacek B, Vidacek S, Kaliterna L, Ravlic M, Lalic V, Prizmic A, "Interindividual Differences in Tolerance to Shift Work and Characteristics of Shift Workers: Relation Between the Quality and Duration of Sleep and Certain Worker Characteristics", Arh Hig Rada Toksikol, 43(3), 1992, p. 227.

Katzenberg, D. Young, T. Finn, L. Lin, L. King, D. Takahashi, J. Mignot, E. "A CLOCK Polymorphism Associated with Human Diurnal Preference," Sleep, vol. 21, No. 6, Jun. 1998, pp. 569-576.

Taillard, Philip, Bioulac, "Morningness/Eveningness and the Need for Sleep", J Sleep Res. 8(4) Dec. 1999, 291-295.

Ishihara, K. Miyasita, A. Inugami, M. Fukuda, K. Miyata, Y. "Differences in Sleep-Wake Habits and EEG Sleep Variables Between Active Morning and Evening Subjects", Sleep, 10(4), 1987, pp. 330-342.

Torsvall, L. Askerstedt, T. "A Diurnal Type Scale: Construction, Consistency and Validation in Shift Work," Scandinavian Journal of Work, Environment & Health 6, 1980, pp. 283-290.

Taillard, J. Philip, P. Chastang, J. Bioulac, B. "Validation of Home and Ostberg Morningness-Eveningness Questionnaire in a Middle-Aged Population of French Workers", Journal of Biological Rhythms, vol. 19, No. 1, Feb. 2004, 76-84.

Roenneberg, T. Kuehnle, T. Pramstaller, P. Ricken, J. Havel, M. Guth, A. Merrow, M. "A Marker for the End of Adolescence", Current Biology, vol. 14, No. 24, R1038-R1039.

Horne, J. Reyner, L. "Counteracting Driver Sleepiness: Effects of Napping, Caffeine, and Placebo," Psychophysiology, Cambridge University Press, 1996, pp. 306-309.

Garbarino, S. Mascialino, B. Penco, M. Squarcia, S. De Carli, F. Nobili, L. Beelke, M. Cuomo, G. Ferrillo, F. "Professional Shift-Work Drivers Who Adopt Prophylactic Naps Can Reduce the Risk of Car Accidents During Night Work," Sleep, vol. 27, No. 7, 2004, pp. 1295-1303.

Rosekind, M. Smith, R. Miller, D. Co, E. Gregory, K. Webbon, L. Gander, P. Lebacqz, J. "Alertness Management: Strategic Naps in Operational Settings," J Sleep Res. vol. 4, Suppl. 2, 1995, pp. 62-66.

Bonnefond, A. Muzet, A. Winter-Dill, A. Bailloeuil, C. Bitouze, F. Bonneau, A. "Innovative Working Schedule: Introducing One Short Nap During the Night Shift," Ergonomics, vol. 44, No. 10, 2001, pp. 937-945.

"Voluntary Fire Protection Requirements for Light Water Reactors; Adoption of NFPA 805 as a Risk-Informed, Performance-Based Alternative", Jul. 2004, downloaded from http://www.epa.gov/fedrgstr/EPA-IMPACT/2002/November/Day-011/i27701.htm on Aug. 10, 2007.

Mackin, P. Russell, B. Turner, D. "Implementing Risk-Informed, Performance-Based Regulations for High-Level Waste Disposal," WM'01 Conference, Feb. 25-Mar. 1, 2001, Tuscson, AZ, pp. 1-6.

National Research Council (U.S.), "ISC Security Design Criteria for New Federal Office Buildings and Major Modernization Projects: A Review and Commentary," 2003, pp. 1-3.

U.S. Census Bureau, 2002 Economic Census, www.census.gov/prod/ec02/ec02tv-us.pdf, "Trucks, Truck Miles, And Average Annual Miles for All Trucks: 2002 and 1997," 2002.

Hartley, L. Arnold, P. Penna, F. Hochstadt, D. Corry, A. Feyer, A. "Fatigue in the Western Australian Transport Industry. Part Two: The Drivers' Perspective," Institute for Research in Safety & Transport, 1996, pp. 1-70.

Kerin, A. "Overtime in Extended Hours Operations: Benefits, Costs, Risks and Liabilities," Circadian Technologies, Inc. Report, 2002 pp. 1-2.

Kerin, A. Carbone, J. "Financial Opportunities in Extended Hours Operations: Managing Costs, Risks, and Liabilites," Circadian Technologies, Inc. Report, 2003, pp. 1-2.

Aguirre, A. Kerin, A. "Shiftwork Practices 2005," Lexington, MA, Circadian Technologies, Inc., pp. 1-2.

Landrigan, C. Rothschild, J. Cronin, J. Kaushal, R. Burdick, E. Katz, J. Lilly, C. Stone, P. Lockley, S. Bates, D. Czeisler, C. "Effect of Reducing Interns' Work Hours on Serious Medical Errors in Intensive Care Units," New England Journal of Medicine, Oct. 2004, pp. 1838-1848.

Lockley, S. Cronin, J. Evans, E. Cade, B. Lee, C. Landrigan, C. Rothschild, J. Katz, J. Lilly, C. Stone, P. Aeschbach, D. Czeisler, C. "Effect of Reducing Interns' Weekly Work Hours on Sleep and Attentional Failures," The New England Journal of Medicine, Oct. 2004,pp. 1829-1837.

Lusa, S. Hakkanen, M. Luukkonen, R. Viikari-Juntura, E. "Work & Stress," Taylor and Francis, vol. 16, No. 3, Jul. 2002, pp. 264-267.

Hartley, L. "Australian Initiatives in Managing Fatigue in Transportation," Insurance Commission of Western Australia Conference on Road Safety. Feb. 2005, pp. 1-19.

The Parliament of the Commonwealth of Australia, "Beyond the Midnight Oil: Managing Fatigue in Transport," 8,32,33,69,78,92.94 House of Representatives Standing Committee on Communications, Transport and the Arts, Oct. 2000, pp. xxxiii-93.

Moore-Ede, M. Czeisler, C. "Mathematical Models of the Circadian Sleep-Wake Cycle," Raven Press, 1984, preface, p. 1.

Moore-Ede, M. Heitmann, A. Guttkuhn, R. Trutschel, U. Aguirre, A. Croke, D. "Circadian Alertness Simulator for Fatigue Risk Assessment in Transportation: Application to Reduce Frequency and Severity of Truck Accidents," Aviation, Space, and Environment Medicine, vol. 75, No. 3, Sec. 2, Mar. 2004, pp. A107-A118.

Borbely, "A Two Process Model of Sleep Regulation," Hum Neurobiol, 1(3), 1982, p. 1: 195-204.

Daan, Beersma, Borbely, "Timing of Human Sleep: Recovery Process Gated By a Circadian Pacemaker," Am J Physiol, 264(2 Pt 2), 1984, ; 246: R161-R183.

Carskadon, M. Dement, W. "Daytime Sleepiness: Quantification of a Behavioral State," Neuroscience & Biobehavioral Reviews, vol. 11, Feb. 1987, vol. 11: pp. 307-317.

Moore-Ede, M. Heitmann, A. Dawson, T. Guttkuhn, R. "Truckload Driver Accident, Injury and Turnover Rates Reduced By Fatigue Risk-Informed Performance-Based Safety Program," 2005, pp. 1-13.

Akerstedt, T. Folkard, S. Portin, C. "Predictions from the Three-Process Model of Alertness", Aviation, Space, and Environmental Medicine, vol. 75, No. 3, Sec. II, Mar. 2004, pp. A75-A83.

Hursh, S. Redmond, D. Johnson, M. Thorne, E. Belenky, G. Balkin, T. Storm, W. Miller, J. Eddy, D. "Fatigue Models for Applied Research in Warfighting," Aviation, Space, and Environmental Medicine, vol. 75, No. 3, Sec, II, Mar. 2004, pp. A44-A53.

Roach, G. Fletcher, A. Dawson, D. "A Model to Predict Work-Related Fatigue Based on Hours of Work," Aviation, Space, and Environmental Medicine, vol. 75, No. 3, Sec. II, Mar. 2004, pp. A61-A69.

Federal Register, "Rules and Regulations", vol. 69, No. 115, Jun. 16, 2004, p. 33536.

Moore-Ede, M. "Requirment for Flexible Sleep Management Rules for Non-Scheduled Irregular-Route Truckload Drivers," Circadian Information Limited Partnership, Mar. 10, 2005, pp. 1-85.

Dawson, D. Reid, K "Fatigue, Alcohol and Performance Impairment," Nature, vol. 388, Jul. 17, 1997, pp. 235.

Arnedt, Wilde, Munt, Maclean, "Simulated Driving Performance Following Prolonged Wakefulness and Alcohol Consumption: Separate and Combined Contributions to Impairment," Journal of Sleep Research, Sep. 2000, vol. 9, No. 3, pp. 233-241(9) (Abstract).

Arnedt, Wilde, Munt, Maclean, "Simulated Driving Performance Following Prolonged Wakefulness and Alcohol Consumption: Separate and Combined Contributions to Impairment," Journal of Sleep Research, Sep. 2000, vol. 9, No. 3, pp. 233-241(9).

Maislin G, Rogers N, Price N, Mullington J, Szuba M, Dinges D. "Response surface modeling of the effects of chronic sleep deprivation with and without diurnal naps," Sleep 2001; 24 (Abstract Supplement):A242.

Hammer M, Champy J. "Re-engineering the corporation: a manifesto for business revolution," Harper Business; 1993.

Rummler G, Brache A. "Improving performance: How to manage the white space on the organization chart," Jossey-Bass Publishers; 1990.

Herzberg GF, Mausner B, Snydeman BB. "The Motivation to Work," New York: Wiley; 1959.

Nuclear Energy Institute. "Nuclear Power Plant Regulation. Executive Summary: Significant Progress Toward a More Objective, Safety-Focused Process," Oct. 2001.

U.S. Census Bureau, 2002 Economic Census, Vehicle Inventory and Use Survey, Issued Dec. 2004.

Lusa, Hakkanen, Luukkonen, and Vikari-Juntura, "Perceived Physical Work Capacity, Stress, Sleep Disturbance and Occupational Accidents Among Firefighters Working During a Strike," Work & Stress, 2002, vol. 16, No. 3, pp. 264-274.

* cited by examiner

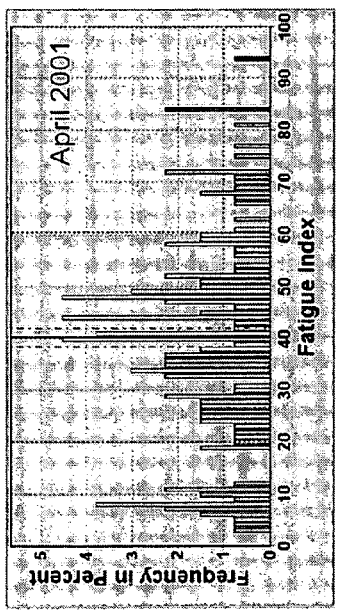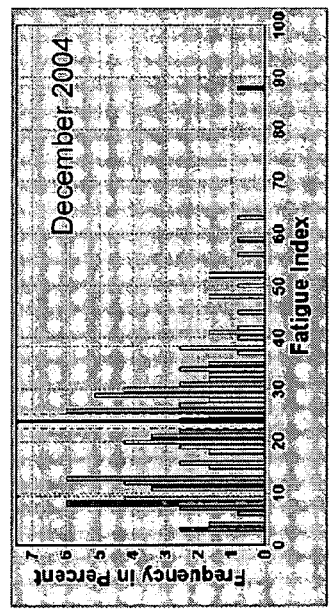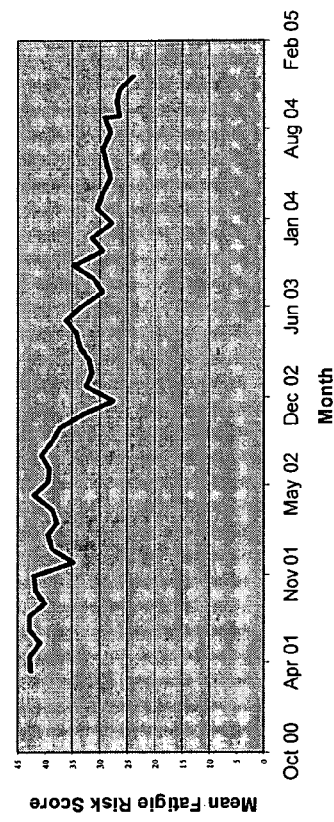
FIG. 12A
FIG. 12B
FIG. 12C

High fatigue risk intervention plan

Recommended actions for Driver #4572
Date: Feb 23 2006 17:02 hr

- Fatigue risk 76.2
- Prior 3 days – 63,69,73
- Fatigue risk high
- Fatigue risk climbing

DIAGNOSTIC FLAGS

Night operations
Near 14-hour duty limit
Rest periods fragmented
Short rest
Short weekly break
Irregular start times

IMMEDIATE ACTIONS

Take 3 hr naps 12M-6A
Reduce duty to 12-hours
Consolidate sleep
10+ hours rest required
Take two day break
Stabilize start times

FIG 33

SYSTEMS AND METHODS FOR ASSESSING EQUIPMENT OPERATOR FATIGUE AND USING FATIGUE-RISK-INFORMED SAFETY-PERFORMANCE-BASED SYSTEMS AND METHODS TO REPLACE OR SUPPLEMENT PRESCRIPTIVE WORK-REST REGULATIONS

RELATED APPLICATIONS

This application is based on U.S. Provisional Patent Application No. 60/657,750 filed on Mar. 2, 2005.

BACKGROUND OF THE INVENTION

Many occupations require workers to be on duty around-the-clock for extended periods of time, and to work irregular shifts while on duty. However, night work and/or irregularly scheduled shifts can lead to worker fatigue, which is defined here as reduced alertness, increased sleepiness, impaired performance or unsafe behavior occurring as a result of excessive work hours, inadequate rest, sleep deprivation or circadian time-of-day factors. In addition, workers often suffer acute or chronic sleep deprivation, in combination with circadian time-of-day factors, which can exacerbate fatigue. Worker fatigue is particularly problematic among transportation employees including commercial motor vehicle (CMV) operators, for example, truck drivers, wherein driver fatigue can increase the risk of an accident.

Many governments recognize this issue, and have implemented prescriptive rule-based regulations in an effort to reduce the number of accidents caused by worker fatigue. For example, in the United States, the Federal Motor Carrier Safety Administration (FMCSA), to reduce the number and severity of commercial motor vehicle (CMV) crashes and enhance the safety of CMV operations, has implemented Hours of Service (HoS) regulations which place maximum limits on the number of hours of work, and minimum limits on the hours of rest. HoS regulations are widely adopted in all transportation modes including the regulation of commercial motor vehicles. However, prescriptive HoS regulations do not distinguish between off-duty time and actual sleep time. Instead, contrary to its intended purpose, HoS regulations often require CMV operators to operate their vehicles when they are fatigued, and to stop driving at times when they are not tired and cannot sleep. This can lead to drivers falsifying their driver logs so that they can sleep when they are tired, and drive when they are alert. While advances in circadian, sleep and alertness physiology, and the technology and operations of modern transportation address have been used to attempt to address shortcomings of prescriptive HoS regulations, the interaction of circadian sleep science and modern operational practices is highly complex, and it is impractical to adequately overcome such shortcomings by incorporating operational practices based on circadian sleep science into current prescriptive HoS regulations.

SUMMARY OF THE INVENTION

To address the above limitations, a first feature of the present invention is to provide a fatigue risk assessment system and a fatigue risk modification system. A second feature of the present invention is to provide a method for assessing fatigue and distributing a fatigue assessment result, and using this result to minimize the risk of fatigue and improve equipment operator performance and safety. Together these provide a Fatigue-Risk-Informed Safety-Performance-Based (FRISPB) system and method.

In accordance with a first aspect of the invention, there is provided a fatigue risk assessment and modification system, comprising an input device, a data aggregation and processing platform, at least one output display, and a system for modifying future fatigue risk. The input device receives current work-rest pattern and/or sleep data from an individual. If sleep data is not available directly from an input device, the current work-rest pattern data can be converted into a predicted sleep-wake pattern using a sleep-prediction algorithm. The data aggregation and processing platform combines the current work-rest pattern and/or predicted sleep-wake pattern and/or directly recorded sleep data with previous data related to the individual to generate at least one of a fatigue assessment result, a diagnostic assessment report that includes a causation of excessive fatigue risk, and a corrective intervention plan for reducing future fatigue risk. The at least one output display outputs the at least one of the fatigue assessment result, the diagnostic assessment report, and the corrective intervention plan in a user-readable format to a user. The user is provided with diagnostic tools and instructions to modify future fatigue risk, the success of which is assessed using the fatigue risk assessment system.

Sleep data may comprise data collected by any of the available methods for measuring sleep including but not limited to electro-encephalographic, electro-occulographic, or myographic recordings, activity movements such as wrist activity devices, or bed or sleeping area sensors, such as pressure or motion sensors. Sleep data can also include data obtained from any device which measures the sleepiness or alertness of an individual including but not limited to that of the type described in, for example, U.S. Pat. No. 6,511,424, issued Jan. 28, 2003, entitled "Method of and Apparatus for Evaluation and Mitigation of Microsleep Events," and incorporated herein in its entirety by reference. Alternatively, the sleep data collection device can be a proprietary device that is privately developed for exclusive personal use, or may be a sleep data collection device that is in the public domain or a sleep data collection device used in research in academic institutions.

In an embodiment, the input device generates a current record from the current work-rest pattern and/or sleep data related to the individual, and wherein the data aggregation and processing platform stores the current record.

In an embodiment, a plurality of input devices receives current work-rest pattern and/or sleep data from a plurality of individuals. The data aggregation and processing platform receives the current work-rest pattern and/or sleep data from each input device and generates at least one of a fatigue assessment result, a diagnostic assessment report that includes a causation of excessive fatigue risk, and a corrective intervention plan for reducing future fatigue risk for each individual.

In an embodiment, the individual enters data into a device to provide a record of duty and non-duty activities and times of rest to provide the current work-rest pattern and/or sleep data. The input device and the individual data entry device can be the same.

In an embodiment, a position verification device verifies the current work-rest pattern and/or sleep data. The input device and the position verification device can be the same.

In an embodiment, an engine control module (ECM) records engine operations and/or movements and/or operator-originated modifications to engine operations to verify the current work-rest pattern and/or sleep data. In an embodiment, the engine control module collects data on movements of a machine that is operated by the individual and verifies the at least one of the current work-rest pattern and the sleep data by determining whether the machine has moved. The input device and the engine control module device can be the same.

In an embodiment, the current work-rest pattern and/or sleep data is collected from worker logs and manually entered into the input device. The current work-rest pattern and/or sleep data can be collected from electronic logs and electronically entered into the input device.

The current work-rest pattern and/or sleep data is transmitted from the input device to the data aggregation and processing platform through a communications network, the communications network being one of a satellite communications network, a wireless network, a telecommunications network, and a data communications network.

In an embodiment, the data aggregation and processing platform comprises a fatigue risk processor that computes the at least one of the fatigue assessment result, the diagnostic assessment report, and the corrective intervention plan from the current work-rest pattern and/or sleep data. At least one predictive model is applied to the fatigue risk processor to compute the at least one of the fatigue assessment result, the diagnostic assessment report, and the corrective intervention plan.

In an embodiment, the data aggregation and processing platform comprises a fatigue risk processor that computes the fatigue assessment result, the diagnostic assessment result, and the corrective intervention result from the current work-rest pattern and/or sleep data. At least one predictive model is applied to the fatigue risk processor to compute the fatigue assessment result, the diagnostic assessment result, and the corrective intervention result.

The predictive model can be at least one fatigue risk model. The fatigue risk model computes the fatigue assessment result as a fatigue risk score. The predictive model complies with a Fatigue-Risk-Informed Safety-Performance-Based (FRISPB) paradigm. The driver fatigue risk assessment can be output to the output display.

In an embodiment a driver profile model computes a driver profile result utilizing driver personality assessments, driver employment records, driver health and driver motor vehicle records and other individual driver-specific non-fatigue data. The fatigue risk score and the driver profile result are combined to generate a driver risk assessment. The driver risk assessment is output to the output display.

In an embodiment, the user uses the fatigue assessment result to control fatigue risk in the individual using a diagnostic assessment report on the causation of excessive fatigue risk, and a corrective intervention plan to reduce future fatigue risk.

In an embodiment, the user is provide with diagnostic tools and instructions to modify the future fatigue risk of each individual which are provided as the diagnostic assessment result, and the corrective intervention result In an embodiment, the individual is a commercial motor vehicle driver, and the fatigue risk assessment system is installed in a machine in a vehicle that is operated by the driver. In another embodiment, the individual is a machine operator, and the fatigue risk assessment system is installed in a machine that is operated by the machine operator.

In an embodiment, the input device and the output display are the same.

In accordance with another aspect of the invention, there is provided a method for assessing fatigue and distributing a fatigue assessment result, a diagnostic assessment result and a corrective intervention result. A current work-rest pattern and/or sleep data is received from an individual. The current work-rest pattern and/or sleep data is combined with previous data related to the individual. A fatigue assessment result, the diagnostic assessment result on the causation of any excessive fatigue risk, and the corrective intervention result for reducing fatigue risk are generated from the combination of the current record and previous data related to the individual. The fatigue assessment result, the diagnostic assessment result, and the corrective intervention result are outputted in a user-readable format to a user.

In an embodiment, a current record is generated from the current work-rest pattern and/or sleep data related to the individual, and the current record is stored.

In an embodiment, the current work-rest pattern and/or sleep data is received from a group of individuals, and the fatigue assessment result, the diagnostic assessment result, and the corrective intervention result are generated for each individual.

In an embodiment, the current work-rest pattern and/or sleep data is verified.

The current work-rest pattern and/or sleep data is transmitted through a communications network, the communications network being one of a satellite communications network, a wireless network, a telecommunications network, and a data communications network.

At least one predictive model is applied to compute the fatigue assessment result, the diagnostic assessment report, and the corrective intervention plan. The predictive model complies with a Fatigue-Risk-Informed Safety-Performance-Based (FRISPB) paradigm. The fatigue assessment result is computed as at least one of a fatigue risk score and a non-fatigue factor assessment result is computed as a driver profile result. A driver risk assessment is generated from a combination of the fatigue risk score and the driver profile result.

In an embodiment, the fatigue assessment result is used to control fatigue risk in the individual. In another embodiment, the at least one of the fatigue assessment result, the diagnostic assessment report, and the corrective intervention plan are combined to reduce future fatigue risk.

In one embodiment, the individual is a machine operator. In another embodiment, the individual is a driver.

In accordance with another aspect of the invention, there is provided a method for assessing operator fatigue. Work-rest pattern and/or sleep data is collected or computed from work-rest patterns from at least one operator. The work-rest pattern and/or sleep data is validated. The validated work-rest pattern and/or sleep status data is combined with previously collected work-rest pattern and/or sleep data in a data aggregation and processing platform. At least one of a fatigue assessment result, a diagnostic assessment result and a corrective intervention result are generated from the validated work-rest pattern and/or sleep status data and previously collected work-rest pattern and/or sleep data. The fatigue assessment result, the diagnostic assessment result, and the corrective intervention result are displayed in a user-readable format.

In an embodiment, the work-rest pattern and/or sleep data is validated by locating a commercial vehicle that is operated by the operator. In another embodiment, the work-rest pattern and/or sleep data is validated by locating a machine that is operated by the operator. The at least one of the work-rest pattern and the sleep status data is validated by locating a machine that is operated by the operator at intervals of time to compare a first location and a second location of the machine to determine a movement of the machine.

At least one predictive model is applied to compute the at least one of the fatigue assessment result, the diagnostic assessment result, and the corrective intervention result. The predictive model complies with a Fatigue-Risk-Informed Safety-Performance-Based (FRISPB) paradigm.

In an embodiment, the fatigue assessment result is computed as a fatigue risk score. In another embodiment, the fatigue assessment result is computed as an alertness score. In another embodiment, the fatigue assessment result is computed as sleepiness or drowsiness score. In another embodiment, the fatigue assessment result is computed as an operator performance score. In another embodiment, the fatigue assessment result is computed as an accident risk score. In another embodiment, the fatigue assessment result is computed as an injury risk score. In another embodiment, the fatigue assessment result is computed as an operator profile result. In another embodiment, a non-fatigue factor assessment result is computed as an operator profile result. In another embodiment an operator risk assessment is computed from a combination of the fatigue risk score and the operator profile result. In an embodiment, the fatigue assessment result, the diagnostic assessment result, and the corrective intervention result is used to control fatigue risk in the operator. In an embodiment, a combination of the at least one of the fatigue assessment result, the diagnostic assessment result, and the corrective intervention result are used to reduce fatigue risk in the operator.

In accordance with another aspect of the invention, there is provided a fatigue risk assessment system for assessing fatigue in a truck driver. An input device receives current work-rest pattern and/or sleep data from the truck driver. A data aggregation and processing platform combines the current work-rest pattern and/or sleep data with previous data related to the truck driver to generate at least one of a fatigue assessment result, a diagnostic assessment result and a corrective intervention result. At least one output display outputs the fatigue assessment result, the diagnostic assessment result, and the corrective intervention result in a user-readable format to a user.

In an embodiment, a plurality of input devices receives current work-rest pattern and/or sleep data from group of truck drivers. The data aggregation and processing platform receives the current work-rest pattern and/or sleep data from each input device and generates a fatigue assessment result, the diagnostic assessment result, and the corrective intervention result for each truck driver.

In an embodiment, a position verification device verifies the current work-rest pattern and/or sleep data.

The current work-rest pattern and/or sleep data is transmitted from the input device to the data aggregation and processing platform through a communications network.

The data aggregation and processing platform comprises a fatigue risk processor that computes the fatigue assessment result, the diagnostic assessment result, and the corrective intervention result from the current work-rest pattern and/or sleep data. At least one predictive model is applied to the fatigue risk processor to compute the fatigue assessment result, the diagnostic assessment result, and the corrective intervention result from the current work-rest pattern and the sleep data. The fatigue risk model computes the fatigue assessment result as a fatigue risk score, the diagnostic assessment report, and the corrective intervention plan, and a driver profile model computes a driver profile result that includes other non-fatigue causes of risk. The predictive model complies with a Fatigue-Risk-Informed Performance-Based (FRISPB) paradigm. The fatigue risk assessment is output to the output display.

In an embodiment a driver profile model computes a driver profile result utilizing driver personality assessments, driver employment records, driver health and driver motor vehicle records and other individual driver-specific data. The fatigue risk score and the driver profile result are combined to generate a driver risk assessment. The driver risk assessment is output to the output display.

In an embodiment, the fatigue risk assessment system is installed in a commercial motor vehicle that is operated by the truck driver.

In accordance with another aspect of the invention, there is provided a method for assessing truck driver fatigue. Work-rest pattern and/or sleep data is collected or computed from work-rest patterns from at least one truck driver. A commercial motor vehicle operated by the truck driver is located. A location of the commercial motor vehicle is relocated after a time interval and determined if the vehicle has moved. The location of the commercial motor vehicle is validated. The work-rest and/or sleep data is updated to include validated location data of the commercial motor vehicle. The updated work-sleep status data is combined with previously collected work-rest and/or sleep data in a data aggregation and processing platform. At least one of a fatigue assessment result, a diagnostic assessment report, and a corrective intervention plan is generated from the validated work-rest and/or sleep data and the previously collected or computed sleep data. The fatigue assessment result, diagnostic assessment report, and corrective intervention plan are displayed in a user-readable format.

In an embodiment, at least one predictive model is applied to compute the fatigue assessment result, diagnostic assessment report, and corrective intervention plan. The predictive model complies with a Fatigue-Risk-Informed Performance-Based (FRISPB) paradigm.

In an embodiment, at least one of the fatigue assessment result as a truck driver fatigue risk score, the diagnostic assessment result, and the corrective intervention plan is computed, and a truck driver profile result that includes other non-fatigue causes of risk is computed. A truck driver risk assessment is generated from a combination of the truck driver fatigue risk score and the truck driver profile result. The truck driver fatigue assessment result, diagnostic assessment report, and corrective intervention plan are used to control fatigue risk in the truck driver.

BRIEF DESCRIPTION OF THE DRAWINGS

The foregoing and other objects, features, and advantages of the invention will be apparent from the more particular description of preferred aspects of the invention, as illustrated in the accompanying drawings in which like reference characters refer to the same parts throughout the different views. The drawings are not necessarily to scale, emphasis instead being placed upon illustrating the principles of the invention.

FIGS. 12A and 12B contain graphs illustrating a fatigue risk score distribution before and after implementing an FRISPB paradigm, respectively, according to an embodiment of the present invention.

FIG. 12C contains a graph illustrating a mean fatigue risk score generated each month of an implemented FRISPB program, according to an embodiment of the present invention.

FIG. 33 contains an output comprising a diagnostic assessment and a corrective report including supervisory corrective interventions, according to an embodiment of the present invention.

DETAILED DESCRIPTION OF PREFERRED EMBODIMENTS OF THE INVENTION

Figure 1:
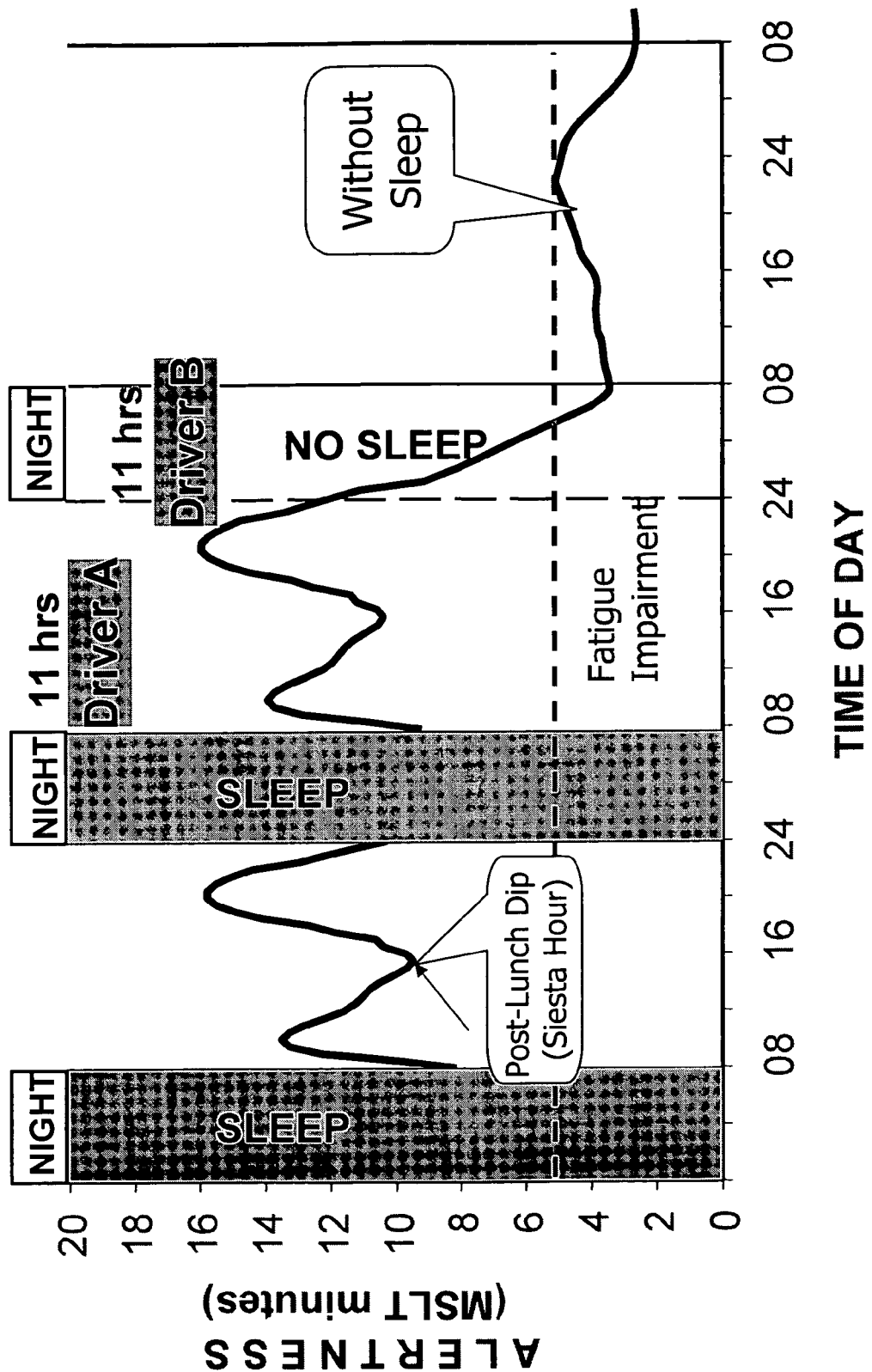
FIG. 1 contains a graph illustrating variations in alertness levels of two truck drivers both operating legally under current FMCSA HoS regulations but with different levels of fatigue risk during different time periods of a work shift according to laws of circadian sleep physiology.

To provide an overall understanding, certain illustrative embodiments will now be described and are attached herein as supplemental sheets; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless specified, can be altered without affecting the scope of the disclosed and exemplary systems or methods of the present disclosure.

The methods and systems described herein are not limited to a particular hardware of software configuration, and may find applicability in many computing or processing environments. The methods and systems can be implemented in hardware or software, or a combination of hardware and software. The methods and systems can be implemented in one of more computer programs, where a computer program can be understood in include one of more computer programs, where a computer program can be understood to include one or more processor executable instructions. The computer program(s) can execute on one of more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one of more high level procedural or object-oriented programming languages to communicate with a computer system; however, the program(s) can be implemented in assembly or machine language, if desired. The language can be compiled or interpreted.

As provided herein, the processor(s) can thus be embedded in one or more devices that can be operated independently or together in a networked environment, where the network can include, for example, a Local Area Network (LAN), a wide area network (WAN), and/or can include an intranet and/or the internet and/or another network. The networks(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer(s), workstation (e.g. Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus can be configured to communicate via wired or wireless communications with other processors, where such one or more processor can be configured to operate on one or more processor-controlled devices that can be similar or different devices. Use of such "microprocessor" or "processor" terminology can thus also be understood to include a central processing unit, an arithmetic logic unit, an application-specific integrated circuit (IC), and/or a task engine, with such examples provided for illustration and not limitation.

Furthermore, references to memory, unless otherwise specified, can include one or more processor-readable and accessible memory elements and/or components that can be internal to the processor-controlled device, external to the processor-controlled device, and/or can be accessed via a wired or wireless network sing a variety of communications protocols, and unless otherwise specified, can be arranged to include a combination or external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, tress, with such structures provided for illustration and not limitation.

References to a network, unless provided otherwise, can include one or more intranets and/or the internet. References herein to microprocessor instructions or microprocessor-executable instructions, in accordance with the above, can be understood to include programmable hardware.

Unless otherwise stated, use of the word "substantially" can be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun can be understood to be used for convenience and to include one, or more than one of the modified noun, unless otherwise specifically stated.

Elements, components, modules, and/or parts thereof that are described and/or otherwise portrayed through the figures to communicate with, be associated with and/or be based on, something else, can be understood to so communicate, be associated with, and/or be based on in a direct and/or indirect manner, unless otherwise stipulated herein.

Although the methods and systems have been described relative to a specific embodiment thereof, they are not so limited. Many additional changes in the details, materials, and arrangement of parts, herein described and illustrated, can be made by those skilled in the art. Obviously man modifications can variations may become apparent in light of the above teachings and the following.

To address the above limitations, the present invention provides a system and method for assessing fatigue and improving safety results over existing prescriptive safety regulations. The fatigue risk assessment systems and methods of the present invention conform to a Fatigue-Risk-Informed Safety-Performance-Based (FRISPB) paradigm, which applies one or more risk models to measure actual fatigue risk and to obtain better safety results. Compared to current prescriptive HoS regulations, the FRISPB paradigm is more firmly based on physiological science and transportation research. In one embodiment, the present invention applies the FRISPB paradigm to fatigue risk, and therefore, the present invention can incorporate one or more risk models to provide risk-informed information to transportation operation employees and managers, and to enable performance-based objectives to be established and progress against these objectives to be evaluated.

The present invention can therefore be applied to any industry having workers engaged in activities in which fatigue assessment is valuable. Examples include, but are not limited to, regulated industries such as the trucking industry, railroad industry, aviation industry, maritime industry, nuclear power generation industry, mining industry, petrochemical industry, manufacturing industry, and military and other governmental operations.

The risk model can be of the type described in, for example, U.S. Pat. No. 5,433,223, issued Jul. 18, 1995, entitled "Method for Predicting Alertness and Bio-Compatibility of Work Schedule of an Individual," and incorporated herein in its entirety by reference. Alternatively, the risk model can be a proprietary risk model that is privately developed for exclusive personal use, or may be a risk model that is in the public domain or a risk model used in research in academic institutions.

The risk model referenced above can be implemented as a commercially available expert system, for example, the Circadian Alertness Simulator (CAS), and, in one embodiment, can be applied by the present invention to measure the risk of accidents caused by sleep deprivation in commercial truck drivers. The CAS includes a software-based expert system that offers a tool for managing a set of flexible sleep management rules for safe operation of trucking fleets. The flexible rules provide a viable alternative to the traditional HoS regulatory paradigm.

In this manner, the present invention generates fatigue assessment results based on model rules. In one embodiment, the fatigue assessment results are fatigue risk scores that are generated by the CAS. The fatigue assessment results are received by individuals, for example workers, or managers, law enforcement, or monitoring centers, wherein work-rest patterns of the individual can be adjusted accordingly in response to the fatigue assessment result. In addition, performance-based objectives can be established in response to the fatigue assessment results. The above-mentioned individuals can be commercial motor vehicle (CMV) operators or machine operators, for example, a truck driver, bus driver, airline pilot or navigator, or boat operator, or any driver or machine operator who poses a safety risk as a result of being deprived of sleep while operating a machine or commercial motor vehicle (CMV) such as a truck, bus, or a transportation vehicle such as a train, or other mode of transportation such as an airplane or boat. In other embodiments, the individual can be an employee who performs a function, wherein a risk of fatigue can affect the employee's ability to effectively perform the function.

The fatigue assessment results are generated in response to current work-rest pattern and/or sleep data of the driver, as well as from aggregated, previously collected work-rest pattern and/or sleep data of the driver. As a result, the driver can adjust his work-rest schedule so as to get restorative rest, and thereby reduce the risk of a fatigue-related accident.

The data can be verified using vehicle positioning, telematics and other data capture systems including engine control modules (ECM) installed in the vehicle. The telematics and data capture systems can objectively confirm non-driving times and duty times. For example, if the vehicle positioning device in the vehicle captures data showing that the vehicle has moved position, or the ECM shows that the vehicle has traveled at a non-zero velocity, during a sleep period reported or logged by the driver of a solo-operated vehicle then the telematics system will transmit data which indicates that the claimed sleep period is not verified. The present invention, for example, applying the CAS system, assesses the sleep deprivation fatigue risk for each driver over a prescribed period based on the work-rest schedule provided by the telematics and data capture system over the prescribed period. Fatigue assessment results, for example, sleep deprivation fatigue risk scores generated by the CAS, may be provided to the drivers, managers, dispatchers, and others having responsibility for safe driving operations, so that they are risk-informed. In addition, training can be provided to employees and managers on how to interpret the fatigue risk scores, how to adjust work-rest schedules to minimize risk, and other related alertness management techniques. Performance-based incentives can be provided to evaluate, on an on-going basis, success at minimizing fatigue risk scores.

For those transport operations using the above operating methods and systems, observable safety improvements may provide the basis for regulatory agencies to allow the adoption of flexible sleep management rules in lieu of traditional prescriptive rules.

The abovementioned prescriptive HoS regulations present a dilemma for the FMCSA and other transportation agencies. Current HoS regulations are based on a concept that was originally developed in the early 1900s, which regulates the "hours of duty," "hours of driving," and "hours of rest" of a CMV operator without considering the amount of actual sleep that is required to reduce fatigue in the CMV operator while driving a vehicle. In addition, advances in circadian, sleep and alertness physiology, and the technology and operations of modern transportation have rendered HoS regulations obsolete. Moreover, the interaction of circadian sleep science and modern operational practices is complex and therefore difficult to integrate into HoS prescriptive rules, that could be readily understood by drivers, managers, and law enforcement officers, and are thereby enforceable.

Recent revisions to the HoS regulations were implemented on Jan. 4, 2004, which addressed several issues with previous HoS regulations. In particular, the 2004 revisions introduced two additional hours of off-duty time per day, and restricted the length of on-duty and waiting time. Further revisions to the HoS regulations were implemented in response to legal challenges by interest groups on Oct. $1^{st}$ 2005 which further restricted driver flexibility in obtaining sleep by defining more restrictively the "split-sleeper" regulations which define how the required 10 hours of rest during each 24 hour period can be divided into separate split-sleep periods.

While the 2004 and 2005 revisions were intended to assist truck drivers obtain the sleep they need for safe driving and good health, many truck drivers find they have the opposite effect and make sleep more difficult to obtain if they comply with the new strict prescriptive HoS rules. For example, one group of truck drivers, categorized as non-scheduled irregular-route (NSIR) truckload drivers, fails to benefit from the HoS regulations. Over 340,000 NSIR truckload drivers are currently employed in the U.S., and perform several operations, including transporting truckloads of goods directly from shipping dock to receiving dock, while providing a critical flexibility and cost-efficiency to the economy and business supply chains that cannot be met by railroads, aviation, or less-than-truckload (LTL) carriers operating from fixed terminals. NSIR drivers often work from home for more than 7 days at a time, and sometimes for several weeks at a time. During extended trips, NSIR drivers usually sleep in a well-equipped truck "motor home" sleeper berth.

The essential basis of current prescriptive HoS regulations is the now-outdated concept that fatigue can be prevented using work-rest rules based on the concept that increased consecutive hours of work result in an increased risk of fatigue, and increased consecutive hours of rest reduces fatigue risk. However, this concept assumes that the increased rest time includes increased sleep time. As a result, NSIR drivers often stop driving when they are not tired and cannot easily sleep, and often operate a vehicle when they are drowsy, even while abiding by the prescriptive work-rest rules. The NSIR driver is thus faced with a dilemma while on duty: he can comply with the strict HoS regulations which define when he should sleep despite not being fatigued, or he can sleep when he is drowsy, but face the risk of punishment for violating HoS regulations.

The fatigue risk assessment system of the present invention offers a solution which addresses the abovementioned dilemma by introducing an embodiment of the FRISPB paradigm specifically designed for NSIR drivers. This feature of the present invention offers several advantages over the current prescriptive HoS regulations. In particular, the FRISPB paradigm addresses the safety risk on highways caused by sleep deprivation and the hours that the CMV driver is continuously awake, and does not consider the main safety risk on highways to be hours of driving or hours on duty. In addition, the FRISPB paradigm is an alternative regulatory paradigm based on physiological science and transportation research. Further, the FRISPB paradigm has been scientifically validated in trucking operations, with results indicating substantial reductions in accidents, personal injuries, and driver turnover.

The FRISPB paradigm applies a set of Flexible Sleep Management (FSM) rules, which permit the timing of sleep to address the individual physiological needs of the driver, including alertness, health, and safety, rather than that arbitrary and capricious consequences of current HoS regulations.

Key features of the FSM rules proposal require:
Trained and qualified drivers who are educated to make informed choices as when and where to sleep;
FSM rules requiring 10 hours of rest per day, but no stipulation as to when the rest should be taken;
Monitoring using vehicle telematics systems, for example, GPS tracking systems, Engine (ECM) downloads, or any equivalent telematics system;
Fatigue risk assessment using scientifically-validated expert systems, for example, the abovementioned CAS expert system, that evaluate how drivers manage their sleep deprivation risk;

Proper compliance by applying FRISPB safety management principles.

More specifically, qualified, trained, and monitored NSIR drivers operate under the following FSM rules:

Drivers must take a minimum of 10 hours rest in each consecutive 24-hour period.

Each driver is responsible for avoiding sleep deprivation on a daily basis. This is facilitated by allowing her to be in complete control of her sleep time throughout each day (i.e., a 24-hour period). She may split her off-duty period rest increments to best meet her own individual sleep needs within a minimum of 10 aggregated off-duty hours.

Each trip assignment must be documented such that enough time is allowed for adequate off-duty time and legal travel time to complete the assignment.

The NSIR driver is limited to a maximum, aggregate non-consecutive 14 hours on-duty time each day In one embodiment, a driver may extend her duty-time to 16 hours to reach home or drop off a load not more than twice a week, provided that the reduction in off-duty time after dropping off a load is paid back by an equal amount of extra off-duty time spread over the next two days.

Safety and driver health objectives are assured using a scientifically-validated FRISPB expert system, which has been shown to significantly reduce truck accidents, injuries and driver turnover.

Monitoring and validation of actual work and rest hours of the driver can be made by a monitoring system. In an embodiment, the monitoring system is a telematics system. The telematics system can be a GPS tracking system, electronic control module (ECM) download, or any equivalent system.

In one embodiment, on-duty and driving time would be combined with on-duty status and show as on-duty on the log. Therefore, the log would have only two duty status categories: off-duty and on-duty times. Since off-duty time is the controlling factor for alertness, only supporting data to show off-duty time would be necessary.

Drivers would be assigned CMVs equipped with sleeping accommodations that exceed FMCSR Section §393.76, which provides sleeper berth specifications, throughout his tour of duty and throughout the extended period away from home. In particular, NSIR drivers under the FRISPB program are provided with CMVs equipped with climate-controlled motor-home like accommodations with large living and sleeping quarters. Most are equipped with TVs, refrigerators, sound systems, computer tables, closets, etc. The FRISPB program does not use basic, plain, day-cab work trucks that are slip-seated regularly (sometimes one or more times a day) used by local and short haul CMVs.

Participation in the Flexible Sleep Management option is voluntary by the driver.

If the carrier believes the driver is not suited for this option, it may remove the driver from this option.

Therefore, in order to assure that equivalent or greater levels of safety and driver health are maintained under the FSM rules, the FRISPB paradigm can be applied as the basis for alternative regulations in place of current HoS regulations, or as allowed under exemptions or waivers from current HoS regulations.

A Risk-Informed Performance-Based (RIPB) paradigm has been adopted by government agencies such as the Nuclear Regulatory Commission (NRC) to regulate the myriad of safety aspects of nuclear power plants. It places the responsibility on the operator to find the most effective way to get the desired safety outcomes, rather than writing excessively complex and unmanageable prescriptive regulatory rules that are insensitive to local operating conditions or technology.

In one embodiment the FRISPB safety management process described herein for NSIR drivers provides several layers of protection to safeguard driver safety and health, including:

1. Selection of volunteer NSIR drivers, according to an established standard, and their retention in the program only with management approval.
2. Special training of drivers on circadian sleep and alertness physiology, FSM rules, and maintaining good health on a truckload driver lifestyle, with testing to establish their personal sleep personality, and subject matter testing to ensure they are qualified for the FSM program.
3. The best judgment of a qualified, trained and monitored driver on when to obtain his best quality rest and sleep on a day-by-day basis.
4. Ongoing electronic monitoring to objectively confirm Hours of Rest using telematics, for example, GPS or ECM download.
5. Ongoing fatigue risk assessment of each driver using a scientifically-validated expert risk assessment system, and regular feedback, for example, daily, weekly or monthly feedback, of each driver's individual fatigue risk score to him, his dispatchers and managers.
6. Management oversight which holds drivers accountable for maintaining safe fatigue risk scores.
7. Conformance with Federal Motor Carrier Safety Administration Section §392.3 which prohibits the NSIR driver from driving while fatigued and prohibits management from requiring him to drive while his alertness is impaired.

An additional feature of the FRISPB paradigm is that there is no need to replace the current HoS regulations with the FRISPB paradigm. For many fixed truck route operations, current HoS regulations is sufficient. Instead, the HoS regulations can be revised, or an exemption or waiver can be approved, to contain a provision for for trucking companies who are willing to install and manage a FRISPB system to operate under FSM rules.

Therefore, FSM rules are a viable alternative to current HoS rules, particularly for qualified, irregular-route truckload operations that meet the conditions stated herein for a FRISPB safety management system.

As discussed above, fatigue risk assessment systems and methods of the present invention apply the abovementioned FRISPB paradigm to measure fatigue risk. The FRISPB paradigm and its application to fatigue risk in CMV operators, for example, NSIR drivers, will now be described. The data and scientific evidence on which the FRISPB paradigm is validated, is based on the following conclusions:

1. Ensuring the commercial vehicle drivers obtain adequate and timely sleep is essential to highway safety and driver health.
2. The "new" Hours of Service (post-2004 and 2005 revisions) offer some opportunities for increased driver sleep as compared to "old" Hours of Service (pre-2004) for certain groups or types of truck drivers, but not all truck drivers.
3. The need for Flexible Sleep Management I: Sleep duration not only depends on the duration of prior wakefulness, but also on the circadian time of day.

4. The need for Flexible Sleep Management II: Individual differences in sleep physiology and the circadian (biological) clock means that drivers cannot all be treated identically.
5. The need for Flexible Sleep Management III: Naps should be encouraged and not penalized by a 14-hour on duty clock.
6. FRISPB safety management using scientifically-validated risk assessment systems offer a superior level of safety than the traditional fixed Hours of Service compliance paradigm.
7. Flexible Sleep Management (FSM) rules minimize the risk of sleep deprivation by allowing drivers the flexibility to stop for sleep when then are tired and drive when alert.
8. Expert risk assessment systems which continuously assess driver sleep deprivation fatigue risk permit monitoring of compliance with FSM rules.
9. Truckload Operation Field Trials and Duty Rest-Simulations demonstrate that Safety is "equivalent or greater" with the FRISPB paradigm.
10. Federal Hours of Service regulations should permit specific exemptions for truckload carriers which adopt FSM rules with appropriate driver training and with FRISPB compliance ensured by scientifically-validated expert systems to monitor risk.

1. Ensuring that Commercial Vehicle Drivers Obtain Adequate and Timely Sleep is Essential to Highway Safety and Driver Health By focusing on numerical counts of "hours on duty", "hours of driving", and "hours off duty" after beginning a work week, current HoS regulations ignore an obvious fact. According to Moore-Ede, M. and Schlesigner, B., "Scientific Basis for Challenges to Work-Rest & Hours of Service Regulations," J Transport Law Logistics Policy 71: 262-279, 2004, incorporated herein in its entirety by reference, the alertness, safe performance and health of a driver depends more on how sleep-deprived he is behind the wheel, and less on how many hours he has been on duty or driving. According to Moore-Ede, M., "Fatigue in Transportation Operations Clin Occup Environ," Med 2: 11-27, 2002, incorporated herein in its entirety by reference, it matters how many hours elapsed since the driver last slept, how long he slept, the quality of his sleep, and how much sleep he recently received, for example, the amount of sleep over the previous week. For reasons explained below, a driver can be asked while on duty to drive a vehicle after being continuously awake for 16, or even 24 hours, yet the HoS paradigm judges this driver to be fully rested. For example, the driver may have spent the previous day not sleeping, but instead performing activities did not include sleep, resulting in the driver being as fatigued as he would had been had he been driving his truck during the same period.

The Flexible Sleep Management (FSM) rules are designed to optimize the amount and quality of sleep that is obtained by non-scheduled irregular-route truckload (NSIR) drivers, and to do this better than the current HoS paradigm, so as to improve highway safety and driver health, and provide more consecutive off-duty days at home.

The principle concern is that there are multiple features of the current HoS regulations (in pre-2004, 2004, and 2005 versions) that impede the NSIR driver from getting the sleep he needs, or that add inflexible complexities to his daily schedule which discourage him from stopping to sleep or briefly nap when he really needs it, and which motivate him to drive when he should sleep. As previously pointed out and supported by many scientific studies, sleep deprivation leads to impaired alertness and performance. See Pilcher J, Huffcut A. "Effects of sleep deprivation on performance: A meta-analysis," Sleep 1996; 19[4], 318-326, incorporated herein in its entirety by reference. According to Lenne M G, Triggs T J, Redman J R. "Interactive effects of sleep deprivation, time of day, and driving experience on a driving task," Sleep 1998; 21(1):38-44, incorporated herein in its entirety by reference, driving simulator experiments have shown that performance decrements caused by sleep deprivation affect driving parameters such as speed variability, lane drifts and the ability to respond to additional stimuli. Hence, the following discussion briefly summarizes the considerable body of science which shows that sleep is critical to driver safety, health, and well-being. In this context the effects of both acute sleep deprivation are addressed—caused by the length of the prior sleep period and the number of hours continuously awake, and chronic sleep deprivation—the consequence of inadequate amounts of sleep over successive days.

Acute Sleep Deprivation

When people who have previously been sleeping at night, extend their normal period of daytime wakefulness into night-time hours, progressive deterioration of a wide range of performance and attentiveness measures occurs. For example, Dawson and Reid "Fatigue, alcohol and performance impairment," Nature 1997; 388:235, incorporated herein in its entirety by reference, showed that extended periods of time awake (17 to 24 hours of sustained wakefulness) impair performance to an extent equivalent to the performance decrements resulting from alcohol ingestion. The performance decrements for each additional hour of wakefulness between 10 and 26 hours was equivalent to the performance decrement resulting from a 0.004% rise in blood alcohol concentration, with an impairment equivalence being established between blood alcohol concentrations of 0.05%, 0.08% and 0.10% for continuous periods of wakefulness of 17, 22 and 24 hours, respectively. Another study by Arnedt J T, Wilde P, MacLean A W. "Simulated driving performance following prolonged wakefulness and alcohol consumption: separate and combined contributions to impairment," Journal of Sleep Research 2000; 9(3):233-241, incorporated herein in its entirety by reference, showed that the deterioration in simulator driving performance, following 24 hours of extended wakefulness, is comparable to the decrement resulting from a blood alcohol concentration of 0.08%.

However, HoS regulations address time-on-duty, not time awake. On duty time, or driving time by themselves are not accurate predictors of alertness and performance as time of prior wakefulness can be considerably longer than time on duty. Drivers may come on duty, and start driving at any time of the 24 hour day. There is no guarantee that driver is alert during early duty hours since personal activities before coming on-duty can prevent sleep just as much as driving or other on-duty activities.

FIG. 1 contains a graph illustrating variations in alertness levels of two truck drivers both operating legally under current FMCSA HoS regulations but with different levels of fatigue risk, i.e. inversely related to level of alertness, during different time periods of a work shift according to laws of circadian sleep physiology.

To illustrate the problem with a simplified example (not considering refuel & meal breaks), consider two truck drivers (A & B), as shown in FIG. 1, each about to start the maximum 11-hour driving shift prescribed under the post-2004 Hours-of-Service. Both are fully rested after a full night of sleep at home from 11 PM to 7 AM, and then both are called at short notice to pick-up a load. Driver A is dispatched to start driving at 8 AM, but driver B is not dispatched until 10 PM. Driver A can be expected to be fully alert driving his truck through to 7 PM and beyond, but has to stop driving at 7 PM because he has reached the 11 hour limit, even though he could safely drive (albeit illegally) without any significant fatigue for at least another one or two hours. Driver B, on the other hand, because he was fully rested by his prior night's sleep is unlikely to want to, or be able to, nap during the day while waiting for a load. Therefore Driver B is likely to become significantly fatigued by about 4 AM, only six hours into his drive, because he would have been awake for 20 hours at that point. Hence if Driver B keeps on driving after only six hours on the road, he is perfectly legal but unsafe, whereas Driver A continuing to drive after 11 hours of driving would be perfectly safe, but illegal.

There are two major factors at play in the impairment of Driver B: the homeostatic and circadian drives to sleepiness. The HoS paradigm does not directly address either of them. It must be noted that there are many features of the current Hours of Service paradigm that indirectly address the homeostatic and circadian drives to sleepiness. However, the illustrations described below show that because they are indirect and inflexible they can impede the attempts of NSIR drivers trained in sleep management to time their sleep and naps to maximal advantage to address homeostatic and circadian factors. That is why Flexible Sleep Management rules are preferable and safer for the NSIR driver. With increasing elapsed time since sleep, sleep pressure builds and sleepiness-impairment develops, and this is called the homeostatic drive. See Borbely A A, Achermann P. "Concepts and models of sleep regulation: an overview," Journal of Sleep Research 1992; 1:63-79, incorporated herein in its entirety by reference. By not directly considering time since last sleep, especially on the first workday of the week, the HoS paradigm does not address this homeostatic drive. However the homeostatic drive is also strongly modified by the circadian drive, the influence of the human biological clock (circadian pacemaker) which controls the timing of virtually all body functions across the day-night cycle. See Moore-Ede M C, Sulzman F M, Fuller C A. The Clocks That Time Us: Physiology of the Circadian Timing System. Cambridge, Mass.: Harvard University Press; 1982, incorporated herein in its entirety by reference. People are most impaired at the circadian nadir, the time in the latter half of the normal daily sleep period (for night sleepers usually 3-5 AM). See Moore-Ede M C. "The Twenty-Four Hour Society: Understanding Human Limits in a World That Never Stops," Reading, Mass., Addison-Wesley Publishing Co.; 1993, incorporated herein in its entirety by reference. Since Driver B in this example had previously been sleeping at night, when he had driven for only 6 hours, not only had he been awake for 20 hours, but he also had reached his circadian nadir of maximal impairment at approximately 4-5 AM because of his circadian drive to sleepiness. The HoS paradigm takes no direct account of this circadian drive, and regards Driver B as unimpaired and fully compliant, since it is indifferent to both time of day and time continuously awake.

Appropriately timed sleep cures both the homeostatic and circadian drives to sleepiness-impairment, no matter the time of day or night. The fact that sleep addresses impairment caused by elapsed time since last sleep is obvious, the circadian time of day will now be described.

Many studies have shown that the risk of loss of attention accidents peaks at the time of the circadian nadir. When the data is appropriately corrected for number of vehicles at risk on the highways per hour of day, single vehicle run-off the road accidents and other driver fatigue-related accidents reach a peak between 3 AM and 5 AM, and simulator studies show increased risk of drowsiness and microsleep events around this time. See Langlois P H, Smolensky M H, Hsi B P, Weir F W. "Temporal patterns of reported single-vehicle car and truck accidents in Texas, U.S.A. during 1980-1983," Chronobiology International 1985; 2(2):131-146, incorporated herein in its entirety by reference. See also, Akerstedt T. "Work hours, sleepiness and the underlying mechanisms," Journal of Sleep Research 1995; 4(Suppl.2):15-22, incorporated herein in its entirety by reference. See also Moore-Ede M C, Guttkuhn R, Heitmann A, Trutschel U, Lahoud J, Cleveland D, Norloff P. "Automatic detection of microsleep events using a neural-fuzzy hybrid system," Ocular Measures of Driver Alertness 1999; FHWA-MC-99-136; p. 98-107, incorporated herein in its entirety by reference.

Some have used this data to conclude that it is inherently more unsafe to drive at night. However this is not necessarily the case. There much less traffic at night, and any overall shift of truck driving hours onto the daytime highways would only increase highway congestion and accident risk. Also, and more importantly, the increased nighttime risk argument is flawed because it overlooks the issue of time since last sleep.

The main cause of the observed increased driver fatigue risk in the early morning hours is from the combination of homeostatic and circadian factors, exemplified by Driver B in the example above, and to a much lesser extent from the time of day alone. Individuals driving on the highways at 4-5 AM who have had adequate sleep within the past several hours are not at especial risk, whereas those who have been continuously awake since the prior morning are likely to be impaired. Most studies of accident risk by time of day, fail to distinguish between these two very different groups.

Chronic Sleep Deprivation

It is not only acute sleep deprivation, but also chronic sleep deprivation that contributes to impairments in alertness, performance and safety. Sleep deprivation over multiple days has a cumulative effect. See Carskadon M A, Dement W C. "Cumulative effects of sleep restriction on daytime sleepiness," Psychophysiology 1981; 18:107-113, incorporated herein in its entirety by reference. See also Van Dongen H, Maislin G, Mullington J, Dinges D. "The cumulative cost of additional wakefulness: dose-response effect on neurobehavioral functions and sleep physiology from chronic sleep restriction and total sleep deprivation," Sleep 2003; 26:117, incorporated herein in its entirety by reference. One concern is that the current inflexible HoS regulatory paradigm often leads to situations where NSIR drivers are not able to obtain sufficient sleep. Indeed, it is explained in greater detail below that the current inflexible regulations require them to rest at times of day when sleep is hard to obtain, encourage NSIR drivers to truncate sleep when it is most needed, and discourage them from interrupting their duty time for taking brief naps. As an unintentional result of such HoS regulations many NSIR drivers (if they obey the current rules) are subjected to high levels of chronic sleep deprivation in addition to potential acute sleep deprivation on any particular day. More flexible rules are required for the NSIR driver to enable him to prevent cumulative sleep debt on a daily basis.

Chronic sleep deprivation has been demonstrated to negatively impact health. As pointed out in the FMCSA proposed rules, FMCSA-2004-19608. Federal Register/Vol. 70, No. 14/Monday, Jan. 24, 2005/Proposed Rules "Hours of Service of Drivers" p. 3344, incorporated herein in its entirety by reference, "Serious adverse health conditions appear to be associated with chronic sleep deprivation." Sleep is essential. It promotes growth, protects and preserves brain and immune function, and many important hormones are active during sleep. Sleep deprivation seriously disrupts immune and hormone systems, at least temporarily. A growing body of research does indicate that lack of sleep may be even more harmful than previously thought. It may be contributing to obesity by changing metabolism, and to heart disease by causing low-grade inflammation. A recent review on the impact of sleep duration on health by Alvarez G, Ayas N. "The impact of daily sleep duration on health: a review of the literature." Prog Cardiovasc Nurs 2004; 19(2):68-69, incorporated herein in its entirety by reference, summarized "under strict experimental conditions, short-term restriction of sleep results in a variety of adverse physiologic effects, including hypertension, activation of the sympathetic nervous system, impairment of glucose control, and increased inflammation."

Restricting sleep in healthy young men to four hours per night for only six nights can induce changes in carbohydrate metabolism and endocrine functions, which the authors likened to changes seen in normal aging. See Spiegel K, Leproult R, Van Cauter E. "Impact of sleep debt on metabolic and endocrine function," The Lancet 1999; 354:1435-1439, incorporated herein in its entirety by reference. Two other recent studies demonstrated that short sleep is associated with changes in the appetite-regulating hormones leptin and ghrelin, leading to increased hunger and appetite and possibly increasing the risk of obesity. See Taheri S, Lin L, Austin D, Young T, Mignot E. "Short sleep duration is associated with reduced leptin, elevated ghrelin, and increased body mass index," PLOS Medicine 2004; 1(3):e62, incorporated herein in its entirety by reference. See also Spiegel K, Tasali E, Penev P, Van Cauter E. "Brief communication: sleep curtailment in healthy young men is associated with decreased leptin levels, elevated ghrelin levels, and increased hunger and appetite," Ann Intern Med 2004; 141(11):846-850, incorporated herein in its entirety by reference.

Reasonable Daily Sleep Need

However, it is important to be realistic in establishing the reasonable sleep needs of adults. As Horne J A. "Is there a sleep debt?" Sleep 2004; 27(6):1047-1049, incorporated herein in its entirety by reference, points out, the average adult needs 7 to 7.5 hours, not the 8 or more that is often asserted, based on laboratory sleep research studies often performed on college age students, many of whom are too young to obtain a commercial driver license (CDL). Furthermore in the abnormal laboratory world of unrestricted sleep studies, sleep expands to fill the time available, partly because of boredom and lack of competing stimulation.

It is important to distinguish in experiments, as we do in trucker Hours of Service, between the length of the sleep opportunity, and the actual length of sleep. Even in studies where subjects have been given an 8-hour nocturnal (11:30 PM to 7:30 AM) sleep opportunity under the controlled conditions of a sleep lab over a two week period, they actually choose to sleep for only 6.7 hours. Arguments that there is a human daily sleep need in excess of 8-hours have been made from such studies, but this is based on the subjects' maximal ability to perform a very monotonous performance test, the PVT, which has no learning curve. Whatever aspect of human performance this experimental task is measuring is therefore rather different than the daily job of a long-distance truck driver which has a significant learning curve and a significantly more stimulating task, even on the open highway.

When truck drivers were asked in the FHWA driver fatigue study to complete the statement "My ideal amount of sleep is X hours" they answered on average 7.1 hours. See Mitler M M, Miller J C, Lipsitz J J, Walsh J K, Wylie C D. "The sleep of long-haul truck drivers," New England Journal of Medicine 1997; 337(11):755-761, incorporated herein in its entirety by reference. While there is some individual variation in sleep needs, there is other data which supports that 7 to 7.5 hours is a reasonable daily sleep requirement. For example, it should be noted that 7 hour a night sleepers on average have the greatest longevity. See Kripke D F, Garfinkel L, Wingard D L, Klauber M R, Marler M R. "Mortality associated with sleep duration and insomnia," Arch Gen Psychiatry 2002; 59:131-136, incorporated herein in its entirety by reference. In a study of over a million people, those who slept 8 hours or more had a substantially greater risk of death in the next six years, as did those who slept 6 hours or less. Similarly a study of diabetes risk shows a U-shaped relationship between sleep length and risk, with people obtaining 7 hours sleep per night in the middle of the lowest risk range. See Ayas N T, White D B, Al-Delaimy W K, Manson J E, Stampfer M J, Speizer F E et al., "A prospective study of self-reported sleep duration and incidents of diabetes in woman," Diabetes Care 2003; 26(2): 380-384, incorporated herein in its entirety by reference.

The foregoing discussion has shown that obtaining adequate sleep, typically 7-7.5 hours per day, is vital for ensuring driver alertness, safe driving performance, and health. Any feature in HoS regulations that would prevent or discourage a driver from getting adequate sleep is undesirable. Similarly Flexible Sleep Management rules that would encourage and provide a NSIR driver with the optimal flexibility needed to obtain sleep and naps is desirable.

2. The New Hours of Service (Post-2004 and 2005 Revision) Improve Driver Sleep as Compared to the Old Hours of Service (Pre-2004) for Certain Groups of Truck Drivers, But not all Truck Drivers.

Hours of Service (HoS) regulations present a dilemma for the FMCSA, and other transportation agencies. Based on a simple but flawed regulatory paradigm originally developed in the early 1900s, they have become out-dated by advances in circadian, sleep and alertness physiology, and the technology and operations of modern transportation. Unfortunately, the interaction of circadian sleep science and modern operational practices is sufficiently complex that it cannot readily be written into simple prescriptive rules that are enforceable or understandable by drivers, managers or law enforcement officers.

However, the FMCSA has to date been constrained to making changes within the HoS regulatory paradigm in both Jan. 4, 2004 and Oct. $1^{st}$ 2005 revisions.

For NSIR drivers in particular, both old and new HoS regulations have substantial shortcomings because they prevent the flexibility in sleep timing that NSIR drivers need, as discussed in detail below. However before discussing the special problems faced by NSIR drivers, it is important to note that the new HoS regulations do represent an important improvement over the old HoS regulations in attempting to reduce driver sleep deprivation. The most important changes to the rules include the following:

Increasing the Mandatory Off-duty Time Per Day from Eight to Ten Hours.

A general consensus has been established in the scientific community that 7-8 hours of sleep per day is necessary to maintain adequate alertness. While there are individual differences in sleep need, 49% of American said they need 7 or more hours of sleep to be rested, and half need less. See National Sleep Foundation. 2002 "Sleep in America" Poll. 1-43. 2002, incorporated herein in its entirety by reference. As discussed, truck drivers report similar sleep needs to those of the general US population, with a mean reported need of 7.1 hours. But while 7-7.5 hours is generally viewed as an adequate amount of sleep per day, the 8 hour off-duty period prescribed by the old HoS regulations did not ensure sleep for 7 or 8 hours. Most likely, a driver would include at least one and possibly two meals in this time period, as well as possibly a shower, and personal time (i.e., phone calls, television, etc.). By the time these activities were subtracted, a driver would be lucky to get as much as 6 hours of sleep in an eight-hour off-duty period. With the 10-hour break that is mandated by the new rules, drivers are able to complete other off-duty activities and have an opportunity to sleep for 7-8 hours.

However, for reasons described below, 7-8 hours sleep is not physiologically feasible to obtain in 10 hour rest periods commencing at certain times of day, so the NSIR driver needs flexibility to obtain his sleep at whatever time of day he needs it.

Restrictions on the Extension of the Workday Due to Waiting Time.

The "running clock" concept, whereby a driver cannot drive beyond the $14^{th}$ hour following the commencement of a day's duty, is an improvement over the method that was used in the old rules, which allowed waiting time at loading docks to cause virtually unlimited extensions of the work day. The amount of time elapsed since a driver's last sleep period is more important to determining his alertness at the end of the workday than is the count of hours driven and/or worked so far that day. Under the old HoS regulations, a driver could have legally driven 20 or more hours after his day started by mixing off duty and non-driving time into his day. The "running clock" ties a driver's ability to be behind the wheel to how long he has been duty, rather than how he has divided his work. As discussed below, the new HoS regulations still do not necessarily prevent extended hours awake, but they do make restrict truck drivers from being on-duty over extended periods of time.

However, this 14-hour clock rule currently discourages NSIR drivers from taking brief naps and rest breaks.

Lengthening the Minimum Day-night Cycle.

By extending both the number of hours of rest required per day (e.g., from 8 hours to 10 hours), and the number of hours of driving allowed (e.g., from 10 hours to 111 hours), the new HoS regulations have essentially lengthened the "minimum day-night cycle" from 18 hours to 21 hours that a driver can live on, assuming he is attempting to maximize driving time (and has no on-duty not-driving time), This change reduces the likelihood and severity of drivers falling into backward rotation schedules, where each day starts hours earlier than the previous day. A driver working an 18-hour daily rotation under the old HoS rules would be rotating backward by six hours per day. This means that if his first day started at 8 AM, his second day would start at 2 AM, his third day would start at 8 PM, and so on. Numerous studies have shown that schedules that rotate backward are likely to cause fatigue and health problems. See Czeisler C A, Moore-Ede M C, Coleman R H. "Rotating shift work schedules that disrupt sleep are improved by applying circadian principles," Science 1982; 217:460-463, incorporated herein in its entirety by reference. See also Knauth P. "Speed and direction of shift rotation," J Sleep Res 1995; 4(suppl. 2):41-46, incorporated herein in its entirety by reference. While the new HoS regulations still allow for schedules that rotate backward, the extension of the mandated rest period at least acts to reduce the severity of the rotation.

However, a driver can still work a schedule that rotates backward by six hours or even more, by simply not driving for the maximum 11 hours per day.

Establishing a 24-hour Cycle

Furthermore, the new HoS regulations make an effort to place drivers on a 24-hour daily schedule that would be most compatible with their circadian rhythms. If a driver works the full 14-hour day (11 hours driving+3 hours on duty, not driving) on Monday, and then rests for 10 hours, he would start on Tuesday at the same time he had started on Monday. Establishing such regular patterns would seem preferable from a physiological standpoint and the new HoS regulations have an advantage over the old HoS regulations for attempting to assist drivers in doing so. Under the old HoS regulations, a driver maximizing his work time could work 15 hours and then rest for 8, making for a 23-hour day. But since there was no "running clock" system in place, breaks and off-duty time could serve to extend the 15-hour period by multiple hours. Drivers were left to nothing but their own education and chance to determine whether their schedules would approximate a 24-hour pattern.

However, locking a NSIR driver onto a 24-hour clock is not necessarily ideal if the first off-duty period starts at an undesirable circadian time of day for sleep because the driver thereafter is confined to night driving and day sleep.

Restrictions on Splitting the Daily Sleep Period

The 2005 revisions contained new provisions which further limit how sleep periods may be split. Now one of the two periods has to be at least 8 hours in length. This means that drivers who sleep at for example 11 AM and can only in the best of conditions get 4 hours sleep because of human circadian physiology, now must wait for at least 4 hours before starting driving in the evening and overnight, instead of using the hours after a four hour sleep to drive safely when they are not fatigued, and then catch up with the rest of their daily sleep in the nocturnal hours when it is likely to be more effective and more easily obtained.

Considering all these issues together we conclude that the new post-2004 HoS regulations make some useful steps forward in promoting driver sleep and health as compared to the pre-2004 regulations. However, the fundamental underlying problems of the prescriptive HoS paradigm for NSIR drivers has not been addressed by the revisions to HoS introduced on Jan. $4^{th}$ 2004. There still remains a substantial regulatory impediment for the management of optimal sleep for the NSIR driver, as described more fully below.

3. The Need for Flexible Sleep Management I: Sleep Duration Depends not Only on the Duration of Prior Wakefulness, But Also on the Circadian Time of Day Next, the combination of time awake and time of day effects on ability to sleep is discussed which questions the merit of fixed HoS rest period rules. This question is raised because optimal sleep is not easily achieved under the broad range of permutations and combinations of NSIR driver schedules when drivers are constrained by the current fixed prescriptive rules. Following this discussion, several issues are addressed, including the issue of circadian phase, driving across time zones, genetically-inherited differences in sleep and circadian physiology, and driver age which all add further evidence for the need for regulatory flexibility for the NSIR driver.

Leaving aside for the moment the complexities of the split-sleeper exemption, the question is raised regarding the logic of providing for a 10 consecutive hours minimum rest period no matter the time of day or night. This aspect of the HoS regulatory paradigm fails to consider a fundamental aspect of circadian sleep-wake physiology—the duration of sleep that is obtainable by a healthy person even under ideal conditions is highly dependent on time since last sleep and the circadian time of day. As shown below, the assumption that 8 hours sleep is the norm and therefore a 10 hour continuous rest period is ideal, is flawed when considered in the context of 24/7 operations where duty-time or driving time limits can enforce the beginning of rest periods at every possible hour of the 24 hour day.

There are certain times of day when it is difficult to obtain more than four hours sleep, even under ideal conditions, and with the most highly motivated individual. The current HoS requirement for a ten hour rest period would, in these circumstances, require a driver to wait for up to six hours getting "unrested", before being able to drive again. Driving during that illegal six hour waiting period would most likely be safe, because it is in such close proximity to the time of waking up from sleep. Starting to drive after "twiddling one's thumbs" waiting in some remote location for six hours is correspondingly less safe. The evidence behind these conclusions is based on the research studies which is discussed below.

Circadian and Homeostatic Influences on Duration of Sleep

Just like their impact on sleepiness-impairment discussed above, the homeostatic and circadian drives have a powerful influence on the duration and quality of sleep obtained during periods of rest. Many scientific studies have demonstrated that the quantity and quality of sleep depends on the duration of prior wakefulness (homeostatic influence; process S) and the timing of sleep (circadian influence; process C). For example, as discussed by Akerstedt, incorporated herein in its entirety by reference, "subjective sleep quality, calmness of sleep, ease of falling asleep, ability to 'sleep through', number of awakenings, and sleep latency showed a significant pattern of 'better' sleep with increasing prior time awake and with closeness to the circadian minimum (nadir) of rectal temperature (early morning hours)."

General concerns regarding the current HoS paradigm relate particularly to the circadian effects on sleep duration. The circadian dependency of sleep duration has been demonstrated in many studies. Czeisler C A, Weitzman E, Moore-Ede M C, Zimmerman J C, Knauer R S. "Human sleep: its duration and organization depend on its circadian phase," Science 1980; 210:1264-1267, incorporated herein in its entirety by reference. See also Dijk D-J, Czeisler C A. "Contribution of the circadian pacemaker and the sleep homeostat to sleep propensity, sleep structure, electroencephalographic slow waves, and sleep spindle activity in humans," The Journal of Neuroscience 1995; 15(5):3526-3538, incorporated herein in its entirety by reference. While many of these studies were carried out under special experimental conditions designed to tease out the characteristics of circadian physiology (e.g., non-24 hr periods, long term isolation, desynchronization of rhythms, self-selected schedules, etc.), the circadian sleep effects have also been confirmed in studies under more directly relevant conditions.

Figure 2A:
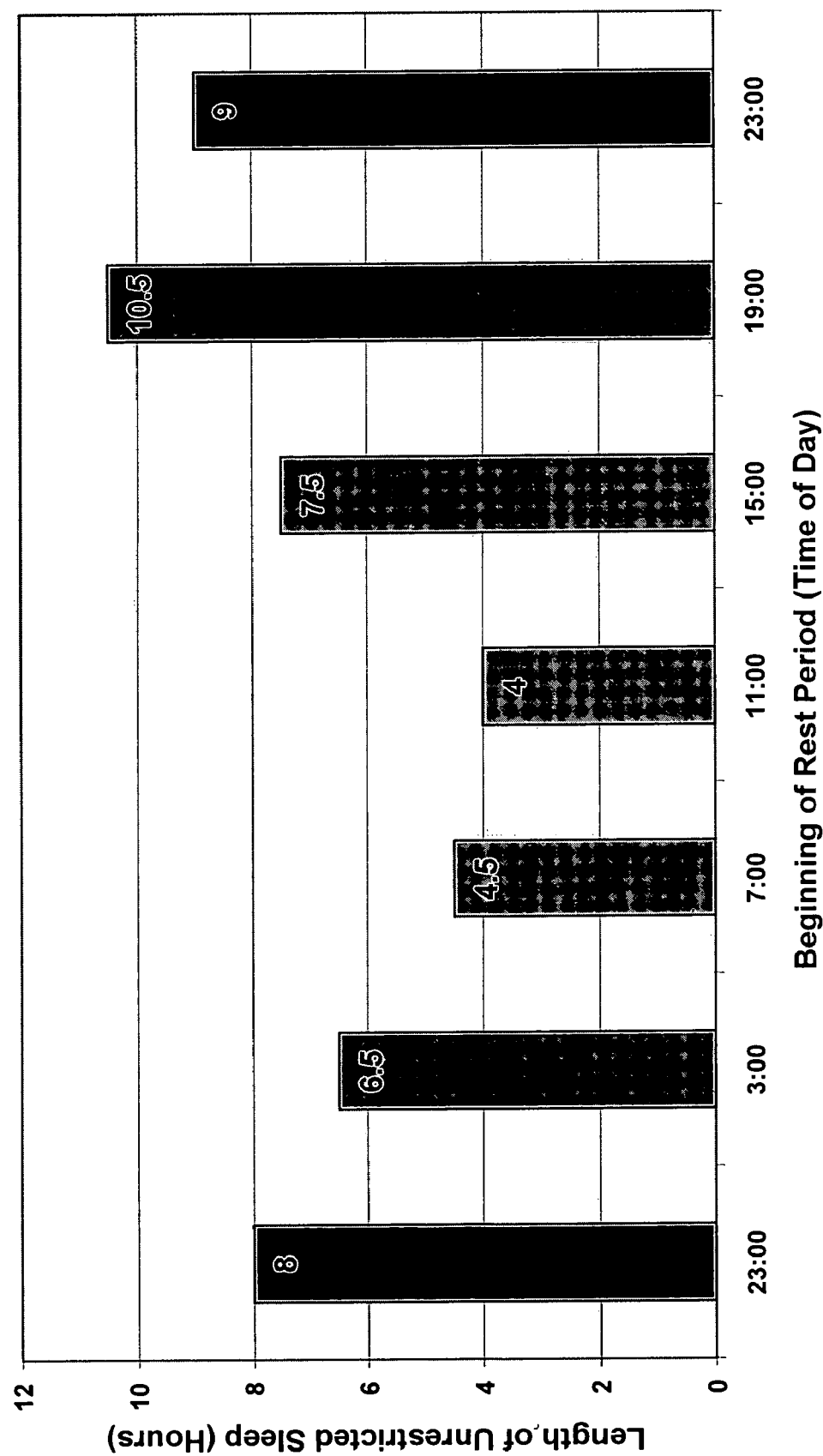
FIG. 2A contains a graph illustrating the circadian effects on sleep duration with unrestricted sleep opportunities.
Figure 2B:
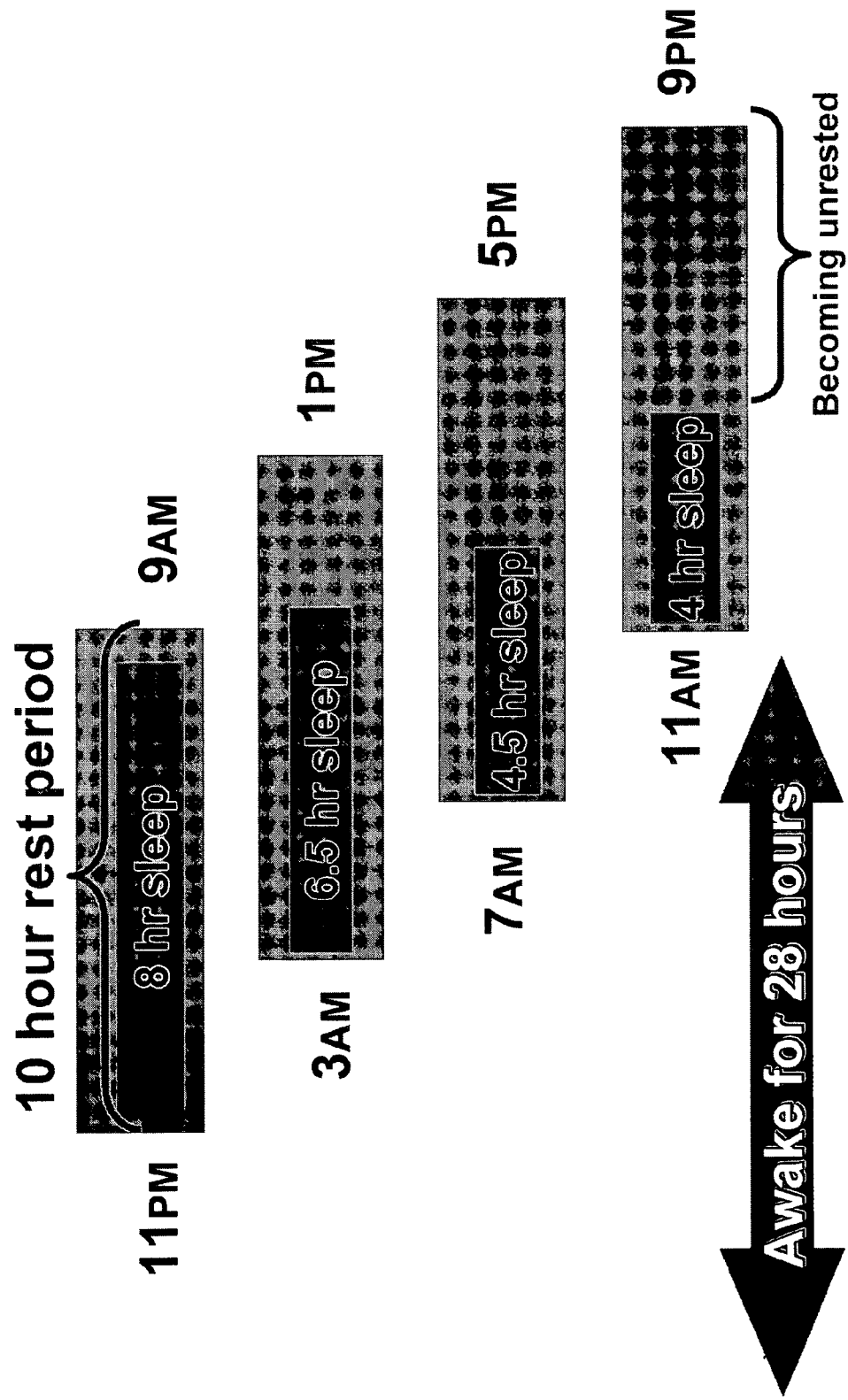
FIG. 2B contains a graph illustrating the circadian effects on sleep duration with 10 hour rest periods which occur at different times of day.

FIG. 2A contains a graph illustrating the circadian effects on sleep duration with unrestricted sleep opportunities. FIG. 2B contains a graph illustrating the circadian effects on sleep duration with 10 hour rest periods which begin at different times of day.

In FIG. 2A, the duration of sleep was obtained (in hours) when eight adult subjects (aged 29-45) were given an ideal unrestricted sleep opportunity in a quiet bedroom beginning at various times of day. They were either previously kept awake for 16 hours (11 PM bedtime), 20 hours (3 AM bedtime); 24 hours (7 AM bedtime), 28 hours (11 AM bedtime); 32 hours (3 PM bedtime); 36 hours (7 PM bedtime), and 40 hours (11 PM bedtime on the second day). The data in FIG. 2A is replotted from Akerstedt.

The studies of Akerstedt and Gillberg are particularly instructive. See Akerstedt T, Gillberg M. "A dose-response study of sleep loss and spontaneous sleep termination.," Psychophysiology 1986; 23(3):293-297, incorporated herein in its entirety by reference. They studied subjects (aged 29-45) who were given an opportunity to sleep under ideal conditions (quiet comfortable bedroom) during rest periods which started at various times of day or night. Sleep length was not restricted and the subjects were instructed to only get out of bed when they had got all the sleep they could obtain. Even under these ideal conditions, the amount of sleep these subjects were able to obtain was highly dependant on the time of day when the rest period began. Because Akerstedt and Gillberg's studies were conducted with subjects in an age range comparable to many truck drivers, they are more applicable than other studies performed in 18-21 year old college students, who have the hormonally-delayed sleep patterns of late adolescents. See Carskadon M A, Acebo C, Jenni, O G. Regulation of adolescent sleep: implications for behavior. Ann NY Acad Sci 2004; 1021:276-291, incorporated herein in its entirety by reference.

As FIGS. 2A and 2B show, when the rest period began at 11 PM (or 23:00) at the end of a normal day of 16 hours continuously awake, they slept on average for 8 hours, as one would expect given the unlimited sleeping opportunity. However the later the rest period began after 11 PM, the shorter was the sleep duration as a result of the strong circadian time of day effect. Thus when the rest period began at 3 AM (after 20 hours continuously awake) they achieved only 6.5 hours sleep, when rest began at 7 AM (after 24 hours continuously awake) they obtained only 4.5 hours sleep; when rest began at 11 AM (after 28 hours continuously awake) they got only 4 hours sleep. It was not until rest periods beginning at 3 PM (after 32 hours continuously awake) that sleep duration began to lengthen, and they slept for 6.5 hours. Maximum sleep lengths were obtained with rest periods beginning at 7 PM (after 36 hours continuously awake) when they slept for 10.5 hours. But the circadian effect continued to exert itself as evidenced by shorter sleep with the rest period beginning at 11 PM (now after 40 hours continuously awake) when sleep length was about 9 hours.

The strength of the circadian biological clock's control on sleep is evidenced by a comparison of the two rest periods which began at 11 PM, the first after 16 hours awake, and the second after 40 hours continuously awake. Despite 24 more consecutive hours of wakefulness only one additional hour of sleep was obtained—even under these ideal sleeping conditions.

Figure 3:
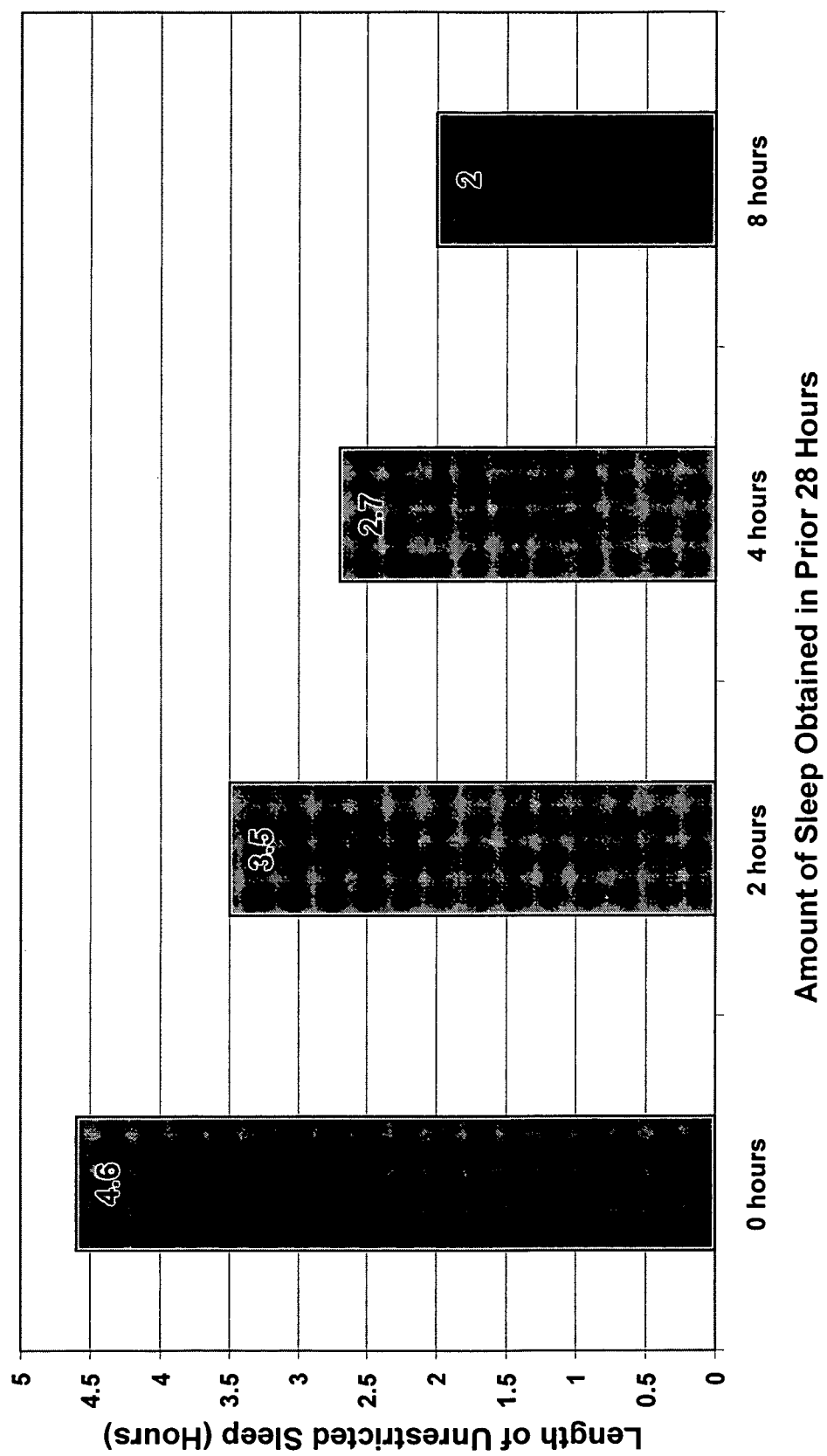
FIG. 3 contains a graph illustrating different durations of sleep obtained in rest periods beginning at 11 AM after a previous nap having different durations within the prior 28 hour period.

It should not be concluded from these studies that the homeostatic influence has little effect on sleep length. As shown in FIG. 3, Akerstedt and Gilberg repeated similar unrestricted sleep experiments with subjects starting their rest period at 11 AM, but allowed them to break the 28 hours continuously awake with a 2 hour, 4 hour or 8 hour nap/sleep during the night. The unrestricted sleep duration of 4.6 hours at 11 AM with no nap was shortened to 3.5 hours with the 2 hour nap, 2.7 hours with the 4 hour sleep, and only 2 hours if they had slept for a full 8 hours the prior night.

FIG. 3 contains a graph illustrating different durations of sleep obtained in rest periods beginning at 11 AM after a previous nap of different durations within the prior 28 hour period. The length of unrestricted sleep in rest periods beginning at 11 AM after 28 hours awake in a similar protocol to FIG. 2A, except that the 28 hours awake was interrupted by naps of either 0 (no nap), 2, 4 or 8 hours during the prior night. (Replotted from Akerstedt & Gilbert, incorporated herein in its entirety by reference).

It is noted that Rosekind M R. "Managing safety, alertness and performance through federal hours of service regulations: opportunities and challenges," FMCSA-2004-19608-1134, incorporated herein in its entirety by reference, recommends that split sleeper berth use be comprised of a 6.5 hour anchor sleep opportunity and a 2-hour nap opportunity based on a study referenced in a brief abstract. See Maislin G, Rogers N, Price N, Mullington J, Szuba M, Dinges D. "Response surface modeling of the effects of chronic sleep deprivation with and without diurnal naps," Sleep 2001; 24 (Abstract Supplement):A242, incorporated herein in its entirety by references.

A recent review by the same authors indicates this study involved a traditional sleep paradigm of nocturnal sleeps and diurnal naps. See Rogers N L, Dorian J, Dinges D F. "Sleep, waking and neurobehavioral performance," Frontiers in Bioscience 2003; 8:1056-1067, incorporated herein in its entirety by reference. Given the data of Akerstedt and Gilbert discussed above, it would be much too restrictive for NSIR drivers to live by Rosekind's formula, especially without knowing the driver's circadian phase or his sequence of prior naps and sleeps.

The relevance of Akerstedt and Gilbert's studies to the design of optimal rest rules and sleep strategies is vital to understand for trucking operations that have drivers beginning their required rest periods at all times of day and night. The short sleep lengths reported by truck drivers[24] cannot be simply dismissed as a result of less than ideal sleep conditions because of traffic noise, engine idling, and other disturbances. Even in ideal quiet bedroom environments sleep is very truncated at certain times of day. What is key is that the driver be given the freedom to catch up on sleep when he most needs it, and not be regulated according to a prescriptive formula.

Operational and Regulatory Factors Determining the Timing of Rest Periods

The problem of prescriptive HoS rules on duty, driving and rest periods for the NSIR driver becomes apparent when rest periods are enforced to begin at every possible hour of day and night. This is caused by:

1. Shippers' 24/7 schedules that determine when a load can be picked up, and therefore start the truck driver's HoS regulatory clock at any hour of day or night.
2. Rigidly calculated rules on driving and on-duty hours that require the driver to begin a rest period after a numerically-calculated number of hours, even when it may not be a desirable or physiologically-compatible time.

Using the maximum feasible durations of sleep under the ideal sleep opportunity of the Akerstedt and Gillberg studies, one can see how our bodies' natural "physiological sleep rules" respond in the following examples under the new HoS regulations:

In one example, Driver C picks up his load at 12 midnight and runs out of driving hours at 11 AM the next day, and thus must begin his rest period at 111 AM and remain at rest until 9 PM. The maximum sleep he can obtain at 11 AM is 4.5 hours until 3:30 PM. He then must wait for 5.5 hours until 9 PM before being allowed to drive again. However he would be much safer to drive at 3:30 PM than waiting until 9 PM and thereby getting increasingly "unrested" before being allowed to get on the road.

In another example, Driver D picks up his load at 8 PM and decides to stop to sleep for 4 hours in the middle of the night. He runs out of driving hours therefore at 11 AM. When he tries to sleep at 11 AM, it is only physiologically feasible to sleep for 2.7 hours, and therefore he awakens at 1:45 PM. Based on current split sleeper rules he must however wait until 5 PM when 6 hours have passed to be able to start driving again. However he would be completely safe to drive starting at 2 PM, and hence wastes three good and safe driving hours.

These are just two examples, but the interaction of truck driver schedules and circadian sleep-wake physiology produces a myriad of permutations and combinations of best sleep-wake practices given each circumstance. This is where the Hours of Service regulatory paradigm falls apart for NSIR drivers. You just cannot write prescriptive rules to address all these possibilities, or hope to enforce them by current practices. This is why the FMCSA for the sake of highway safety and driver health must open the door to other paradigms. In the words of Thomas Kuhn's seminal book on the "Structure of Scientific Revolutions" this is where normal science must give way to a new paradigm. See Kuhn T. "The structure of scientific revolutions," 3rd Edition ed. University of Chicago Press; 1996, incorporated herein in its entirety by reference.

There are two realities that must be faced in any regulation of trucker duty and rest hours. First, the US economy and transportation system operates 24/7 and requires truckers to pick-up and drop-off loads at every hour of the 24 hour day. Second, the fundamental organization of the human sleep-wake cycle is incompatible with the fair enforcement of a simple prescriptive Hours of Service paradigm, especially for the NSIR driver. The NSIR driver therefore needs greater freedom to obtain his sleep whenever it is most physiologically and operationally feasible to do so.

4. The Need for Flexible Sleep Management II: Individual Differences in Sleep Physiology and the Circadian (Biological) Clock Mean that Drivers Cannot all be Treated Identically.

The interaction of the homeostatic and circadian contributions to sleep already make the situation complex enough, without considering some other factors that make prescriptive fixed Hours of Service rules excessively difficult to design or enforce for the NSIR driver. People are individually different in their circadian sleep wake physiology and one size therefore does not fit all. Three of these factors (time zones, genetic differences and age) are described more fully below, these factors making flexible sleep strategies much more desirable than fixed HoS rules.

Factor 1: Time Zones

Figure 4:
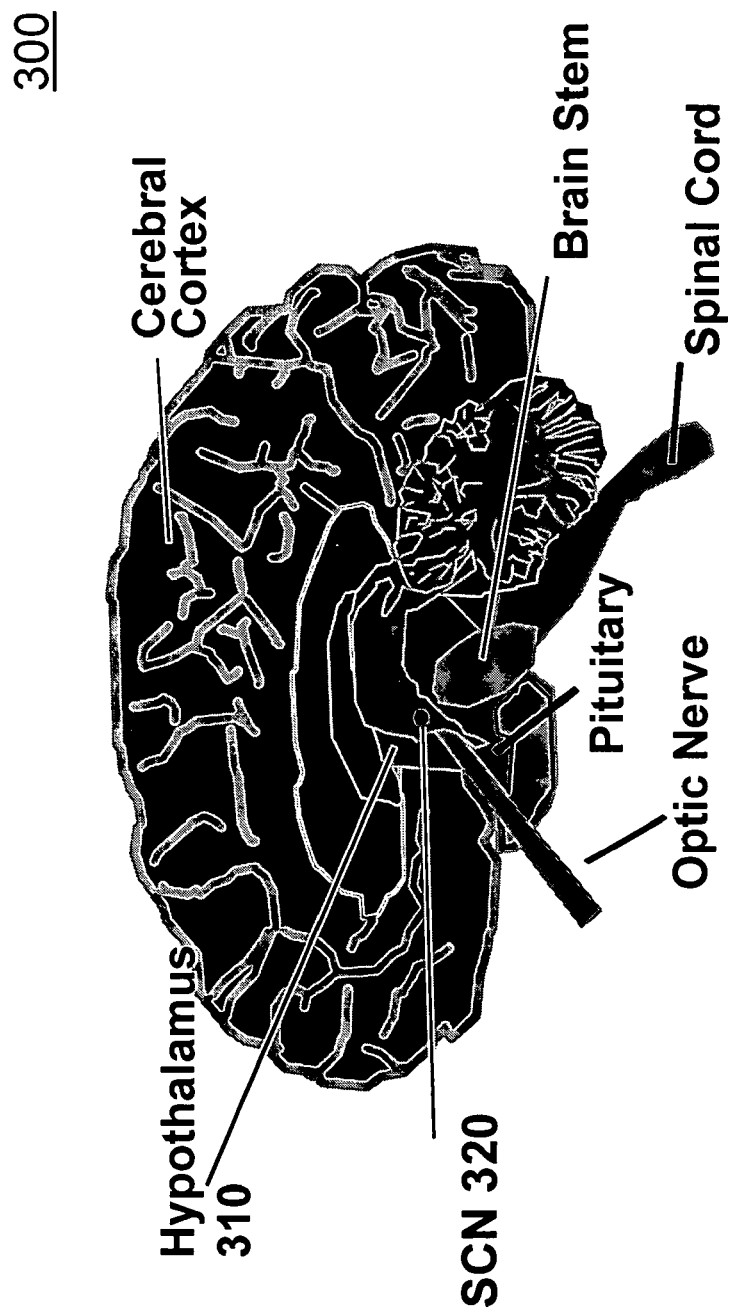
FIG. 4 contains an illustrative view of a brain having a suprachiasmatic nucleus (SCN).

Discussed above are circadian factors largely based in terms of time of day. However, it is not the clock time on the wall that determines the daily biological cycles of sleepiness and alertness, but instead these cycles are timed by a biological clock in the person's brain 300 as illustrated in FIG. 4, located in the suprachiasmatic nucleus (SCN) 320 of the hypothalamus 310 and commonly called the "circadian pacemaker". To distinguish this from man-made or geophysical clock time, the time of day according to a person's biological clock is called the "circadian phase."

Hence if a truck driver has just driven to New York from San Francisco, his circadian phase may still be close to the time zone from where he came, because the human biological clock only adjusts slowly to a new time zone. This is equivalent to the phenomenon known as jet-lag. Unless a shift occurs in circadian phase, the timing of that driver's daily peaks of sleepiness will occur 3 hours displaced with respect to local Eastern time, but close to the accustomed hour according to Pacific time. The circadian phase of an individual is fairly stable, shifting only slowly when adjusting to a new time zone, with the rate depending on how much the driver is exposed to bright daylight at the appropriate times of day to effect a phase-shift. See Moline M L, Pollak C P, Monk T H, Lester L S, Wagner D R, Zendell S M, Graeber C, Salter C A, Hirsch E. "Age-related differences in recovery from simulated jet lag," Sleep 1992; 15(1): 28-40, incorporated herein in its entirety by reference. See also Czeisler C A, Kronauer R E, Allan J S, Duffy J F, Jewett M E, Brown E N, Ronda J M. "Bright light induction of strong (type 0) resetting of the human circadian pacemaker," Science 1989; 244:1328-33, incorporated herein in its entirety by reference. But if the driving has been accomplished largely at night, phase shifting may not have occurred. So without knowing all this for an individual NSIR driver, he cannot be reasonably requested to operate by rigid HoS rules. Merely keeping his log book on the home time zone schedule does not solve the problem. A similar shift in the timing of circadian phase occurs in people who customarily work and sleep at a different time of day from the majority of the population. Thus habitual nighttime work and daytime sleep will result in a gradual partial phase adjustment of the circadian timing of sleepiness. A person's circadian phase, and his consequent pattern of maximum sleepiness and alertness will be shifted to later or earlier hours, as compared to someone who habitually sleeps at night and works during the day.

Factor 2: Inter-individual Genetic Differences in Circadian Sleep-Wake Physiology There are significant inter-individual differences in sleep and napping characteristics, such rigidity/flexibility of sleeping habits, sleep length or morningness/eveningness. These intrinsic differences are caused by differences between individuals in the properties of their circadian clock. See Aeschbach D, Matthews J R, Postolache T T, Sher L, Giesen H A, Jackson M A et al. "Differences in the timing of the circadian rhythm of plasma cortisol between short sleepers and long sleepers," Sleep 1999; 22(Suppl):S141-S142, incorporated herein in its entirety by reference. See also Duffy J F, Rimmer D W, Silva E J, Czeisler C A. Correlation of intrinsic circadian period with morningness-eveningness in young men. Sleep 1999; 22(Suppl):S92, incorporated herein in its entirety by reference.

Some of these inter-individual physiological differences are associated with a differing degrees of tolerance to night or shiftwork. See Costa G, Lievore F, Casaletti G, Gaffuri E, Folkard S. "Circadian characteristics influencing interindividual differences in tolerance and adjustment to shiftwork," Ergonomics 1989; 32:373-385, incorporated herein in its entirety by reference. See also Akerstedt T. "Psychological and psychophysiological effects of shift work," Scandinavian Journal of Work, Environment & Health 1990; 16 (suppl 1):67-73, incorporated herein in its entirety by reference. Radosevic-Vidacek B, Vidacek S, Kaliterna L, Ravlic M, Lalic V, Prizmi Z. "Interindividual differences in tolerance to shift work and characteristics of shift workers: relation between the quality and duration of sleep and certain worker characteristics," Arh Hig Rada Toksikol 1992; 43(3):227-36, incorporated herein in its entirety by reference, examined the relationship between sleep and various worker characteristics in 604 people on rotating shifts. The results showed individual characteristics, including neuroticism, rigidity/flexibility of sleeping habits, accounted for 48% of the inter-individual differences in sleep quality.

To illustrate the importance and relevance of individual differences, one particular individual sleep characteristic, a person's chronotype, is discussed. The chronotype describes a person's tendency to morningness or eveningness. Individuals vary considerably in their orientation to day and night on a morningness-eveningness scale. Morning types tend to rise early and they feel and perform best during the morning hours. Evening types tend to rise late in the morning and they feel at their best late in the evening. It has recently been shown that these characteristics are genetic in nature, and independent of age, sex and ethnic heritage. Katzenberg D, Young T, Finn L, Lin L, King D P, Takahashi J S, Mignot, E. "A CLOCK polymorphism associated with human diurnal preference," Sleep 1998; 21(6): 569-576, incorporated herein in its entirety by reference.

Taillard et al. and Ischihari et al. showed that eveningness was associated with a greater need for sleep, shorter bedtimes on workdays, longer recovery sleep on weekends, and a more irregular sleep-wake pattern. See Taillard J, Philip P, Bioulac B. "Morningness/eveningness and the need for sleep," Journal of Sleep Research 1999; 8(4):291-295, incorporated herein in its entirety by reference. See also Ishihara K, Miyasita A, Inugami M, Fukuda K, Miyata Y. "Differences in sleep-wake habits and EEG sleep variables between active morning and evening subjects," Sleep 1987; 10(4):330-342, incorporated herein in its entirety by reference. Torsvall and Akerstedt demonstrated that morning types had longer sleep length than evening types during days with morning shift, while the opposite was true for afternoon and night shifts. The study also showed differences in shift-related napping behavior between the two groups. See Torsvall L, Akerstedt T. "A diurnal type scale. Construction, consistency and validation in shift work," Scandinavian Journal of Work, Environment & Health 1980; 6:283-290, incorporated herein in its entirety by reference.

The percentage of morning types may depend on age. See Taillard J, Philip P, Chastang J, Bioulac B. "Validation of Horne and Ostberg morningness-eveningness questionnaire in a middle-aged population of french workers.," Journal of Biological Rhythms 2004; 19(1):76-86, incorporated herein in its entirety by reference. It can also depend on work schedule characteristics as self-selection mechanisms may lead to an over-representation of certain chronotypes in populations with certain work schedules (e.g., night and shift work). Truck driver populations are also composed of different chronotypes.

Factor 3: Age

The circadian phase of an individual is influenced by his age. Notably in late adolescence there is a progressive phase-delay in the timing of sleep (increased eveningness tendency), mediated by the timing of nocturnal melatonin release by the pineal gland, which reaches a maximum in males at the age of 20, and then reverses and progressively becomes more phase advanced (increasing morningness tendency) though to the age of 65. See Roennenberg T, Kuehnle T, Pramstaller P, Ricken J, Havel M, Guth A et al. "A marker for the end of adolescence," Current Biology 2004; 14(24):R1038-R1039, incorporated herein in its entirety by reference. This explains why teenagers and college students adopt a sleep-wake pattern that is delayed by several hours from that of their parents. Parenthetically, since operating a commercial motor vehicle is not allowed under the age of 21, sleep research conducted on college age students must be considered with some caution.

Beyond this there are significant changes in the duration of sleep and the circadian timing of sleep during the span of working years. This again contributes to individual variation in sleep patterns and characteristics which make "one size fits all" regulations inappropriate.

In sum, inter-individual differences in sleep and circadian characteristics because of factors such age and genetically inherited traits are an important source of variation. These argue for the allowance of more flexible work-rest rules for NSIR drivers than are currently allowed under Hours of Service regulations.

5. The Need for Flexible Sleep Management III: Naps Should be Encouraged and Not Penalized by a 14-hour On-duty Clock When sufficient sleep cannot be obtained at the ideal time, naps can be a very effective and useful tool to promote safe, alert driving. Extensive research has been conducted which demonstrates the benefits of naps. However, there are two barriers to using naps effectively under the current fixed HoS regulations:

a) Split sleeper rule complexity
b) Disincentives to take brief naps

Split Sleeper Rule Complexity

Although rest periods shorter than 10 hours are allowed by the split sleeper exemptions of the current HoS, they are encumbered by significant restrictions that may limit their effective use.

In order for a workday to be extended beyond 14 hours following a nap in the sleeper, the final stretch of work must be followed by a period of time in the sleeper that sums with the earlier nap to equal ten hours. Drivers are not allowed to be logged off duty for this final rest, they must be logged in the sleeper berth. In theory, this could lead to the awkward situation of a driver finishing a run back home, but being forced to spend a night in the sleeper parked in his driveway rather than in his own bed, in order to comply with the split sleeper exemption.

The problem of being required to spend the nap periods in the sleeper means that drivers would also be forced to change their schedules and plan for trip endings to avoid the situation illustrated in the situation above. Drivers on multi-day trips who regularly take split sleeper berth rest periods would have to calculate their driving so that the trip would not end after an odd number of trips into the sleeper.

One particularly confusing element of the split sleeper provision revolves around enforcement. In situations where a driver's logs were being checked after a nap in the sleeper but before the second half of the sleep period, a driver's legality or illegality would depend upon his intentions. For example, if a driver loaded for 3 hours, drove for 6 hours, then logged in the sleeper for 2 hours, then drove another 4 hours before stopping to be inspected, this driver may or may not have been driving illegally. At the time of the inspection, the driver's day would have been 15 hours long, with two of those hours spent napping. This means that as long as the driver stops driving within the next hour and enters the sleeper for at least 8 hours, he would have utilized the split sleeper berth legally. But if he does not meet both of these conditions, he would be in violation of the regulations from the moment he passed the 14 hour mark, including at the time of inspection. It is unreasonable to expect enforcement officers to anticipate whether or not drivers like this were intending to stop and sleep or to break the rules in order to determine if they are in violation.

Disincentive to Take Brief Naps

While rest periods of 2 or more hours can be used as part of the split-sleeper option, provided all the above complex conditions are met, there is a disincentive for truck drivers to stop for less than two hours for a brief nap. In this case the 14-hour on duty clock does not stop, so if the driver is concerned about running out of time on the 14 hour daily clock he may choose not to stop, even if he is feeling sleepy.

Many of the published studies on napping have been performed under conditions of sustained sleep deprivation (e.g., 48-72 hours without sleep) and thus, some conclusions about the length of naps may not be directly applicable to the normal day to day duty rest patterns of truck drivers.

However, there is a useful body of research on naps as part of the 24 hour work-rest cycle which shows that short naps of 15 minutes to one hour in length can be very effective:

Horne and Reyner demonstrated that a short 15 minute nap, taken during a 30-minute break in the afternoon, significantly reduced sleepiness and driving impairments during the following hour in a simulator study. See Horne J A, Reyner L A. "Counteracting driver sleepiness: effects of napping, caffeine, and placebo," Psychophysiology 1996; 33(3):306-309, incorporated herein in its entirety by reference. Italian police drivers working shifts around the clock, had significantly fewer traffic accidents when they had a short nap (average length 28-37 minutes) before beginning late evening driving shifts (7 PM to 1 AM). See Garbarino S, Mascialino B, Penco M, Squarcia S, De Carli F, Nobili L et al. "Professional shift-work drivers who adopt prophylactic naps can reduce the risk of car accidents during night work," Sleep 2004; 27(7):1295-1302, incorporated herein in its entirety by reference.

Rosekind et al. tested the efficiency of scheduling a 40-minute period in which a nap was allowed during 9-hour aviation flights. See Rosekind M R, Smith R M, Miller D L, Co E L, Gregory K B, Webbon L L et al. "Alertness management: strategic naps in operational settings," Journal of Sleep Research 1995; 4(Suppl 2):62-66, incorporated herein in its entirety by reference. During this period, pilots napped on average for 26 minutes, which was sufficient to maintain alertness and performance throughout the flight, even during night flights.

Employees working in an industrial plant were allowed to use a napping room for one hour every night between 11:00 p.m. and 3:30 a.m. Vigilance increased after the nap and the employees felt significantly better about their quality of life and the ease of work on the night shift. The study concludes that a short nap (maximum 1 hour) during the night shift is a positive way to counteract the low-level vigilance that occurs during the overnight hours. See Bonnefond A, Muzet A, Winter-Dill A, Bailloeuil C, Bitouze F, Bonneau A. "Innovative working schedule: Introducing one short nap during the night shift," Ergonomics 2001; 44(10):937-945, incorporated herein in its entirety by reference.

In these and many other studies, research has shown that short naps can significantly increase most of the human capabilities related to performance; vigilance, alertness, speed of response, memory, accuracy, judgment and visual acuity.

In sum, the structure of the split-sleeper exemption and the 14-hour on-duty clock of the current Hours of Service regulations discourage the use of brief naps. However, there is a considerable body of science and practical experience which show that brief naps can be a very effective tool to promote alert driving in people who would otherwise become sleepy while driving. The NSIR driver should not be discouraged from taking such brief naps, and the FRISPB system will permit him to do so.

6. Risk-Informed Performance-Based (RIPB) Safety Management Using Scientifically-validated Risk Assessment Systems Offers a Superior Level of Safety Compliance than the Traditional Fixed Hours of Service Compliance Paradigm This invention is based upon an alternative paradigm of safety management, which is generally termed the "Risk-Informed, Performance-Based" (RIPB) paradigm. The principle is that if one measures and monitors the specific risks, then government regulators can require the operators of the regulated industries to focus their attention and creative energy on ways to reduce those specific risks, without prescribing cumbersome rules on the exact interventions by which the safety goal should be met.

The evolution of Risk-Informed, Performance-Based Safety Management

Recent years have seen the evolution of a new regulatory paradigm which replaces deterministic rules. This paradigm focuses on the measurement of risk, so that performance in meeting objective risk reduction goals can be measured and assessed. Managing by performance-based measure is a well-established method of obtaining tangible results in a business as is removing some controls but enhancing accountability (see Hertzberg). See Hammer M, Champy J. "Re-engineering the corporation: a manifesto for business revolution," Harper Business; 1993, incorporated herein in its entirety by reference. See also Rummler G, Brache A. "Improving performance: How to manage the white space on the organization chart," Jossey-Bass Publishers; 1990, incorporated herein in its entirety by reference. See also Herzberg G F, Mausner B, Snydeman B B. "The motivation to work." New York: Wiley; 1959, incorporated herein in its entirety by reference. What is new is applying these concepts to government safety regulations, and allowing managers in the regulated industry the flexibility to find the solutions which achieve safety objectives within their own operations.

The Risk-Informed Performance-Based approach to safety management is probably most advanced in the nuclear power industry, although it has been applied to Fire Prevention, nuclear waste disposal and the design of security and blast mitigation at Federal Buildings. See Federal Register. Vol. 69, No. 115, Wednesday, Jun. 16, 2004/Rules & Regulations "Voluntary Fire Protection Requirements for Light-Water Reactors: Adoption of NFA 805 as a Risk-Informed, Performance-Based Alternative" p. 33536, incorporated herein in its entirety by reference. See also Mackin P C, Russell B, Turner D R, Ciocco, J A. "Implementing risk-informed, performance-based regulations for high-level waste disposal," Paper presented at the Waste Management Symposium, Tucson, Ariz., February-March 2001, incorporated herein in its entirety by reference. See also National Research Council (U.S.) Committee to Review the Security Design Criteria of the Interagency Security Committee. "ISC security design criteria for new federal office buildings and major modernization projects: a review and commentary," Washington, DC: The National Academies Press; 2003, incorporated herein in its entirety by reference. The Nuclear Regulatory Agency has made a significant effort to convert to this method of regulation and it now permeates every aspect of nuclear power safety regulation. As the Nuclear Energy Institute reports:

"In a risk-informed performance-based approach, the NRC establishes basic requirements and sets overall performance goals. The plant management then decides how to reach those goals. Risk-informed, performance based regulation is more sharply focused on safety than the current approach, because resources are applied to plant systems and equipment commensurate to their importance to safety."

See Nuclear Energy Institute. "Nuclear Power Plant Regulation. Executive Summary: Significant Progress Toward a More Objective, Safety-Focused Process," October, 2001, incorporated herein in its entirety by reference.

For example, after working with the National Fire Protection Association (NFPA), the NRC published an NPRM and then a final rule on Jun. 16, 2004 concerning a RIPB program for voluntary fire protection standards for nuclear power plants. This program allowed for fire protection measures that are based on a more realistic assessment of the actual fire hazard in various areas of a power plant than was assumed in the previous requirements.

This alternative results-driven process has now been systematically adopted by the Nuclear Regulatory Commission to regulate the myriad safety aspects of nuclear power plants, placing the responsibility on nuclear plant operators to find the most effective way to get the desired safety outcomes, rather than the NRC writing excessively complex and unmanageable prescriptive regulatory rules which are insensitive to local operating conditions or technology.

Fatigue-Risk-Informed Safety-Performance-Based Management of Truck Drivers

The FRISPB system provides an effective, safe and scientifically-validated solution to the unacceptable daily sleep scheduling dilemma of long-haul irregular route truck drivers and other occupations who work extended or nocturnal hours and have a higher than normal risk of fatigue An important element in the invention is determining the right risk and performance measures. For safety management the most obvious measure might have seemed to be accident rate, but accidents are unpredictable and not sufficiently frequent events (fortunately) to provide a useful measure of the risk of every employee on a month to month basis. Furthermore, implementing management incentives based on reduction in accident or injury rates may lead to an under-reporting of accidents, in part because this encourages managers to devise incentives for employees not to report events or injuries. See Geller E. S. "The psychology of safety handbook," 2nd ed. Lewis Publishers; 2000, incorporated herein in its entirety by reference.

For this FRISPB approach to be effective, the managers of trucking fleets need performance measures that provide much more immediate feedback about the work-rest scheduling practices than the relatively infrequent incidence of accident events. By using a fatigue risk score in a FRISPB safety paradigm gives drivers, dispatchers and managers the incentives to address some of the most important causes of driver sleep deprivation, and therefore the risk of fatigue-related highway accidents.

An expert system has been developed and validated to assess driver sleep deprivation and calculate a fatigue risk score, and has been validated for use in FRISPB trucking operations, and is described below.

The main ingredients of the FRISPB safety management program for qualified truckload carriers include the following:

1. The training of drivers, dispatchers and managers on Flexible Sleep Management rules, how to interpret fatigue risk scores, how to adjust work-rest schedules to minimize risk, and related alertness management techniques.
2. A process to capture data on work-rest patterns and/or sleep data from truck drivers, and a mechanism to objectively verify work-rest patterns and/or sleep data using telematics (e.g. Electronic Onboard Recorders, GPS systems, engine ECM data downloads).
3. A scientifically-validated expert system to assess sleep deprivation related fatigue risk for each truck driver based on the work-rest pattern and/or sleep data of the driver over the prior day, week or month.
4. A process to provide a fatigue risk score to each driver and to his dispatchers and managers, so that they are "Fatigue-Risk-Informed".
5. A Safety-Performance-Based system to evaluate on an ongoing basis each driver's success at minimizing his fatigue risk score.
6. An ongoing commitment by the trucking carrier to maintain a continuous improvement process that seeks to control driver fatigue risk.

Figure 5:
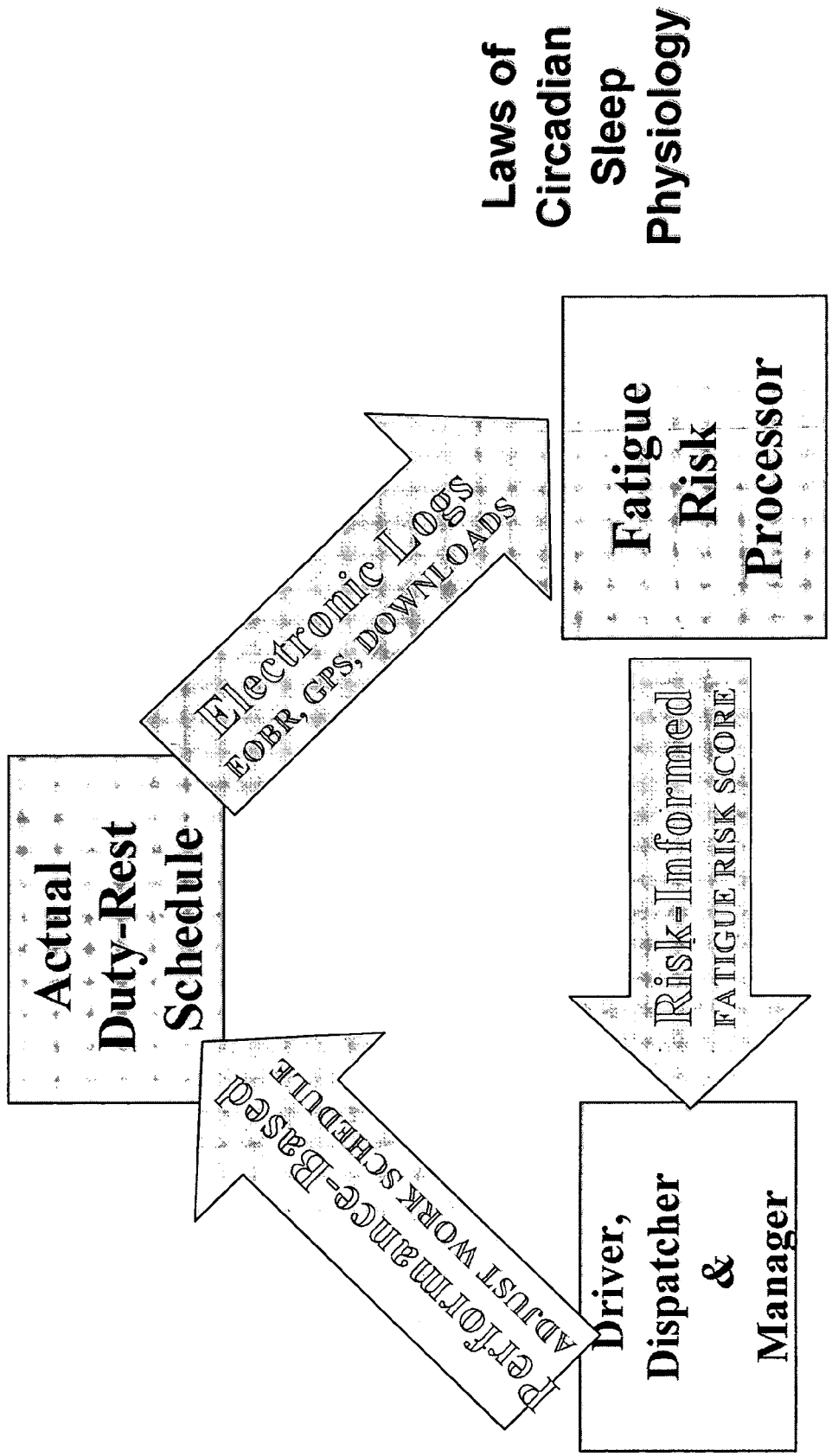
FIG. 5 contains a flow diagram illustrating the steps used to apply a Fatigue-Risk-Informed Safety-Performance-Based (FRISPB) paradigm to truck driver sleep management, according to an embodiment of the present invention.

FIG. 5 contains a flow diagram illustrating the steps used to apply a Fatigue-Risk-Informed Safety-Performance-Based (FRISPB) paradigm to truck driver sleep management, according to an embodiment of the present invention In FIG. 5, a fatigue risk score for each driver is calculated from his current work-rest pattern and/or sleep data and provided to each driver and/or his manager and dispatcher so they are "Fatigue-Risk-Informed." The driver, dispatcher, and/or manager in a scheduled operation are then held accountable to meet a performance-based risk standard by adjusting the driver's future work-rest patterns which then are recalculated to track progress against meeting fatigue risk management objectives.

The application of FRISPB to truck driver sleep management is illustrated in FIG. 5. Information on the actual truck-driver work-rest pattern and/or sleep data are continuously captured from driver logs or in this case electronically using telematics and entered into an Expert System for calculating fatigue risk in truck drivers. A "fatigue risk score" for each driver in the fleet is provided to the driver, his dispatcher and the operations and safety managers making them "Fatigue-Risk-Informed". Training programs are provided to these individuals to educate them in the principles of driver Flexible Sleep Management and the "Safety-Performance-Based" standards of Fatigue score management. Based on the training and the repetitive feedback from the Fatigue Scores, the driver seeks to minimize his Fatigue Score by adopting flexible sleep management practices, and is monitored and is held accountable to these "Safety-Performance-Based" standards by his dispatchers and managers.

This Fatigue-Risk-Informed Safety-Performance-Based approach to work-rest regulation and fatigue management enables drivers, dispatchers and managers to make safety conscious operational decisions while having sufficient flexibility to balance the specific business needs of their operation (e.g. optimization of customer service, minimization of operational costs) and therefore stay competitive in the marketplace. At the same time they have the incentive to address some of the most important causes of driver sleep deprivation, and therefore of fatigue-related highway accidents.

In addition, because this FRISPB process is automated and documented, it reduces the burden of compliance enforcement and log book inspections by the states. The focus of FRISPB compliance is shifted from input parameters (Hours of Service) to output parameters (fatigue risk score and accident risk) which is where the true burden of safety management should lie.

Next, the abovementioned Flexible Sleep Management (FSM) rules are described under which the drivers would operate to allow them the necessary flexibility to adjust their sleep to reduce sleep deprivation risk. Following this discussion, the development and validation in trucking fleets of an expert system, referred to as a Circadian Alertness Simulator or CAS, is described, which provides a fatigue risk score for each driver so that drivers and their managers can be "Fatigue-Risk-Informed."

7. Flexible Sleep Management (FSM) Rules Minimize the Risk of Sleep Deprivation by Allowing Drivers the Flexibility to Stop for Sleep when they are Tired and Drive when Alert Within the framework of any FRISPB management system there needs to be considerably greater latitude and responsibility given to the regulated operator to find his own solutions to minimize the defined risks. Flexible Sleep Management rules are needed to allow truck drivers to work and rest on whatever schedules optimize their ability to obtain restful sleep, rather than following prescriptive HoS rules that may defeat this sleep deprivation risk-management goal.

Defining the Driver Population for Flexible Sleep Management Rules

There are many flaws to installing a one-size-fits-all HoS regulations in an industry where drivers operate under an enormous variety of schedules to service many different types of customer needs.

The population of truck drivers most adversely affected by the current HoS regulations are the NSIR drivers. By definition a driver who is a member of this population:

1) Works on a non-scheduled irregular route operation
2) Is usually away from home more than 7 consecutive days before returning home.
3) Operates an assigned CMV equipped with a (motor home-like) sleeper berth.
4) Principally uses the sleeper berth to fulfill sleep needs on a daily basis.

Unique Features of the NSIR Driver

As the above definition suggests, this is a very specific driver population within the US trucking industry, who drive most of the approximately 677,000 trucks equipped with sleeper berths. See U.S. Census Bureau, 2002 Economic Census, Vehicle Inventory and Use Survey, Issued December 2004, incorporated herein in its entirety by reference. The 2002 numbers are lower than 2005, but there are more trucks out of service today because of the driver shortage, so the number of operated CMVs with sleeper berths is probably about the same. These drivers work and live under unique conditions that other drivers, such as regular route or short haul drivers, do not face. Characteristically this NSIR population drives highly variable routes criss-crossing the country and lives on the road for long periods at a time. For many, their truck sleeper berth is in reality their home.

Unlike regular route drivers who operate on a consistent route on a consistent schedule, an NSIR driver often has a different destination and time demand for every trip. He is given a pick-up location and time, and a delivery location and time which may be several days later.

While often on the road for 1 to 3 weeks at a time or longer, these drivers have considerably fewer off-duty distractions and social obligations than a driver who goes home every night. For example, a long-haul driver does not have to commute from home to work, because his workplace and home are one and the same. By not going home every night like a short haul driver, he does not have to worry about family and friends vying for his time and attention while off-duty.

This is a lifestyle with minimal social distractions to disrupt sleep or determine hours on duty of all types. During the time out on the road the typical NSIR driver does not have the daily obligations or distractions of a local driver or a LTL driver such as family obligations, or other activities that may intrude upon sleep time.

During his daily rest periods the NSIR driver typically sleeps alone, and is not affected by a snoring spouse, a sick or hungry child who wants attention, etc.

While there may obviously be the normal family stresses associated with being away from home, the lack of immediate distractions provides the NSIR driver with more of an opportunity to sleep while off-duty than other truckers. This is why an emphasis needs to be placed on making sure the time a driver goes off-duty is conducive to sleeping (i.e. according to the phase of the driver's circadian rhythms). Only a flexible schedule that can take into account the individual driver's biological clock will allow for a NSIR driver to best utilize his off-duty time.

It is important to understand that when the NSIR driver goes to work it is like a total commitment to a mission for several weeks, without daily family and social activities. After the trip, he then spends an extended period at home. This is quite unlike the lifestyle of other truck drivers who return home most nights. Closer analogies to the NSIR lifestyle are:

Off-shore oil rig workers who fly out to a distant rig for 2-4 weeks at a time and work 12 hour shifts every day, 14 to 28 days straight.

Merchant marine crews who take a voyage lasting several weeks at sea, working a 4 on 4 off watch schedule continuously for weeks on end Astronauts on a space shuttle mission who are on duty 16 hours a day.

Soldiers sent out on a military mission, on duty for 16 or more hours a day, for weeks at a time The advantage the NSIR driver has over other workers assigned to such distant away-from-home missions for several weeks, is that the NSIR driver has his own private "motor home-like" sleeper-berth, can plan his sleep to suit his own body needs and is not required to operate on a fixed schedule determined by the job. If it weren't for the restrictions placed by overly prescriptive HoS rules he could plan out his driving and sleep pattern to meet his needs. But instead the hours-of-service regulations often stop him from driving when alert, and sleeping when tired.

Often the NSIR driver will discover that the HoS rules provide a disincentive to napping when he is tired. For example, if the driver was drowsy and had a 60-minute window to take a nap, he might hesitate to do so because it would eat into his limited driving time on the 14 hour clock. Essentially, because only a nap of two hours or more can be counted toward the sleeper berth provision, there is no incentive for him to take a rest break that is less than 2 hours. This condition will place the driver in an uncomfortable situation where he will either have to drive while tired or nap and risk being in violation later in the day. To avoid these situations, NSIR drivers needs more flexibility to meet their unique work and sleep demands than other drivers.

The Basic Principles of the Flexible Sleep Management (FSM) Rule

To help NSIR drivers best deal with their unique sleep and alertness challenges, a Flexible Sleep Management (FSM) Rule is required. Once drivers are appropriately educated on how to use FSM rules to optimize sleep and alertness, and recognize the problem of fatigue, they can operate with increased safety.

Furthermore, a FSM Rule would increase safety on the road by more thoroughly addressing the factors that cause sleep deprivation fatigue than the current regulations. It would accomplish this by recognizing that the causes of sleep deprivation are more complex than simply reducing driving hours and mandating off-duty time. It would educate drivers that there are numerous other factors that play a key role in determining alertness and drowsiness levels.

Using the basic principle of the FRISPB paradigm, superior safety results are obtained by:
1. Defining the safety goal (i.e. minimizing sleep deprivation fatigue risk).
2. Giving the operator (the NSIR driver) the training on how to achieve the goal.
3. Providing the operator the flexibility to apply his own creativity and experience to achieving the goal, unencumbered by excessively prescriptive rules.
4. Measuring the operators performance against results and holding the operator accountable for achieving the safety goal As described above, the FRISPB paradigm has seven layers of protection to safeguard the safety and health of NSIR drivers operating under the FSM rules. These include:
1. Selection of volunteer NSIR drivers, according to an established standard, and their retention in the program only with management approval.
2. Special training of drivers on circadian sleep and alertness physiology, flexible sleep management rules and maintaining good health on a truckload driver lifestyle, with testing to establish their personal sleep personality, and subject matter testing to ensure they are qualified for the Flexible Sleep Management program.
3. The best day-to-day judgment of a qualified, trained and monitored driver on when to obtain his best quality rest and sleep.
4. Ongoing electronic monitoring to objectively confirm work-rest pattern and/or sleep data using telematics (GPS, ECM download etc).
5. Ongoing fatigue risk assessment of each driver using a scientifically-validated expert risk assessment system, and regular (e.g. weekly or monthly) feedback of each driver's individual fatigue risk score to him, his dispatchers and managers.
6. Management oversight which holds drivers accountable for maintaining safe fatigue risk scores.
7. Conformance with Federal Motor Carrier Safety Administration Section §392.3 which prohibits the NSIR driver from driving while fatigued and prohibits management from requiring him to drive while his alertness is impaired.

The Flexible Sleep Management (FSM) Rules
1. The Flexible Sleep Management Rules strip away the sometimes arbitrary and capricious complexity of the HoS regulations for the NSIR driver down to the following basic requirements: Drivers must take a minimum of 10 hours rest in each consecutive 24 hour period.
2. Each driver is responsible for avoiding sleep deprivation on a daily basis. This is facilitated by allowing him to be in complete control of his sleep time throughout each day (i.e. 24-hour period). He may split his off-duty period rest increments to best meet his own individual sleep needs within a minimum of 10 aggregated off-duty hours. Rest breaks must exceed 15 minutes to count towards aggregated off-duty time.
3. Each trip assignment will have to be documented that enough time is allowed for adequate off-duty time and legal travel time to complete the assignment.
4. The NSIR driver would be limited to a maximum, aggregate non-consecutive 14 hours on-duty time each day.
5. As an exception in some cases, a driver may extend his duty-time to 16 hours to reach home or drop off a load not more than twice a week, provided that the reduction in off-duty time after dropping off a load is paid back by an equal amount of extra off-duty time spread over the next two days. As an example, if a driver is on duty 16 hours in one day, he must take 11 hours off duty each of the next two consecutive days. This situation provides ample off-duty time over the next two days for any recovery needed to eliminate any sleep deficit incurred and maintains the integrity of the 24-hour cycle.
6. Safety and driver health objectives will be assured using a scientifically-validated "Fatigue-Risk-Informed Safety-Performance-Based" expert fatigue risk monitoring system, which has been shown to significantly reduce truck accidents, injuries and driver turnover.
7. Instead of needlessly taking excessive off-duty time while away from home, the driver would be able to aggregate that unneeded time and use it to spend more consecutive time off-duty at home by accruing 24 consecutive hours off-duty for each 7 days he is away from home. NSIR drivers would not be required while on the road away from home to stop driving after 60 hours (which results in an excessive 15.42 average hours off-duty a day) or take a 34 hour break (which results in daily average off-duty time of 12 hours a day), each of which may be excessive to his sleep and alertness management needs when he out alone on the road.
8. No distinction would be made between off-duty and sleeper time. Sleeper time and off-duty time would be combined into one and be shown as off-duty status on the log.
9. On-duty and driving time would be combined with on-duty status and show as on-duty on the log. Therefore, the log would have only two duty status categories: off-duty and on-duty times. Since off-duty time is the controlling factor for alertness, only supporting data to show off-duty time would be necessary.
10. Drivers would be assigned CMVs equipped with sleeping accommodations (exceeding Section §393.76 specifications[2]) throughout his tour of duty and throughout the extended period away from home.
11. Participation in the Flexible Sleep Management option is voluntary by the driver.
12. If the carrier believes the driver is not suited for this option, he may take the driver out of this option.

Justification of Flexible Sleep Management (FSM) Rules:

These provisions reveal a philosophical difference between the current HoS regulations and the proposed FSM rules. Namely, the current hours-of-service rules try to limit a driver's options, while FSM rules seek to expand them within a protected framework. Flexible Sleep Management subscribes to the notion that a trained and qualified individual knows better when they are drowsy than does a rule. Thus the FSM rules give drivers the ability to sleep while tired and drive when alert while also setting strict upper limits to ensure no one abuses their driving privileges.

Each element of the FSM rules will now be described.

24 Consecutive Hours Equals One Day.

By defining 24 consecutive hours as a day, the FMS rules do not allow the NSIR driver to be on-duty at any time later than 14 hours since the end of his last rest period (except for the special circumstance of the 16-hour extension). These rules thus provide extra protection than either the old or the new HoS regulations, which permit unlimited duty hours after driving is completed for the day.

Minimum of 10 Hours Off-duty Required Each Day.

FSM is consistent with the current HoS regulations by requiring a mandatory off-duty time per day of ten hours. A ten-hour off-duty period provides enough time over a 24-hour period to obtain the sleep that is necessary to maintain adequate alertness. Additionally, 10-hours provides time for a NSIR driver to address other off-duty needs beyond sleeping. These other needs include things like eating, showering, and personal time (i.e., phone calls, television, etc.).

Driver Decides the Length of Off-duty Periods or Number of Off-duty Periods Per Day Which Comprise the 10 Hours Off-duty Time Requirement Unlike the current regulations, the FSM rules would allow a driver to take as many off-duty periods as he wanted as long as the sum of all the off-duty periods were greater than or equal to 10 hours within a 24-hour period. By allowing the driver to take his off-duty time at anytime, he can stop and nap if he is tired without having to worry about HoS rules or undertake complex arithmetic to see if he is legal—hardly something a driver should be asked to worry about when he is sleepy. Under the current HoS rules there is a major disincentive to stopping for less than 2 hours because it would not count towards the sleeper berth provision. By removing the split sleeper berth regulation for NSIR drivers, they would be free to base the frequency and the duration of their rest periods on their sleep needs, instead of basing it on compliance with the arbitrary consequences of HoS regulations.

Once Per Week Extension to 16 Hours On-duty

By providing this emergency provision the NSIR driver can better avoid frustrating situations where he runs out of daily duty hours less than two hours travel away from home or delivery of a time critical load. The provision of additional recuperative rest allows him to recover from any potential sleep loss.

The Question of Weekly Limits

The current Hours of Service regulations provide for a 34-hour restart rule which allows a driver who is approaching the 60 hours driving time in 7 days or 70 hours in 8 days limits, to go off-duty for 34 hours, and then restart his 7-day or 8-day clock. This has the effect of establishing the maximum on-duty time of 84 hours per seven day week.

For the extended mission away from home jobs (off-shore oil rigs, marine voyages etc), as discussed above, 84-hour workweeks are the norm, since the workers wish to accumulate and take their off-duty time with their families when they get home. In fact when traveling to and from the distant job is included at the beginning and end of the mission, the average work-week significantly exceeds 84-hours. Despite the demanding nature of the off-shore rig jobs, the safety and health risks of the 84-hour work weeks are viewed as acceptable. In fact, the risk of traveling as a passenger in the helicopters to and from the off-shore oil rig is 60-fold greater than the risk of actually working 84-hours per week on the rigs See Personal communication, UK Health and Safety Executive, incorporated herein in its entirety by reference.

The problem with weekly limits, over and beyond the daily 14-hour limit whether it be 60 hours in 7 days, 70 hours in 8 days, or the 34-hour restart provision is that the NSIR driver can be kept away from his home, stuck in a remote location for extended period of time living in his sleeper berth. Extra weekly enforced off-duty time may have minimal value for him for, over and above the 10 hours off-duty per day, especially if he has taken proper advantage of the FSM Program to ensure he is fully rested. In this sense placing arbitrary weekly limits goes against the principle of the FRISPB process and the FSM rules.

In addition, there are significant populations of truck drivers who currently operate under relaxed or no effective weekly limit of hours on duty. For example:

Under Title 13, the California Code of Regulations, 34501.2 permits intrastate truck drivers who are bringing farm products from the field to the first point of processing or packing to drive for up to consecutive 16 hours on duty, or 112 hours on duty in 8 days. These truck drivers use the public highways within a large and highly populated state. Furthermore if there is inclement weather, natural disaster or adverse economic conditions these upper limits on driving hours may be waived for an 8-day period (CCR 34501 (c) (2)).

Alaska truck drivers under 395.1 (h) (1) can drive for 15 hours and be on duty for 20 hours in a day, after 10 hours of off-duty rest.

A FMCSA pilot program grants an exemption from the weekly hours-of-service restrictions for drivers of commercial motor vehicles (CMVs) making home heating oil deliveries that occur within a 100 air-mile radius of a central terminal or distribution point, during the winter months. States also can grant temporary exemptions under Title 49 CFR Part 390.23 from the weekly restrictions in their intrastate hours-of-service regulations for the transportation of home heating oil during the winter months. New York, Massachusetts (see for example), Connecticut, Rhode Island and other states granted such exemptions in 2005.

Western Australia truck drivers operate without hours of service regulations but they do operate under the Western Australia Occupational Safety Code of Conduct. See Government of Western Australia—Commission for Occupational Safety and Health. "2004 Code of Practice: Fatigue management for commercial vehicle drivers," incorporated herein in its entirety by reference. This code of conduct states "So far as practicable, the work time for solo drivers must not be more than 168 hours in any 14 day period. The 14 day period must include at least two periods of 24 continuous hours of non-work time. This means that the 168 hours will usually be spread over 12 days. It is acceptable to work according to a 28 day schedule instead of the 14 day arrangement described above. However, this is on the condition that the hours of work time do not exceed 144 hours in any 14 day period within the 28 days. To comply with requirements for 28 day schedules, drivers must have at least four periods of 24 continuous hours of non-work time in any 28 day period. The hours of non-work time may accumulate but they must be taken in minimum 24 hour lots. They cannot be split into half days. The 28 day roster means that a driver could work for 24 out of any 28 days and there could be up to 24 days of work before a driver has days off. If a driver works every day for 24 days, the driver must stop driving the commercial vehicle for four continuous days". Studies show that under this scheme 11% of drivers exceed 90 hours work in a given week. See Hartley L, Arnold P, Penna F, Hochstadt D, Corry A, Feyer A-M. "Fatigue in the Western Australia transport industry. Part two: The drivers' perspective." 118 ISBN 0 86905-535-6, 1-70. 1996. Western Australia Department of Transport, Institute for Research in Safety & Transport, incorporated herein in it entirety by reference.

It should be noted that none of these operations with relaxed or no effective weekly limit have the carefully controlled and monitored conditions of the Fatigue-Risk-Informed Safety-Performance-Based program to support the FSM rules for the NSIR driver. We provide in the FRISPB program for seven levels of safety assurance—Selection, Training, Qualification, Monitoring, Risk-Information, Accountability and Compliance—as discussed above. These safety assurances are required in none of these trucking operations discussed above, that have relaxed or no weekly limits.

Nevertheless, health and safety data is available that argues against unlimited duty hours, virtually all of it drawn from other businesses which do not represent the conditions unique to the irregular route truckload driver, with his ever present "motor home-like" sleeping accommodations. There are a number of studies, including industry studies from a broad range of non-trucking 24/7 operations conducted by Circadian Technologies which show that high levels of overtime are associated with increased costs such as worker compensation claims, and health care costs. See Kerin A. "Overtime in extended hours operations: benefits, costs, risks, and liabilities," 2003. Lexington, Mass., Circadian Technologies, Inc, incorporated herein in its entirety by reference. See also Kerin A, Carbone J. "Financial opportunities in extended hours operations: managing costs, risks, and liabilities," 2003. Lexington, Mass., Circadian Technologies, Inc., incorporated herein in its entirety by reference. See also Aguirre A, Kerin A. "Shiftwork Practices 2005," Lexington, Mass., Circadian Technologies, Inc., incorporated herein in its entirety by reference.

However, there are no known studies which cleanly separate the effects of total hours on duty per week from a) the length of daily duty period, and b) the percentage duty time occurring at night. Both of these confounding factors have scientifically documented powerful influences on health and safety risk.

For example, the recent elegant studies of the Harvard Work Hours, Health and Safety Group, which examined the effects of changing the working hours and schedules of junior hospital doctors, showed that doctors working 74-92 hours per week made 20% more medication and critical care errors than doctors working 57-76 hours per week. See Landrigan C, Rothschild J, Cronin J, Kaushal R, Burdick E, Katz J et al. "Effect of reducing interns' work hours on serious medical errors in intensive care units." New England Journal of Medicine 2004; 351:1838-1848, incorporated herein in its entirety by refererence. See also Lockley S, Cronin J, Evans E, Cade B, Lee C, Landrigan C et al. "Effect of reducing interns' weekly work hours on sleep and attentional failures," New England Journal of Medicine 2004; 351:1829-1837, incorporated herein in its entirety by refererence.

However a major contributing factor was that the doctors with higher hours per week accumulated those hours by working shifts of up to 34 hours non-stop, whereas the lower hours per week group never worked more than 24 hours non-stop. In comparison the NSIR drivers under the FSM rules never exceed 14 hours on duty per day—a very different proposition with a much lower safety risk.

Similarly there is published research which has associated increased risks of coronary artery disease in firefighters working 70 hours a week as compared to those working 50 hours a week. See Lusa S, Hakkanen M, Luukkonen R, Viikari-Juntura E. "Perceived physical work capacity, stress, sleep disturbance and occupational accidents among firefighters working during strike," Work & Stress 2001; 16(3):264-274, incorporated herein in its entirety by reference.

In this study, a closer look shows that the excess hours were caused by a prolonged strike with considerable workplace stress, itself a factor for coronary risk. It should also be noted that firefighters characteristically work 24-hour shifts, again bringing in the powerful confounding variable of extended consecutive hours on duty, which is not a factor in the NSIR drivers under FSM rules.

There is no relevant data which points to whether there is a true risk of not placing weekly on-duty hour limits on the NSIR driver in the FSM program beyond the 10-hours per day rest requirement. On that basis it is a judgment call whether it is worth putting arbitrary weekly limits over and above the daily 10-hour rest requirement. Such weekly limits might force a fully rested NSIR driver operating under FSM rules to sit in some remote location with no recuperative value, and potentially undesirable distractions. The theoretical gain from weekly limits might not be worth the actual cost.

Flexible HoS Systems Pioneered in Australia:

The hours-of-service debate is not unique to the American trucking industry. Other countries have tackled the same complexities of driver fatigue while developing their truck driving policies. Among the most progressive hours-of-service program that has emerged from these debates is Queensland, Australia's Fatigue Management Program (FMP).

While examining its Truck Driving Hours Regulations, the Queensland government recognized many flaws of addressing the problem of fatigue solely by restricting hours of service and mandating time off work. Among the main criticisms of this approach were its: lack of flexibility; failure to consider the circadian rhythms of drivers; failure to consider the wide variety of schedules among drivers; poor compliance;

and rigid restrictions that may prevent drivers from reaching better rest facilities only a short distance away. See Hartley L. "Australian initiatives in managing fatigue in transportation," Paper presented at the Insurance Commission of Western Australia Conference on Road Safety, Perth, November 1999, incorporated herein in its entirety by reference.

The Queensland Fatigue Management Pilot (FMP) program is a joint industry and government initiative that provides an exemption from the Road Traffic (Driving Hours) Regulations 1999 for individual trucking fleets, provided they develop and maintain Fatigue Management Program Policies and Procedures to monitor and control the various elements of a fleet's operations that affect driver fatigue. See Laidlaw, D V Ministry for Transport and Urban Planning Declaration under Regulation 5 (4) Exemption from Provisions of Road Transport Act, Mar. 4, 2000, incorporated herein in its entirety by reference. See also "Beyond the Midnight Oil: Managing Fatigue in Transport, House of Representatives Standing Committee on Communication," Transport and the Arts, Parliament of the Commonwealth of Australia, October 2000, incorporated herein in its entirety by reference Among the main tenets of the FMP program was installing education platforms within companies to teach management and drivers about how to identify and manage factors that impact fatigue. These lessons covered such topics as scheduling, driver health, workplace conditions, fitness for duty, time off and recognizing signs of fatigue. By requiring motor carries to demonstrate that had installed fatigue education programs and had met other requirements of the FMP, motor carriers' drivers were allowed more flexibility in their schedules and longer driving periods than drivers of motor carriers who did not adopt to the program.

It is worth noting that since the Queensland Government implemented the FMP in its National Driving Hours Policy in October 1998, the policy has also been implemented in 4 other provinces: New South Wales, Victoria, South Australia, and Tasmania.

Flexible Sleep Management Rule: Enforcement

The enforcement of the Flexible Sleep Management rule is simplified, time saving, and reduces paperwork burdens.

Logs:
1. Automated logging of duty and rest will be permitted.
2. If paper logs are used, the log sheet will show the title: "Flexible Sleep Management Rule."
3. The log book jacket will include the text if the "Flexible Sleep Management Rule" and an example similar to the concurrent log book jackets for both the driver and the roadside inspector to use in identifying and auditing the log at roadside.
4. The log sheet will still cover each 24-hour period—midnight to midnight or noon to noon.
5. There will be two lines only: (1) Off-duty and, (2) On-duty time, instead of four lines. Only off-duty times and locations will need to be shown instead of all entries for all other changes of duty status.
6. Multiple days may be recorded on a single log sheet.
7. The other items required on logs will remain the same.

Roadside Inspections:
Roadside inspectors will only have to examine 48 hours of a driver's logs to determine if the driver has accumulated 20 hours off-duty during the preceding 48-hour period, or up to 22 hours off duty if a driver used the 16-hour exception.

Carrier Management:
1. Companies will be required to provide training on Flexible Sleep Management rules. Training shall include the interpretation of fatigue risk scores, the adjustments to duty and off-duty patterns that reduce Fatigue Risk, and how to recognize signs of drowsiness and how to remain alert while driving.
2. Management must have in place a telematic system (e.g. electronic, GPS, ECM download etc.) that can be used to objectively verify hours the CMV was driven and at rest.
3. Management must have in place a FRISPB protocol using the expert system to assess the sleep deprivation fatigue scores of drivers. A driver who has a high fatigue score will be counseled on how to lower the score in order to lower the risk of a fatigue-related accident. A driver will be expected to make best efforts to minimize their fatigue scores.
4. Management must have in place a verification process to show that drivers were allowed ample time for both on-duty and off-duty time to complete each load. (PUD task or load PUD mission.)
5. Management has the right to remove a driver from this Flexible Sleep Management program if the driver demonstrates he cannot and/or does not satisfactorily manage his rest time and does not comply with the HOS regulations provided in this option and/or submit timely, true and accurate logs.
6. The driver has the right to opt out of this Flexible Sleep Management program if he feels it is not adequately meeting his sleep needs.

Company and Government Auditing:
Auditors will be able to verify on premises:
1. That the company has a Fatigue-Risk-Informed Safety-Performance-Based Flexible Sleep Management program in place, and is complying with its requirements.
2. That the trucks in the program are equipped with a telematic system that can measure if the vehicle was stationary for the required off-duty periods while the driver was on his mission.

In sum, by requiring a minimum of 10-hours off-duty in every twenty-four hour period the Flexible Sleep Management rules for NSIR drivers are compatible with the current HoS regulations. Where the FRISPB regulations differ from the current hours-of-service regulations is in the flexibility they provide NSIR drivers. It allows them to rest whenever they want, for as long as they want, with no disincentive not to do so, and provides for greater opportunities for consecutive days off at home. Furthermore the rules, require all participating drivers to be qualified, to undergo training on sleep management, and to be constantly monitored for their performance in meeting Fatigue Risk goals. In summary, by providing drivers the flexibility to drive when alert and sleep when tired, safety is enhanced among this special population of NSIR drivers.

8. Expert Risk Assessment Systems which Continuously Assess Driver Fatigue Risk Permit Monitoring of Compliance with Flexible Sleep Management Rules The FRISPB methods described herein uses risk assessments to provide "Fatigue-Risk-Informed" information to employees and managers, and to enable "Safety-Performance-Based" objectives to be established and continually monitored.

Since the interrelationships between sleep, circadian rhythms and truck operating schedules are complex, and following simple rules such as the current HoS regulations can yield undesired and unintended results, it makes sense to turn to risk assessment models which can readily calculate the risk fatigue induced by sleep deprivation from any combination of work hours and sleep schedules. There has been a long history of scientific experience in modeling the complexities of circadian sleep-wake physiology. For an example see Moore-Ede M C, Czeisler C A. "Mathematical models of the circadian sleep-wake cycle," New York: Raven Press; 1984, incorporated herein in its entirety by reference.

Describe herein is an example of how risk information can be generated and provided to drivers and managers in a FRISPB safety management process using an expert driver fatigue risk assessment system. An expert system that has been developed and scientifically validated a software program called "Circadian Alertness Simulator" or "CAS" which has been specially adapted to measure the risk of accidents caused by sleep deprivation in commercial truck drivers. See Moore-Ede M C, Heitmann A, Guttkuhn R, Trutschel U, Aguirre A, Croke D. "Circadian alertness simulator for fatigue risk assessment in transportation: application to reduce frequency and severity of truck accidents," Aviation, Space, and Environmental Medicine 2004; 75(3): Suppl A107-18, incorporated herein in its entirety by reference. This CAS expert system to be described as follows is an effective tool to manage FSM rules for the safe operation of trucking fleets, and provide the risk-information which is needed to make FRISPB a viable alternative to the traditional Hours of Service paradigm.

Development of the CAS Expert System

The Circadian Alertness Simulator (CAS) has been developed over the past fifteen years as a practical tool for assessing fatigue risk in the 24/7 workplace, and for reducing the rate of fatigue-related accidents, injuries and deaths at work and on the highway. CAS has been used as a fatigue assessment system in numerous fatigue management projects in the railroad and trucking industry, and has been proven to be an effective tool in employee fatigue reduction programs. Other applications, beyond the scope of this FRISPB application of CAS include work schedule optimization, fatigue-related accident investigation, and employee lifestyle education training CAS simulates alertness and chronic sleep deprivation levels based on actual work patterns. The CAS software includes simulation modules for sleep and alertness prediction and a cumulative fatigue risk score assessment is calculated across multiple days or weeks. It should be noted that there is an essential difference between the alternative modeling strategies of a) predicting minute by minute fluctuations in future alertness levels, versus b) the use of CAS in the FRISPB paradigm to undertake a risk assessment of the probability of accidents caused by fatigue in a group of employees working under a certain work-rest schedule. The reliability of the estimated CAS Fatigue Score is enhanced in the approach used in the FRISPB paradigm, because the fatigue risk score is calculated by combining multiple parameters (see below) and also because the risk is averaged over a period of time (typically a month).

The CAS model is based on the two-process model of sleep regulation where sleep timing and duration is determined by circadian and a homeostatic components, and on the well-established relationships between the circadian factors (phase, period, amplitude), homeostatic factors (sleep and wake duration) and alertness. See Borbely, AA. "A two process model on sleep regulation," Hum Neurobiol 1982; 1:195-204, incorporated herein in its entirety by reference. See also Daan S, Beersma D G M, Borbely A A. "Timing of human sleep: recovery process gated by a circadian pacemaker." American Journal of Physiology 1984; 246:R161-R183, incorporated herein in its entirety by reference. See also Carskadon M A, Dement W C. "Daytime sleepiness: Quantification of a behavioral state," Neuroscience & Biobehavioral Reviews 1987; 11:307-317, incorporated herein in its entirety by reference. The model assumes a superposition of the homeostatic and circadian processes.

For the majority of applications where the precise hours of sleep and wakefulness are not known, the CAS software creates an estimated sleep-wake pattern based on the actual work pattern of the individual (sleep estimation mode). Alternatively in cases where actual data on sleep-wake patterns are available, this pattern can be entered directly into CAS and the sleep estimation algorithm is by-passed. In the sleep estimation mode, the model calculates alertness minute by minute and triggers sleep when alertness reaches a certain lower threshold provided that sleep is not prohibited at this minute (i.e. due to work activity). The model then creates sleep for all following minutes until alertness reaches the upper threshold, or a time when sleep is prohibited due to the work schedule and other constraints (e.g., required pre-work preparation and commuting time). At this time, the activity simulation switches to the awake state and assumes wakefulness until sleep is triggered again. This way, the model generates a complete sleep-wake pattern around any given work pattern.

Based on sleep and alertness measures and the actual work-rest pattern, a cumulative sleep deprivation "Fatigue Score" is calculated for each individual or group of individuals. The cumulative Fatigue Score quantifies overall sleep deprivation risk across a given time period. It is computed as the weighted sum of several output parameters, such as daily sleep duration, percentage time in defined alertness zones during work, duration of episodes with critically low alertness during work, average alertness score, variability of alertness score, hours of duty per week, and number of recovery breaks allowing two consecutive nights of sleep per week. The fatigue risk score ranges from 0 (no fatigue) to 100 (extreme fatigue). It was scaled so that a Monday-Friday 9 AM-5 PM daytime-only work schedule scored a 5, and a extreme schedule of consecutive cycles of 36 hours continuously on-duty and 12 hours rest with 1 day off per week (e.g. as seen in medical interns) scored a 95 on the scale from 0 to 100.

One of the valuable features of the CAS software is a training module that allows the tailoring of the model to specific populations (e.g., employees in certain occupations, industries or sites). In the training process, the free parameters of the algorithms are adjusted based on comparisons of actual sleep/alertness data from large experimental data sets and simulated outcomes. For the current transportation version of CAS, the free parameters of the model were iteratively adjusted in order to best fit an experimental database of over 10,000 days of sleep-wake-work records and alertness data from transportation employees working their normal duties. A "figure of merit function" was calculated to measure the agreement between observed and predicted sleep episodes and between observed and predicted alertness levels, with small values of the merit function representing a close agreement ("good fit"). Using a multidimensional Simplex Optimization Method, the free parameters of the algorithms were adjusted to achieve a minimum in the merit function.

Validation of CAS in Assessing Truck Driver Accident Risk

To test and demonstrate the validity of CAS expert system to assess the sleep-deprivation fatigue risk in truck drivers, it was used to compute fatigue risk from the work-rest data of truck drivers and then correlate this with the actual accident rates and costs of the trucking operation. Specifically, we tested the use of CAS Fatigue Score as a specific risk measure to help reduce fatigue-related accident rates. We found that the use of such a fatigue risk assessment tool significantly reduced the rate and severity of heavy truck accidents.

For such a fatigue risk assessment expert system to have validity and applicability to accident prevention in the trucking industry it must:

1) distinguish between work-rest schedules which are known to induce differing levels of sleepiness in truck drivers,
2) define the statistical distribution of fatigue risk across the wide variety of trucking operations,
3) show a significant correlation between high fatigue scores and accident rates, and
4) show that the rate and severity of truck accidents is reduced when the fatigue score is lowered by modifying driver work-rest schedules using the principles of circadian sleep-wake physiology.

To address these four requirements a study was conducted by the inventors of the present invention to evaluate whether CAS can serve as a scientifically-validated expert risk assessment system for the evaluation of truck driver duty-rest patterns for their Fatigue Risk.

TABLE 1

| Driving Schedule | Schedule Description | Percentage Drowsiness While Driving | CAS Fatigue Score |
|---|---|---|---|
| Steady day | 10 h driving, 9 AM start, 5 consecutive days | 1.49% | 12.65 |
| Advancing night | 10 h driving, 9 AM start on day 1, 2-3 h earlier each day after 5 consecutive days | 4.38% | 47.89 |
| Delaying evening | 13 h driving, 11:30 PM start on day 1, 1 h later each day after 4 consecutive days | 8.82% | 67.50 |
| Steady night | 13 h driving, 11 PM start, 4 consecutive days | 11.61% | 90.50 |
| | | $r = 0.98, p < 0.05$ | |

In Table 1, comparisons were made of the CAS fatigue scores and the percentage of time spent drowsy while driving (from 6-minute-segments of video recordings), based on data published by Mitler et al., as disclosed above, and incorporated herein in its entirety by reference. In the study, four groups of 20 male truck drivers carrying revenue-producing loads were continuously studied while operating on either a) a steady day schedule of 10 hours of driving beginning at 9 AM for 5 consecutive days, b) an advancing night schedule of 10 hours of driving beginning on day 1 at 9:30 AM and advancing 2-3 hours each day for 5 trips, c) a steady night schedule of 13 hours of driving for four consecutive days beginning at 11 PM each day, and d) a delaying evening schedule of 13 hours of driving beginning at 11:30 AM on day 1 and beginning 1 hour later on each of four consecutive days of driving. Video-recording in the cab when the truck was moving was scored by independent expert scorers in consecutive 6-minute segments for signs of drowsiness. For purposes of calculating CAS Fatigue Scores, it is assumed the work-rest schedule of each group would be repeated each week after a two day off-duty period.

Figure 6:
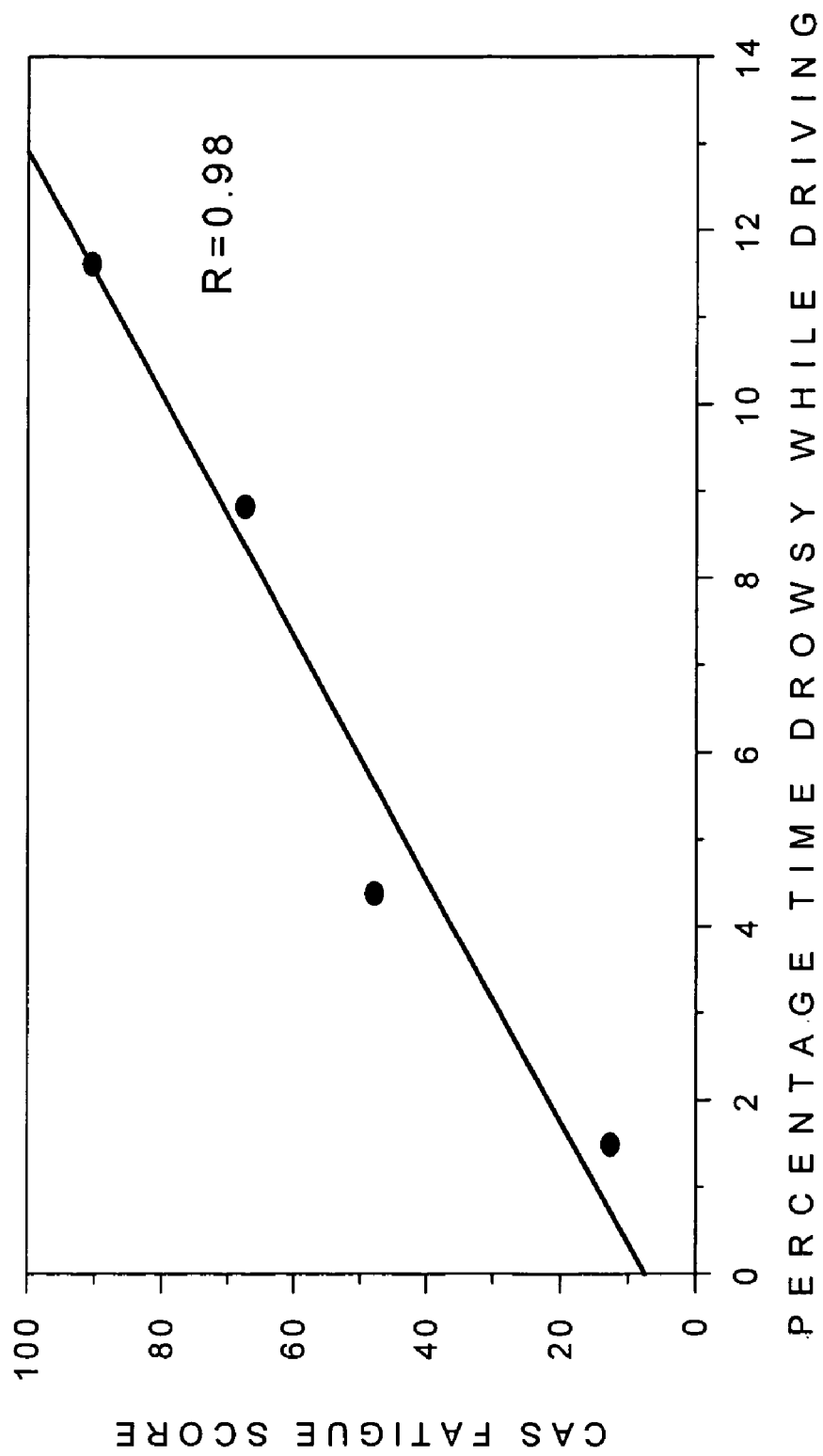
FIG. 6 contains a graph illustrating a correlation between CAS Fatigue Scores shown in Table 2 and the percentage of time that truck drivers are drowsy in a moving vehicle during a work shift.

FIG. 6 contains a graph illustrating a correlation between CAS Fatigue Scores shown in Table 1 and the percentage of time that truck drivers are drowsy in a moving vehicle during a work shift on each work-rest schedule were reported to be drowsy while their vehicles were moving. As shown in FIG. 6, the correlation between Fatigue Scores calculated by CAS from the four truck driver work-rest schedules reported by Mitler and described in Table 1, and the percentage time the truck drivers on each work-rest schedule were reported to be drowsy while their vehicles were moving.

Correlation with Objective Measures of Drowsiness in Truck Drivers

CAS Fatigue Scores were calculated for four distinctly different work-rest schedules where sleepiness level had been measured objectively in groups of 20 truck drivers using continuous facial video-recording within the truck cab while they were driving their vehicles in normal revenue-generating service. Table 1 shows there was a statistically significant correlation (Pearson r=0.98 p<0.05) between the CAS fatigue score and the mean percentage of the 6-minute segments of video recording independently judged to show a drowsy driver by Mitler et al.[24] in each of the four groups of truck drivers. This relationship is plotted graphically in FIG. 6.

From this comparison it can be concluded that there is a linear relationship between the CAS Fatigue Score and the percentage time truck drivers are visibly drowsy while on the road.

Definition of the Statistical Distribution of Fatigue Risk Across Trucking Operations The original scale on the CAS Fatigue Score was calibrated using a scale based on a) workers on a traditional work-rest schedules of Monday-Friday daytime 9 AM-5 PM as a Fatigue Risk of 5 on a 0-100 abscissa scale, and b) junior hospital doctors working 36-hour shifts with 12 hour breaks between them as a Fatigue Risk of 95 on the abscissa scale. The question addressed is what range of CAS Fatigue scores would truck drivers have in their normal revenue-producing work? To accomplish this, driver logbooks were collected for a month from all the 868 drivers (male=852, female=16) from three trucking operations which included less than truck load (LTL), truckload (TL), relay, over the road, local delivery, and sleeper teams located in the eastern, southern and western USA respectively, and entered the data into CAS.

Figure 7:
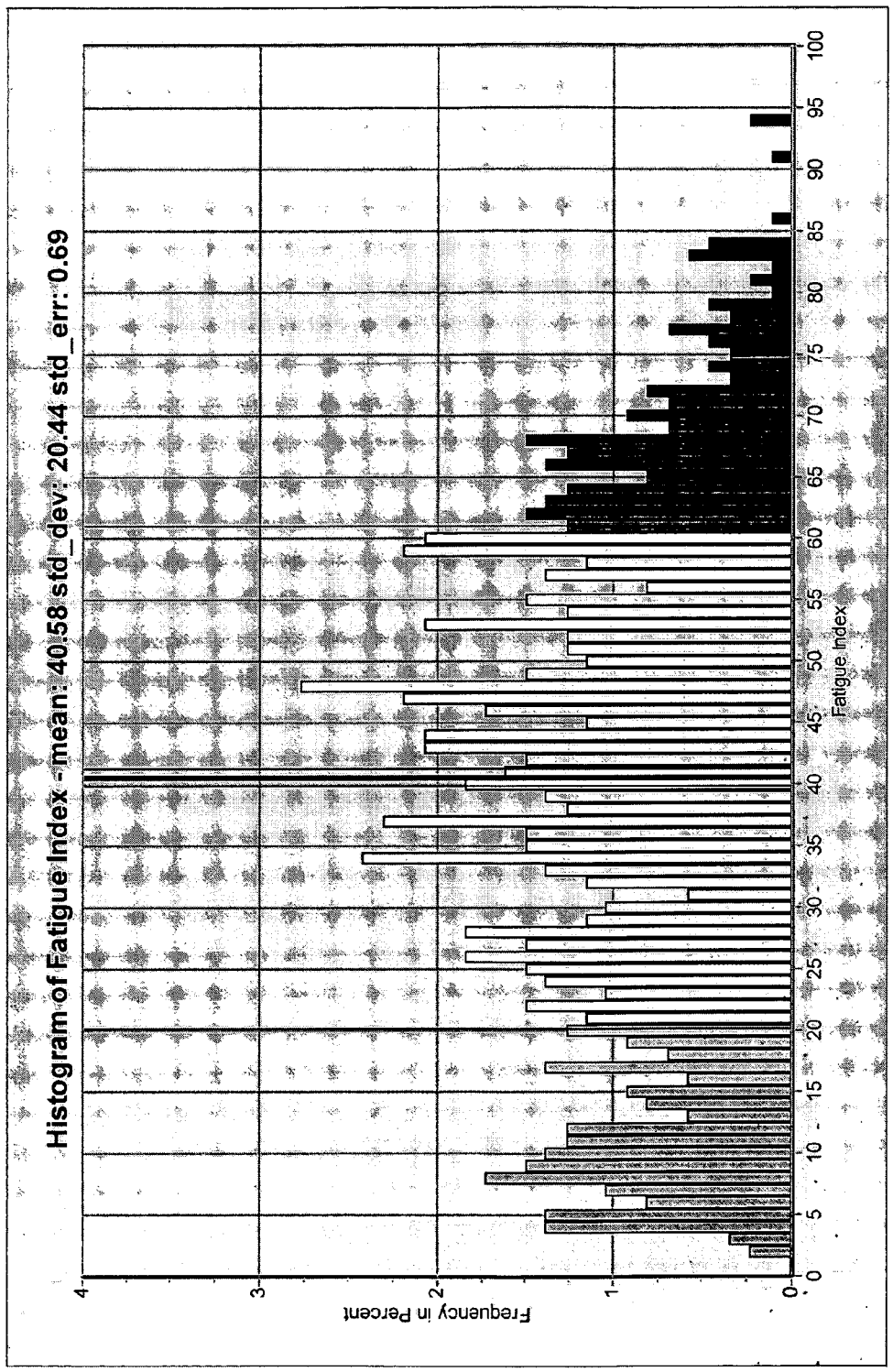
FIG. 7 contains a graph illustrating a frequency distribution of fatigue risk scores for truck drivers.

FIG. 7 contains a graph illustrating a frequency distribution of fatigue risk scores for truck drivers, with 0=very low fatigue level and 100=very high fatigue level. The Frequency distribution of CAS Fatigue Scores for truck drivers was derived from three diverse trucking operations (n=868), provided one month of work-rest data from driver logbooks and this was used to calculate their Fatigue Scores. In particular, FIG. 7 shows the percentage of drivers with each of the possible CAS fatigue scores from 1 to 100. The distribution of percentage drivers shows an approximately normal distribution, albeit somewhat skewed, with a mean fatigue score of 40.58+/−20.4 SD, wherein SD is Standard deviation. In a normal distribution about 68% of the population falls with ±1 SD from mean.

Based on the results shown in FIG. 7, a scale designed to help trucking companies manage the CAS Fatigue Scores for their drivers is defined. As shown in FIG. 7, 81-100 is categorized as high risk (>2 SD above mean), 61-80 is categorized as elevated risk (>1 SD above mean), 41-60 (<1 SD above mean) is categorized as medium risk, 21-40 (<1 SD below mean) is categorized as reduced risk, and 0-20 (>1 SD below mean) is categorized as minimal risk. Using the correlation between video-recorded drowsiness and CAS Fatigue Score shown in FIG. 6, high risk (>80) represented greater than 10% of the driving time spent in a visibly drowsy state, whereas minimal risk (<20) represented less than 2% of the driving time spent visibly drowsy.

Correlation Between Cas Fatigue Scores and Accident Rates

Since the primary purpose of developing the CAS Fatigue Scores was to establish a measure that was sensitive to driver lapse of attention accident risk, we examined the Fatigue Scores in one company all the accident free drivers, and all the drivers with a DOT-recordable accident (fatality, serious injury, vehicle towed away) during a calendar year.

The monthly sets of work-rest logs for all (n=430, 422 male, 8 female) accident-free drivers (mean age: 42 years, range: 23-73) in one trucking operation were analyzed and compared with those from all drivers (mean age: 37 years, range: 22-61) from the same operation involved that year in "DOT recordable accidents" (n=24) and with all drivers (mean age: 33 years, range: 22-53) involved that year in "severity accidents" with insurance claims in excess of $20,000 (n=11). The CAS Fatigue Score for accident-free drivers averaged 42.1±1.0 SEM, versus a mean fatigue score of 62.5±3.6 SEM for drivers involved in DOT recordable accidents and mean fatigue score of 63.3±4.0 SEM for drivers involved in severity accidents The higher fatigue scores were seen both in drivers with DOT recordable accidents, and in drivers involved in severe accidents, indicating a significant relationship between fatigue score and DOT recordability ($\chi 2=170.1$, df=2, p<0.001) and accident severity ($\chi 2=12.6$, df=2, p<0.005).

Figure 8:
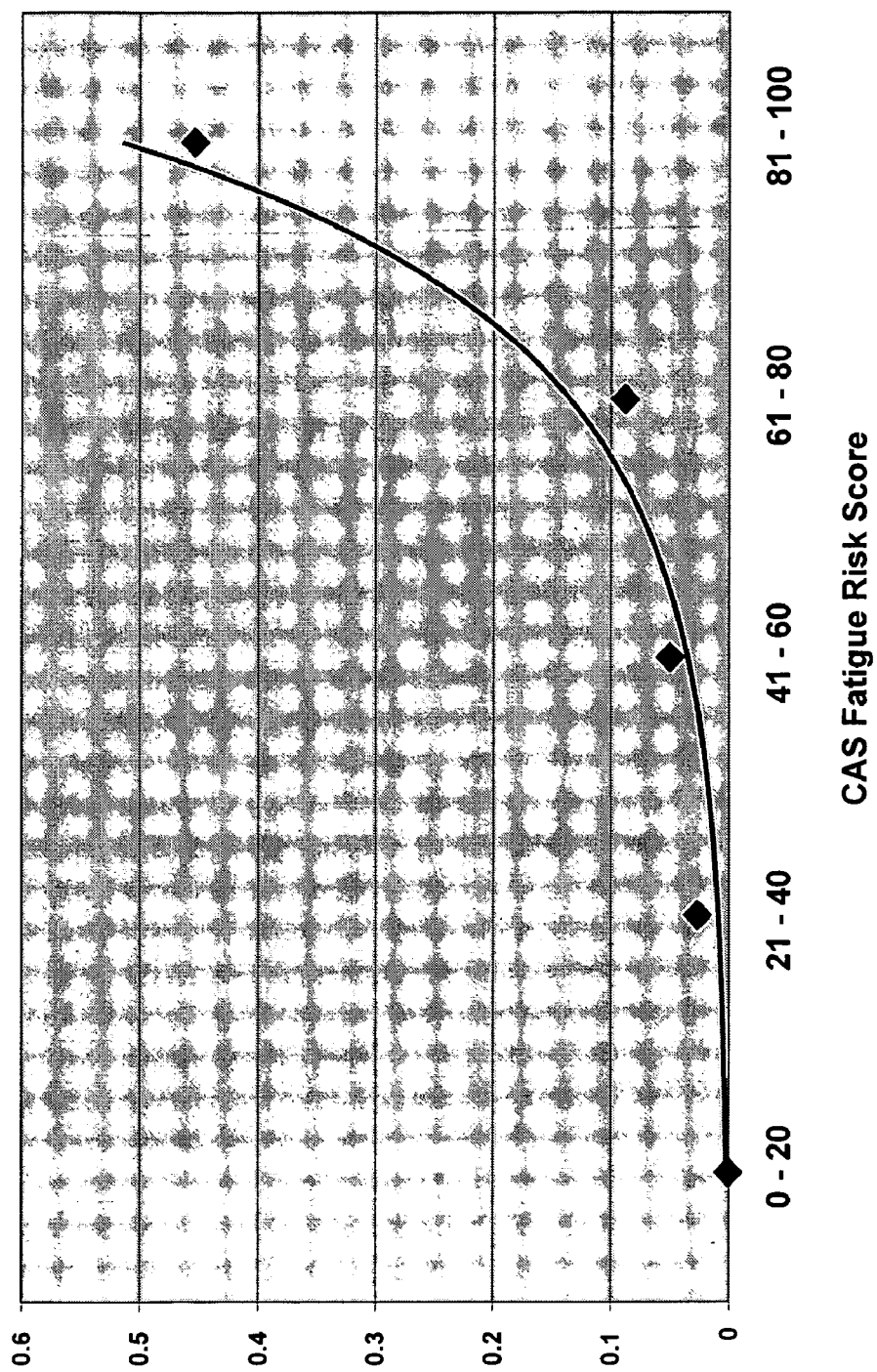
FIG. 8 contains a graph illustrating a relationship between fatigue risk scores and the probability of a driver having an accident within a year.

When the DOT reportable accident rates segmented by Fatigue Score range were compared (i.e. 0-20; 21-40, 41-60; 61-80; 81-100) the probability of having a DOT-recordable accident per year of driving in the high Fatigue Risk (CAS=81-100) group was 0.454, in the next highest Fatigue Risk group (CAS=61-80) was 0.088, in the medium Fatigue Risk group (CAS=41-60) group was 0.050, in the reduced Fatigue Risk group (CAS=21-40) group was 0.027, and in the minimal Fatigue Risk group (CAS=0-20) group was 0, demonstrating an exponential relationship between CAS Fatigue Score and accident risk, as shown in FIG. 8.

Figure 9:
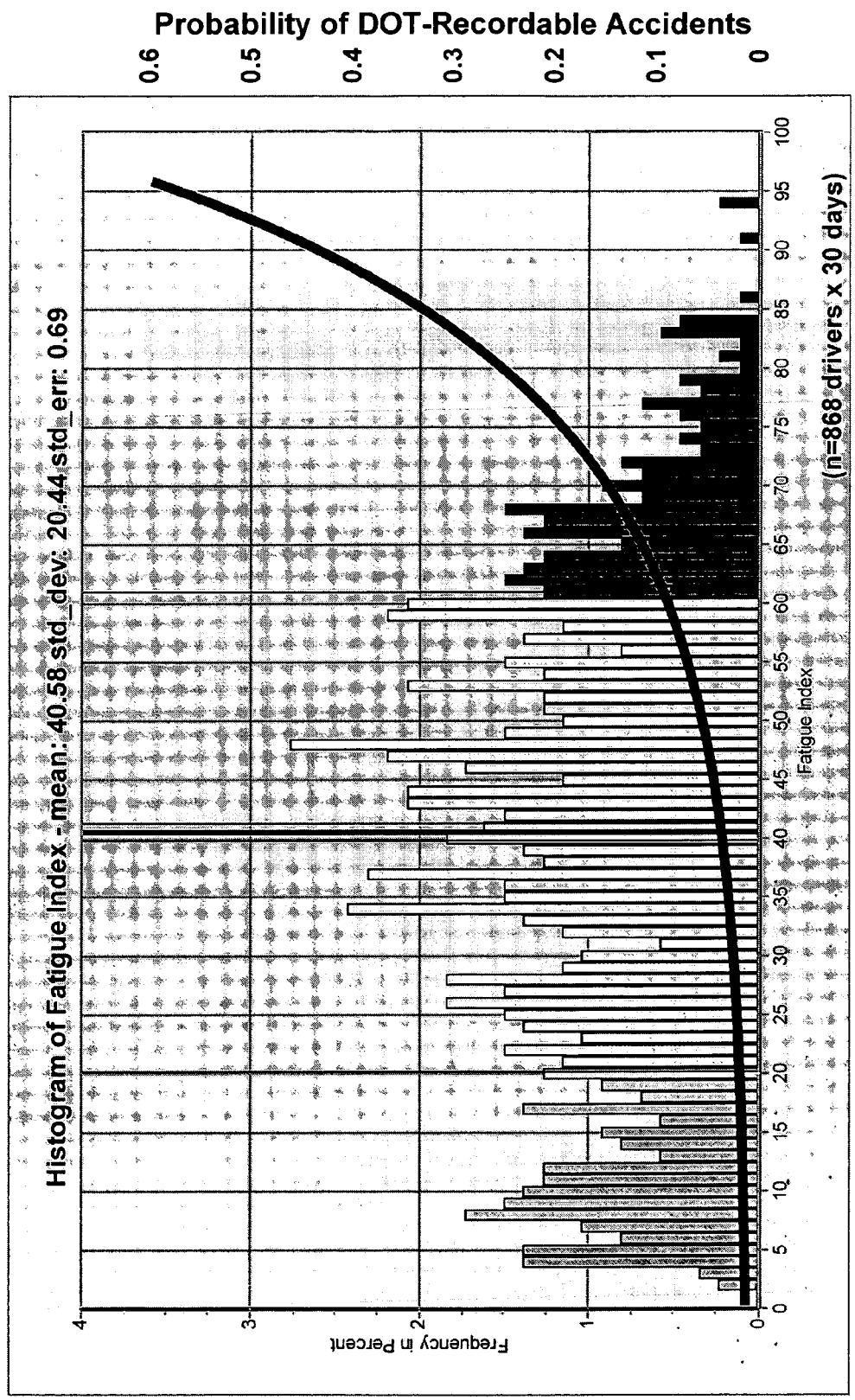
FIG. 9 contains a histogram generated from the graphs of FIGS. 7 and 8 illustrating a relationship between fatigue risk scores and a probability of a driver having an accident within a year.

FIG. 8 contains a graph illustrating a relationship between fatigue risk scores and the probability of a driver having an accident within a year. FIG. 9 contains a histogram generated from the graphs of FIGS. 7 and 8 illustrating a relationship between fatigue risk scores and a probability of a driver having an accident within a year. As shown in FIGS. 8-9, the probability of a driver having a DOT-reportable accident within a year depends on the CAS Fatigue Score of that driver. An exponential increase risk occurs with higher Fatigue Scores so that attention to reducing the fatigue score in the highest fatigue score drivers yields significant benefits on safety. The exact scale of probability rates (DOT recordables/per year/per driver) for any given trucking operation will depend on the other intrinsic risks in that operation, and hence the scale on the graph ordinate will vary depending on the specific types of risk in any particular operation.

It should be recognized that exact ordinate scale of probability rates (DOT recordables/per year/per driver) is not generalizable across trucking fleets. The scale for any given trucking operation will depend on the other intrinsic risks in that operation. Hence the scale on the ordinate of FIGS. 8 and 9 will vary depending on the other factors (e.g. nature of loads, age of vehicles, road conditions, training of drivers, etc.) which contribute to the overall risk of the particular operation. The factors are addressed by also creating a driver profile score and calculating overall risk by combining the fatigue risk score with the drive profile score. In conclusion, however, there is an accelerating disproportionately higher accident risk with the highest fatigue scores. Confirmation of this conclusion is discussed in the following intervention studies.

Driver Work-rest Schedule Interventions Based on CAS Fatigue Scores Reduce the Rate and Severity of Truck Accidents An important test of the CAS Fatigue Score is to determine if work-rest decisions based on CAS scores can be used to actually reduce the accident rate in a trucking fleet. To design an appropriate intervention to reduce the risk of driver fatigue, it is taken into account that the actual pattern of day-to-day duty and rest hours which impacts driver fatigue is determined by a) the business that the trucking carrier accepts, b) the sequence of trips constructed each workday for each driver by dispatchers, and c) the day-to-day decisions by the truck drivers who drive each truck.

The study was conducted collaboratively with the trucking operations of Dupre' Transport, LLC. A population of approximately 500 drivers operates three different types of trucking operation—a slip-seat two shifts per day Hazmat (gasoline delivery) service, a dedicated fixed route service for manufacturers, and an NSIR truckload operation. Special applications to NSIR operations are further described below.

The managers and dispatchers in the Dupre' trucking operations were provided with monthly analyses of the CAS fatigue scores for every driver, and the dispatchers were educated on how they could reduce fatigue scores by adjusting the timing and duration of driver daily and weekly work and rest patterns. The options available to the dispatchers included adjusting the start time and end times of work, providing rest breaks which allowed two consecutive nights of sleep, minimizing night work, avoiding rapid rotations in the starting time of work, and reducing the number of consecutive shifts worked. To re-enforce dispatcher behavior, senior management implemented a policy that made every dispatcher and terminal manager personally accountable for the monthly CAS fatigue scores of the drivers who reported to them.

Figure 10:
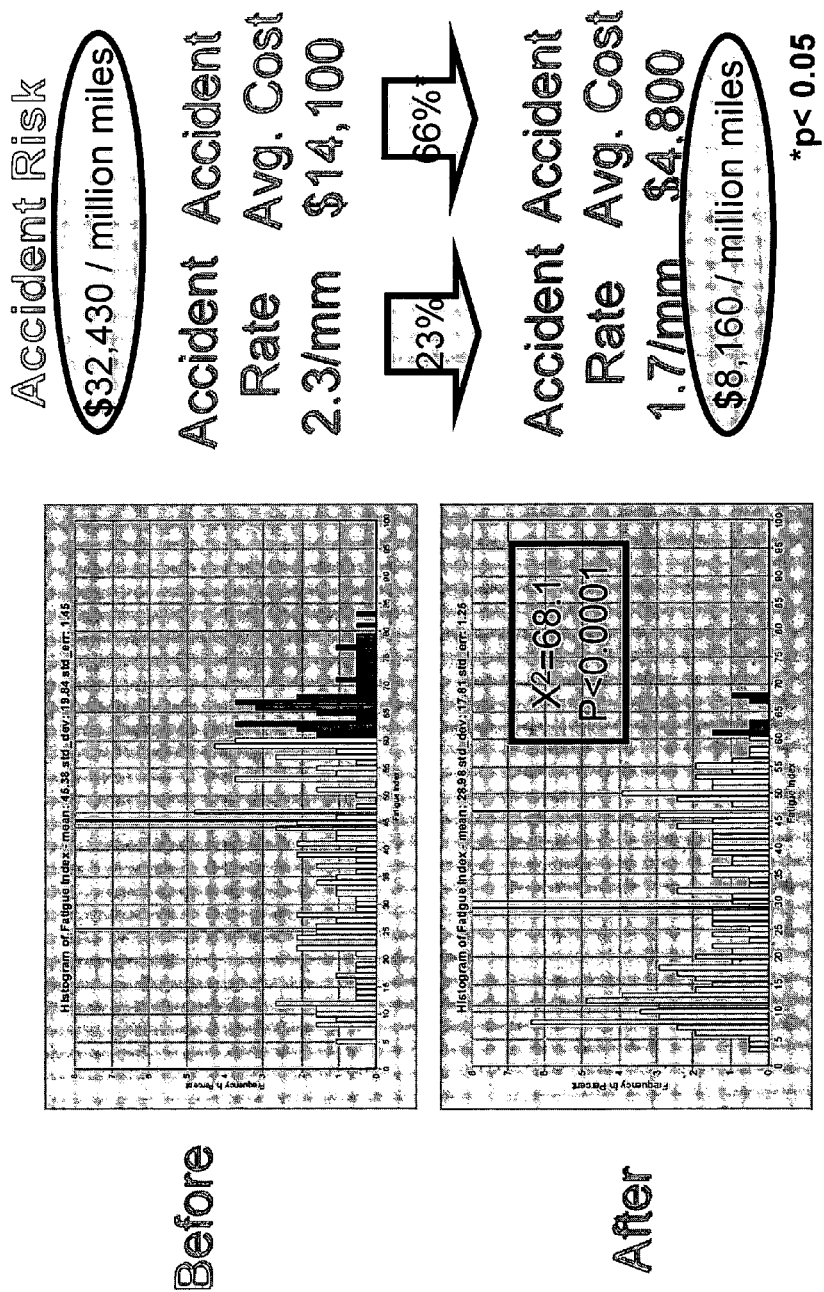
FIGS. 10 and 11 contain graphs illustrating fatigue risk scores, accident rates, and accident costs before and after applying the FRISPB paradigm shown in FIG. 5, according to an embodiment of the present invention.
Figure 11:
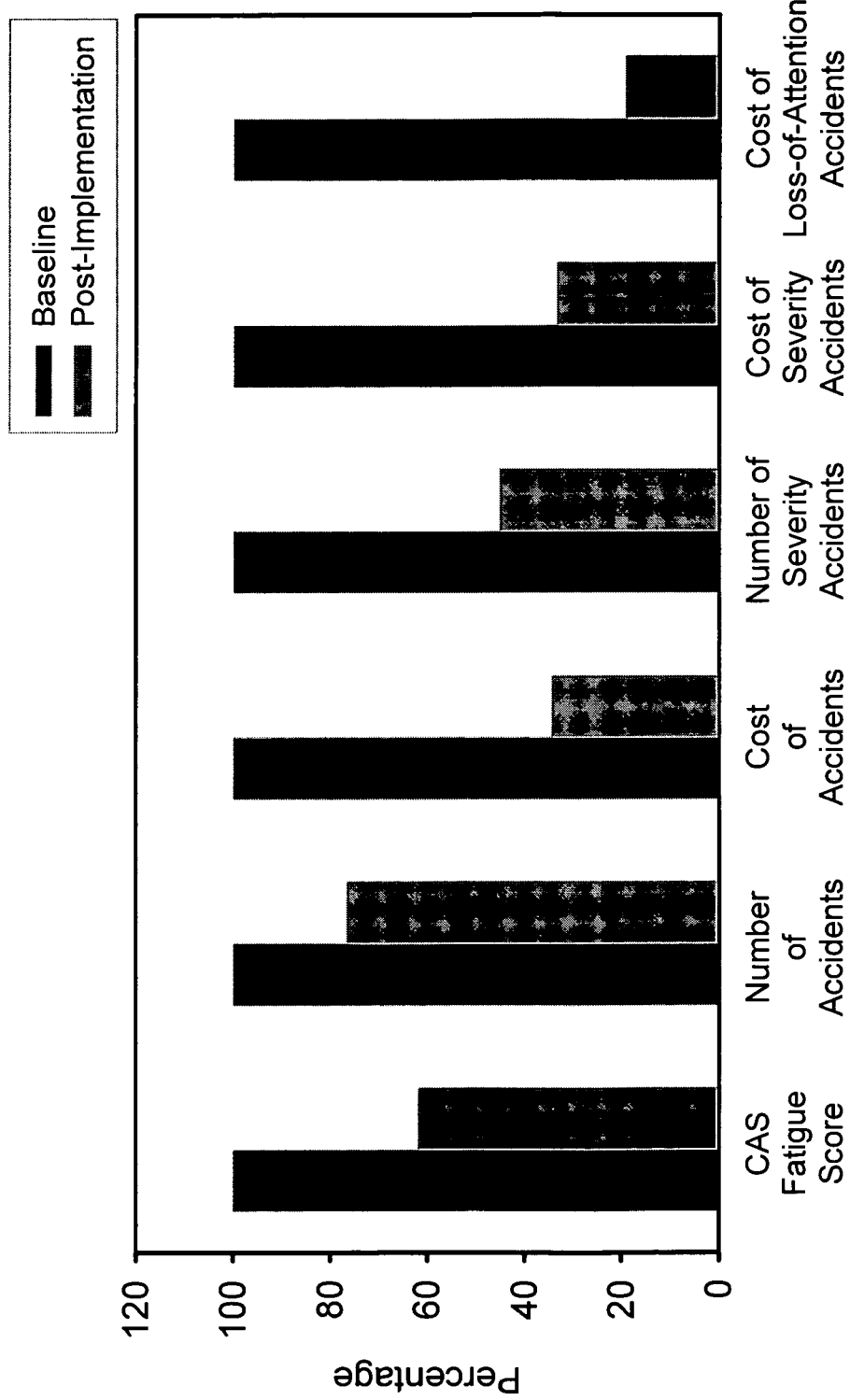

FIGS. 10 and 11 contain graphs illustrating fatigue risk scores, accident rates, and accident costs before and after applying the FRISPB paradigm shown in FIG. 5, according to an embodiment of the present invention. Fatigue Score group averages are indicated by vertical lines. In this manner, the CAS Fatigue Scores were provided as feedback back to dispatchers and managers. In particular, FIG. 10 shows the shift of CAS fatigue scores that occurred as terminal managers reviewed CAS score results on a monthly basis, and applied techniques in driver scheduling to reduce fatigue score while still providing the 24/7 (twenty-four hour a day/seven day a week) service required by the customers. The fatigue score fell from a pre-intervention mean of 46.8+1.4 SEM to 28.9+1.2 SEM (t=9.41, p<0.0001). The percentage of elevated fatigue risk scores (61 and over) fell from 28.9% to 3.9% and percentage of minimum fatigue risk scores (1-20) increased from 14.9% to 44.6% ($\chi^2$=68.1, df=4, p<0.0001). As shown in FIGS. 10 and 11, a significant reduction in fatigue scores, and the frequency and severity of accidents, was observed.

This reduction in CAS fatigue score was associated with a reduction in the number and severity of accidents. The total number of truck accidents dropped 23.3% from an average rate of 2.30/million miles for the three years prior to the intervention (April 1998-March 2001) to 1.76/million miles for the year (April 2001-March 2002) when CAS fatigue score management was instituted, and the average cost per accident dropped 65.8% from $14,088±4,307 SEM to $4,820±1,437 SEM (t-test, p<0.05). Severity accidents (over $20,000 cost) dropped 55% from an average rate of 0.20/million miles to 0.09/million miles, and the average cost of the severity accidents dropped 66.7% from $152,384±40,841 SEM per accident to $50,809±6,080 SEM per accident over the same time frame (t-test, p<0.05). The total cost of loss of attention accidents (defined as collisions, hit rear of another vehicle, loss of control) dropped 80.9% from a pre-intervention level of $1,187,699/year to $226,627/year under this risk-informed performance-based program).

As a result of these studies, which addressed the above-mentioned criteria for validating an expert fatigue risk system for trucking fleets, the use of CAS as an expert system which can measure Fatigue Risk in trucking fleets is qualified. Furthermore, CAS can be used effectively to reduce truck driver accident rate as part of a FRISPB program. It follows that the CAS, as a validated expert system, can be used in the FSM program described herein.

9. Truckload Operation Field Trials and Duty Rest-Simulations Demonstrate that Safety is "Equivalent or Greater" with the RIPB Paradigm The following is a review of the experience gained over three years of undertaking a full-scale field validation of the safety benefits of operating under an FRISPB program in 1) irregular-route truckload drivers, 2) other types of trucking operations, and 3) with simulations of the outcomes of operating under FSM rules, and that substantial reductions have been achieved in accidents, injuries and driver turnover rates.

Three-year Case Study of FRISPB with Truckload Drivers

A three-year field trial was conducted with truckload drivers operating under a Fatigue-Risk-Informed Safety-Performance-Based (FRISPB) system. See Moore-Ede, M, Heitmann, A, Dawson, T and Guttkuhn, R. "Truckload Driver Accident, Injury and Turnover Rates Reduced by Fatigue-Risk-Informed Performance-Based Program," Proceedings of the 2005 International Conference on Fatigue Management in Transportation Operations, FMCSA and Transport Canada, Seattle, Wash. September 2005, incorporated herein in its entirety by reference. This case study involved approximately 125 truckload drivers operating under a FRISPB process using the CAS expert system for a three year period. Dupre' Transport, LLC provided the following data for the public record.

The baseline years were FY 98/99, FY 99/00 and FY 00/01. During these years the company operated with a traditional safety management program. Then Dupre' Transport, LLC introduced the FRISPB safety management program toward the end the FY 00/01 fiscal year. The FRISPB program included manager and driver sleep management and alertness training, monthly analysis of CAS Fatigue Scores for each driver, and a safety management process in which drivers and manager were held accountable for the reduction of their CAS fatigue scores. Data was gathered for fiscal years FY 01/02, FY 02/03 and FY 03/04) from Dupre' Transport's ABL (truckload) division which operates non-scheduled irregular-route truckload (NSIR) services.

FIGS. 12A and 12B contain graphs illustrating a fatigue risk score distribution before and after implementing an FRISPB paradigm, respectively, according to an embodiment of the present invention. FIG. 12C contains a graph illustrating a mean fatigue risk score generated each month of an implemented FRISPB program, according to an embodiment of the present invention. In particular, FIG. 12A indicates the distribution of CAS Fatigue Scores in April 2001 at the start of the FRISPB program and FIG. 12B indicates the Fatigue Score distribution that had been achieved in this group of drivers three years later, in December 2004. The progressive change in mean Fatigue Score month by month over this three year period is shown in FIG. 12C.

CAS Fatigue Scores for a fleet of approximately 125 NSIR drivers before (April 2001) and after three years (December 2004) operating under a FRISPB program with Fatigue Scores fed back to the drivers and managers each month, and a system for holding drivers accountable to reduce the scores while operating the business to meet customer requirements. In FIG. 12A, the Fatigue Score distribution of the percentage on drivers with each possible score from 1 to 100 at the beginning of the program. In FIG. 12B, the same distribution three years later showing a sizeable left shift of drivers to the lower Fatigue Scores. In FIG. 12C, the mean Fatigue Score for the truckload drivers month by month during the implementation of the FRISPB system. As shown in FIG. 12C, not only did the mean Fatigue Score progressively decrease at the management trained the drivers and held them accountable for reducing their Fatigue Scores, but even more importantly there was a substantial left shift of the distribution of Fatigue Scores. As a result, few drivers operated in the highest CAS Fatigue Score zones where there is disproportionately greater risk of accidents and injuries occurring.

Figure 13:
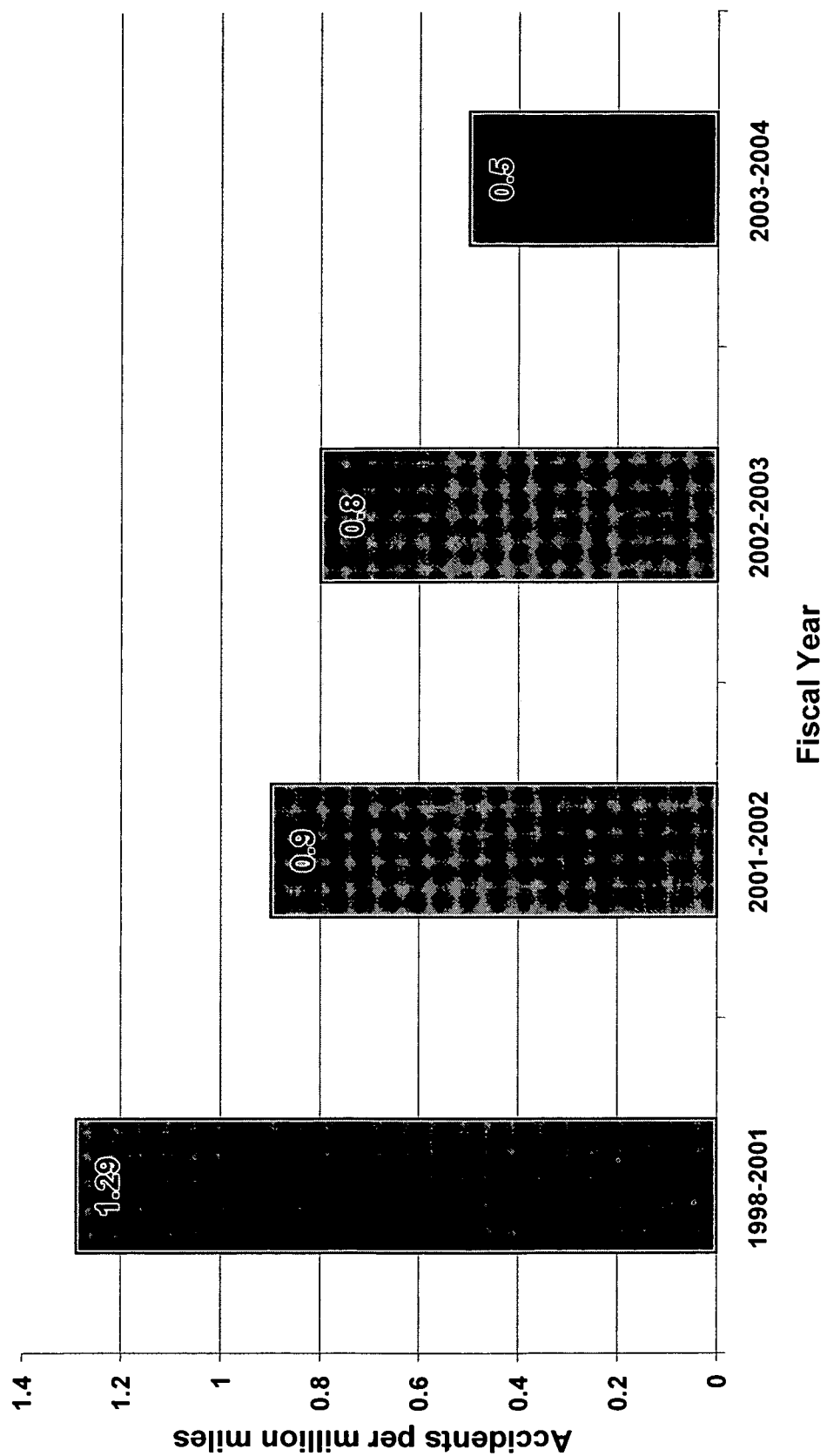
FIGS. 13-17 contain graphs illustrating accident-related statistics before and after applying an FRISPB paradigm, according to an embodiment of the present invention.

FIGS. 13-17 contain graphs illustrating accident-related statistics before and after applying an FRISPB paradigm, according to an embodiment of the present invention. As shown in FIGS. 13-17, the reduction in CAS Fatigue scores as a result of the FRISPB program correlated with a parallel decrease in accidents, and personal injuries in the NSIR drivers. FIG. 13 illustrates a comparison of the Big Four accident rate for NSIR drivers (i.e., Rollovers, Rear-End Collisions, Lane Change accidents and Intersection Accidents) before (three baseline years 1998-2001) and during three years of implementation (2001-2002, 2002-2003, and 2003-2004) of a FRISPB Fatigue Management program with monthly CAS Fatigue Score feedback to the drivers who were held accountable for minimizing their own CAS Fatigue Scores. As a result, the accident rate of 1.29 per million miles found in the base years (1998-2001) fell to 0.9 in 2001-2002, to 0.8 in 2002-2003 and to 0.5 in 2003-2004.

Figure 14:
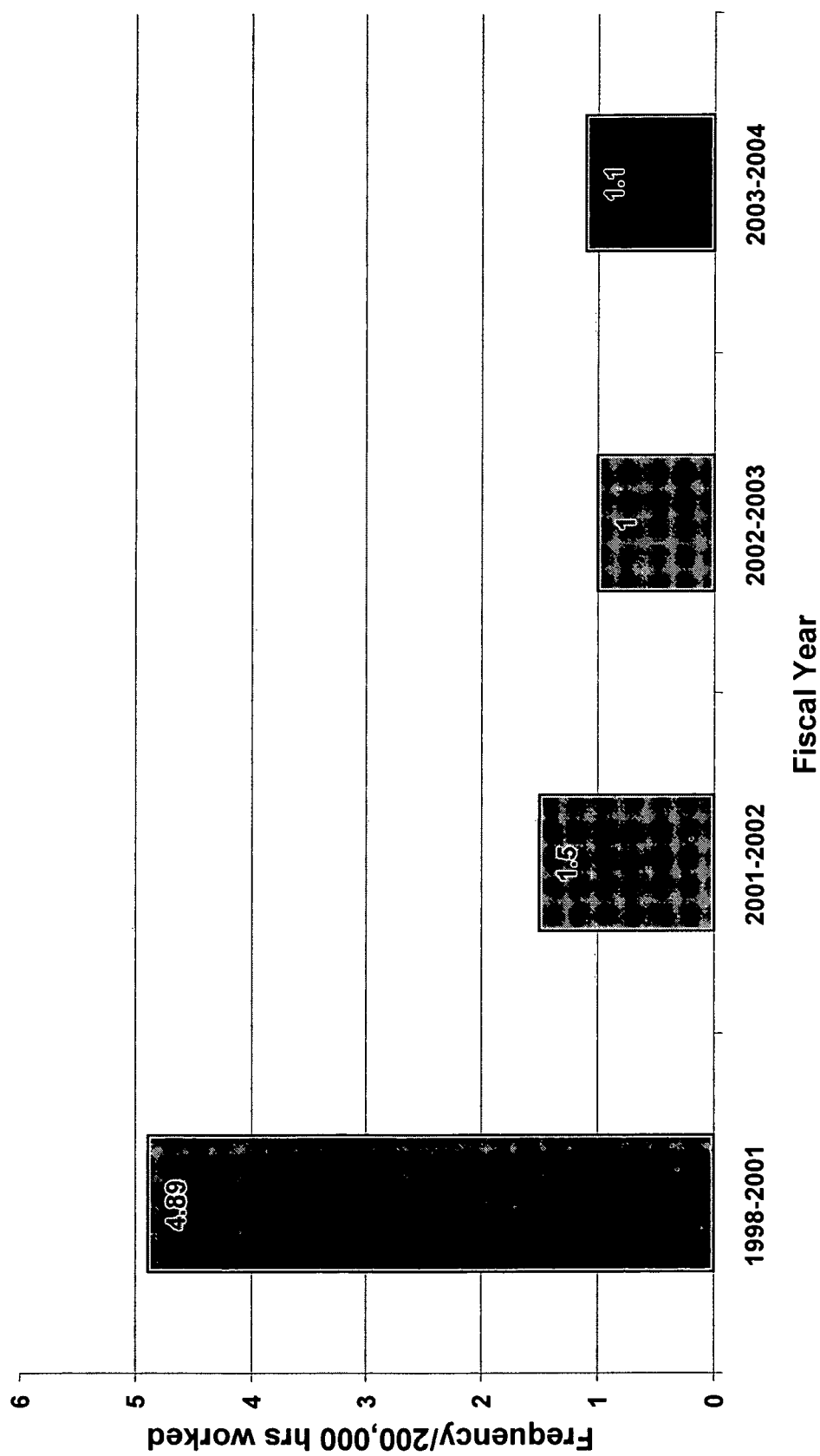

There was an equally impressive reduction in Personal Injuries among NSIR drivers in the Dupre' Transport, LLC fleet, as shown in FIG. 14. Specifically, FIG. 14 illustrates a comparison of the personal injury rate of 125 NSIR drivers before (three baseline years 1998-2001) and during three years of implementation (2001-2002, 2002-2003, and 2003-2004) of a FRISPB Fatigue Management program with monthly CAS Fatigue Score feedback to the drivers who were held accountable for minimizing their own CAS scores. As a result, correcting all data to injuries per 200,000 hours worked, the rate fell from 4.89 in the base years 1998-2001 to 1.5 in 2001-2002 and to 1.0 and 1.1 in 2002-2003 and 2003-2004 respectively. In addition, the benefits of FRISPB safety management expanded considerably beyond accident and injury statistics. For example, morale and customer service improved, and driver retention increased.

Safety and Operational Benefits from FRISPB Across Other Types of Trucking Operations Similar results were found by implementing FRISPB fatigue safety management across the entire Dupre' Transport, LLC company which included approximately 500 drivers on fixed routes, and local deliveries. Instead of the primary responsibility for minimizing CAS Fatigue Scores being placed on the driver in the NSIR operations, in Dupre' Transport's scheduled operations the responsibility was shared with the dispatcher who was responsible for scheduling the driver's trips.

Figure 15:
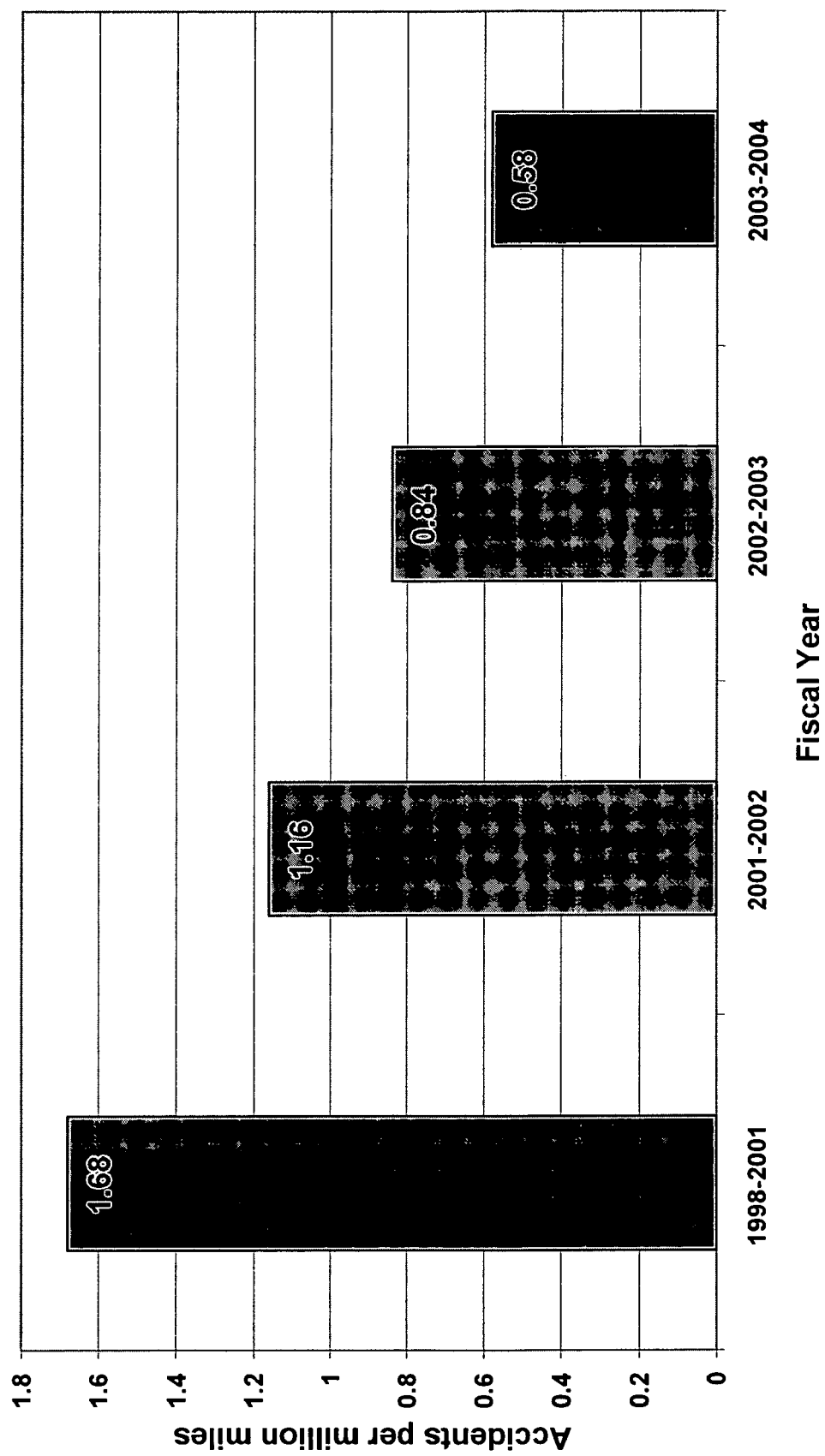

FIG. 15 contains a graph illustrating accident rates per million miles driven for the entire Dupre' Transport, LLC company before applying the FRISPB program, i.e., during the baseline years 1998-2001, and after applying the FRISPB program, i.e., the years 2001-2002, 2002-2003 and 2003-2004. As shown in FIG. 15, the Big Four accident rate (i.e., rollovers, rear-end, lane change, intersection) fell from 1.68 per million miles in the three baseline years to 1.16 in 2001-2002, 0.84 in 2002 and 0.58 in 2003-2004.

Figure 16:
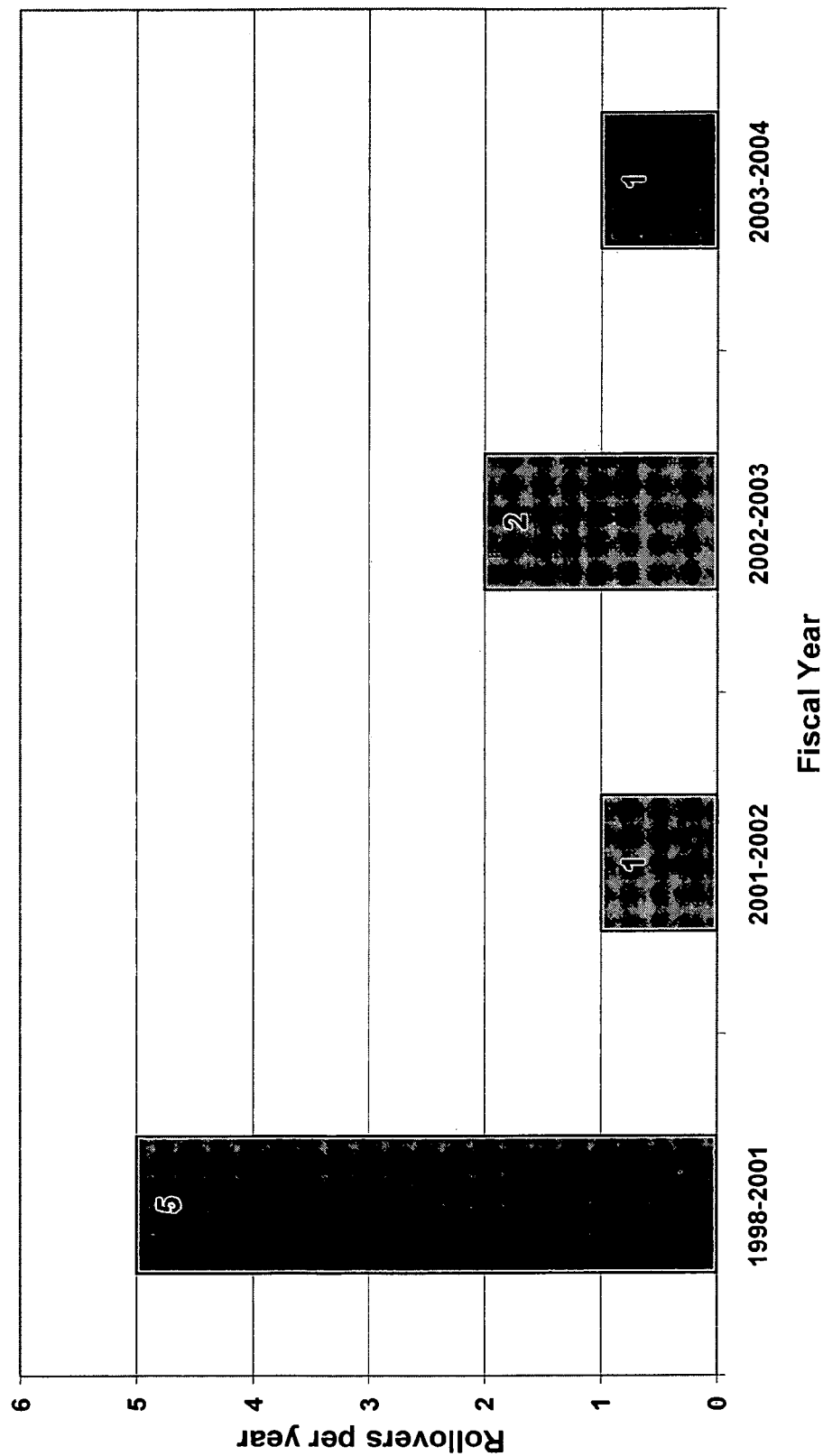

FIG. 16 contains a graph illustrating a rollover rate before and after applying the FRISPB program. As illustrated in FIG. 16, the number of rollover truck accidents per year fell from 5 per year in the three baseline years to an average of 1.3 per year in 2001-2002, 2002-2003 and 2003-2004 with the FRISPB program.

Figure 17:
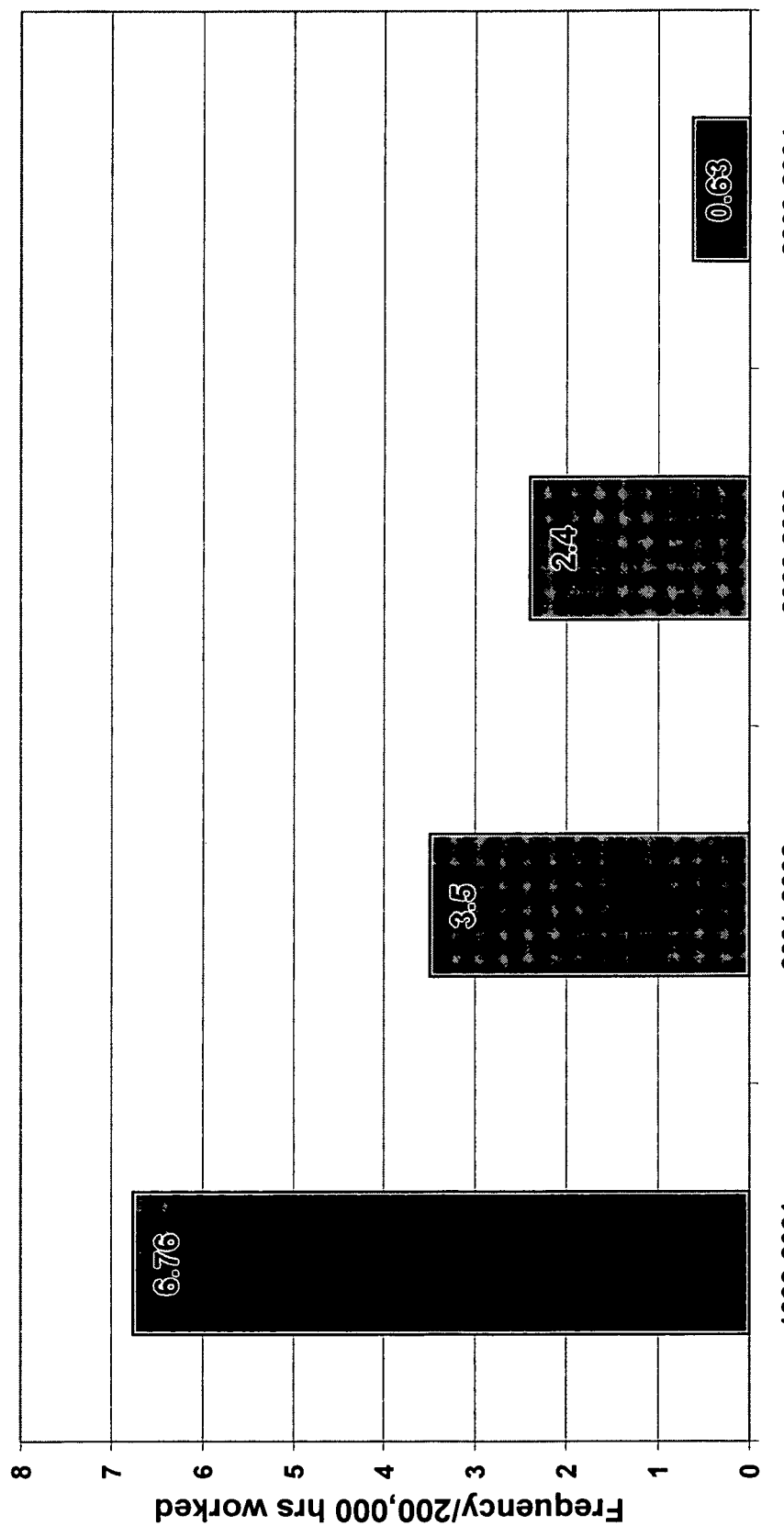

FIG. 17 contains a graph illustrating a personal injury rate before and after applying the FRISPB program. As shown in FIG. 17, the personal injury rate per 200,000 hours driven for the Dupre' Transport, LLC company was reduced in years 2001-2004 following implementation of FRISPB fatigue risk management. In particular, the rate of personal injury accidents fell across the company with the FRISPB fatigue risk management program in place. In addition, the personal injury rate fell from 6.76 per 200,000 hours worked in the three baseline years to 3.5 in 2001-2002, 2.4 in 2002 and 0.63 in 2003-2004.

In sum, the results described herein were compiled after a full scale trial of using the CAS Fatigue Risk expert system in a FRISPB safety management program over a period exceeding three years show that dramatic improvements in accidents, injuries and turnover can be obtained in both NSIR and other trucking operations with the FRISPB process.

Simulations of Flexible Sleep Management Rules Vs. Fixed Hours-of-Service Show that Safety is Equivalent or Greater Because these trials with Dupre' Transport, LLC were conducted without an exemption to the HoS regulations, they were by necessity conducted under both old (pre-2004) and new (post 2004) HoS regulations. As we have discussed, the current HoS regulations are too restrictive and create problematic situations for NSIR drivers where alert drivers are forced to stop and where tired drivers are legal to drive and provided with no incentive to stop and rest.

To illustrate the problem and the benefits of having an FRISPB program, the simulation capabilities of the CAS expert system have been used to examine a number of driving patterns that are legal under the current Hours of Service and compared them to driving patterns that would not be legal unless an Hours of Rest exemption for a FRISPB with Flexible Sleep Management program was granted. The significant benefits that are possible with FRISPB can thereby be illustrated.

FIGS. 18-23 contain graphs illustrating work-rest patterns of truck drivers having different fatigue risk scores, according to an embodiment of the present invention.

Figure 18:
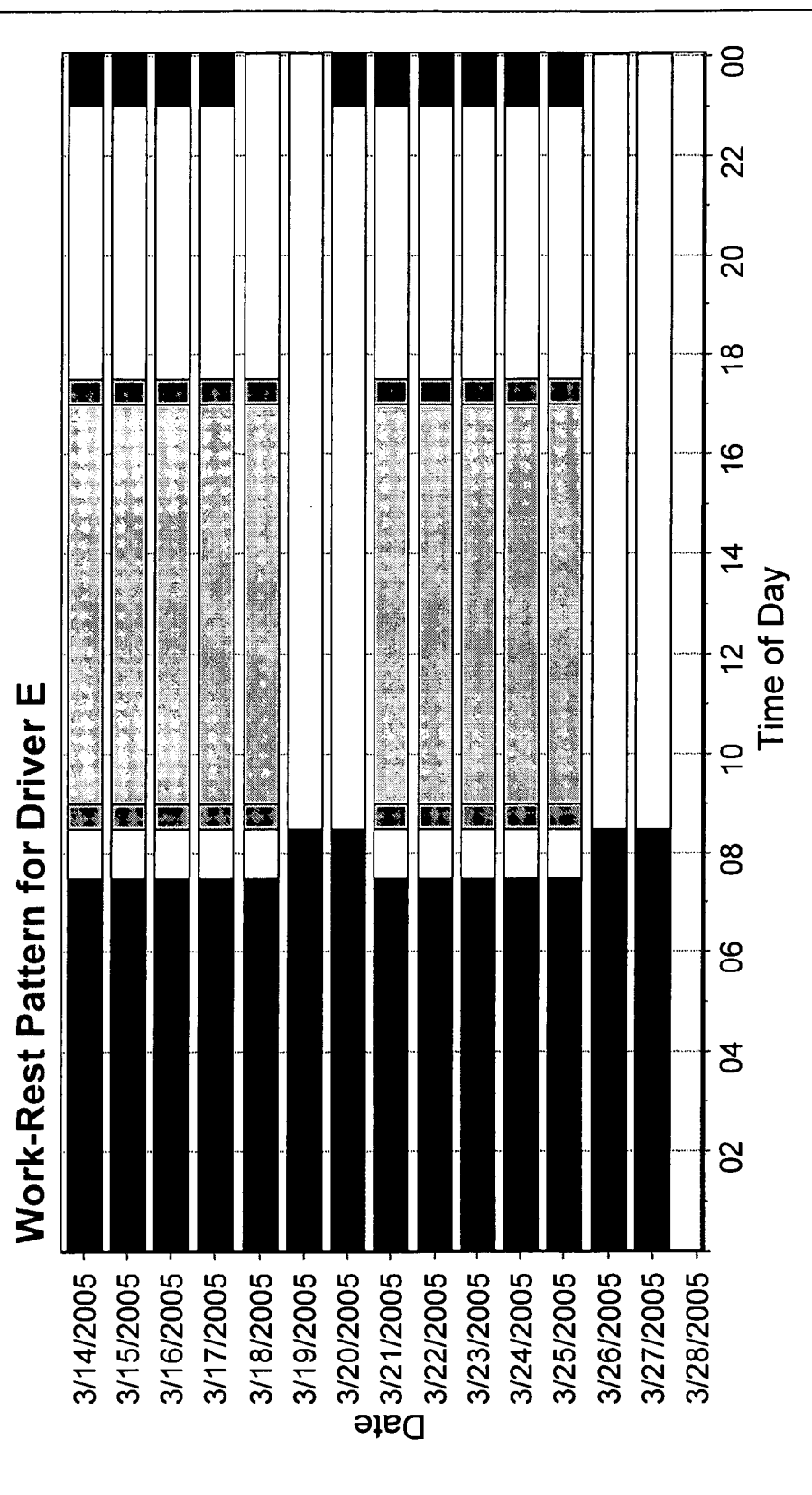
FIGS. 18-23 contain graphs illustrating work-rest patterns of truck drivers having different fatigue risk scores, according to an embodiment of the present invention.

FIG. 18 illustrates the work-rest pattern of a local route truck driver (Driver E) working five days a week from 9 AM to 5 PM, with a 30-minute commute, and a sleep period from 11 PM until 7:30 AM. All other time awake is represented by white blocks. The fatigue score of Driver E is just 4.4 (on the scale ranging from 0 (no fatigue) to 100 (maximum fatigue)), indicated that Driver E had very little fatigue, and, as a result, Driver E lies on the far left of the Fatigue Score distribution in FIG. 7.

Figure 19:
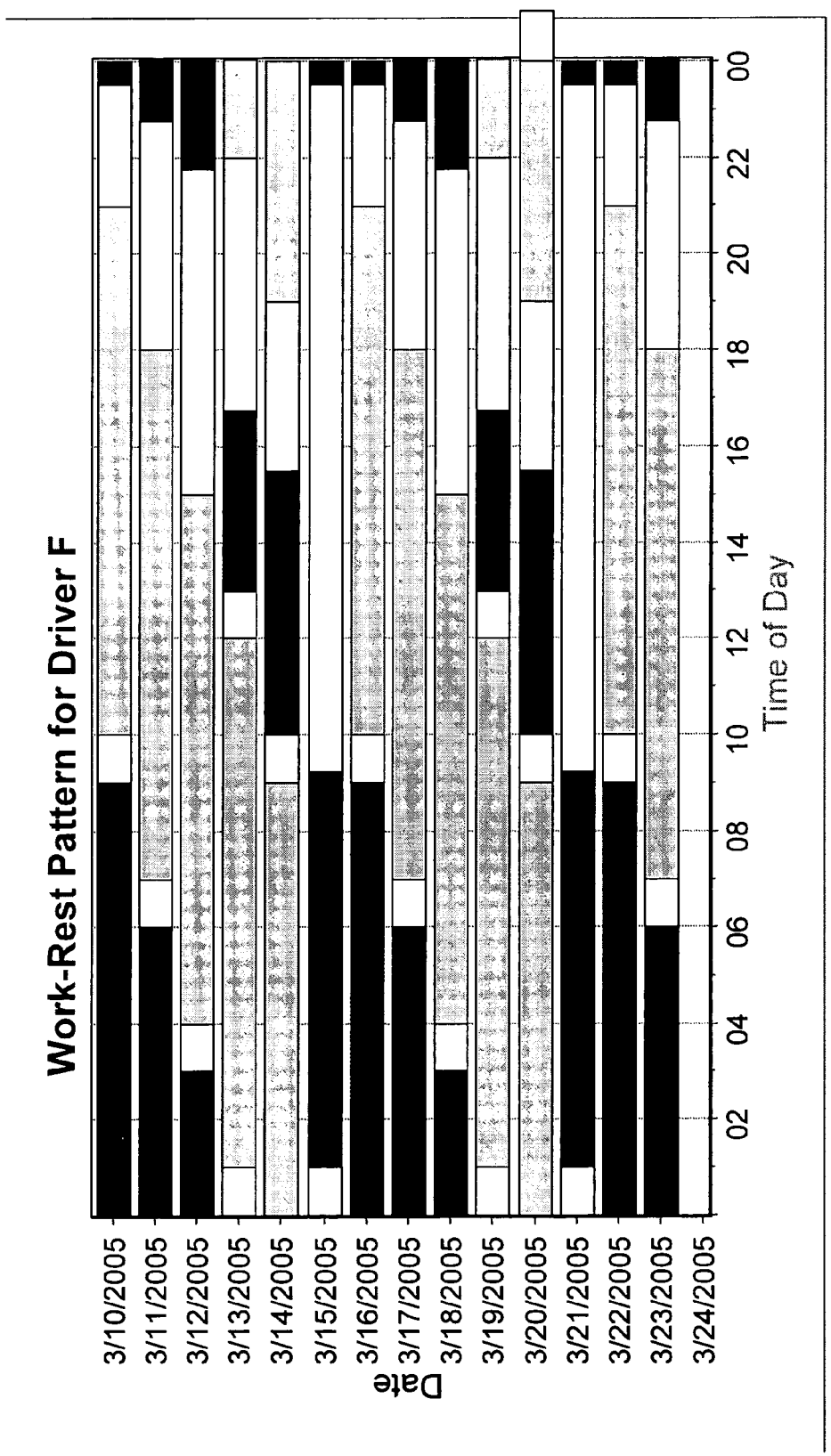

FIG. 19 illustrates the work-rest pattern of Driver F, who represents a driver complying with current HoS regulations. In FIG. 19, Driver F drives 11-hours each day with no rest period. He then rests for 10 hours, before beginning another 11-hour day. Driver F therefore drives the maximum allowed under current HoS and has no on-duty non-driving time in his schedule. His CAS Fatigue Score of 76.5 indicating a high Fatigue Risk despite being fully compliant with current HoS regulations. After five days Driver F has driven for 55 hours. Under current HoS regulations, at the start of the sixth day Driver F can only drive for five hours before stopping to take a 34-hour break to restart his clock. His sleep pattern within the time off has been calculated as the most likely sleep pattern of someone on this work schedule.

Driver F therefore faces the difficult challenge of a schedule that is constantly rotating backwards. Every day his shift starts three hours earlier than it had the previous day. The 2004 HoS regulations attempt to minimize this backward rotation by allowing drivers to work for three non-driving hours per day. But for the long haul driver who may have no loading duties and very little non-driving work, this pattern is still legal under current HoS regulations. The result of this backward rotation is that this driver finds it increasingly difficult to sleep as the days of his trip pass because his body cannot adjust to a habitual sleep time. He therefore begins to obtain not only low quantities of sleep, but likely low quality sleep. His fatigue score is 76.5, indicating a high fatigue risk, which lies to the right of the Fatigue Score distribution in FIG. 7. Nevertheless, Driver F is following the HOS regulations to the letter, and Driver F is in compliance with HoS regulations.

Figure 20:
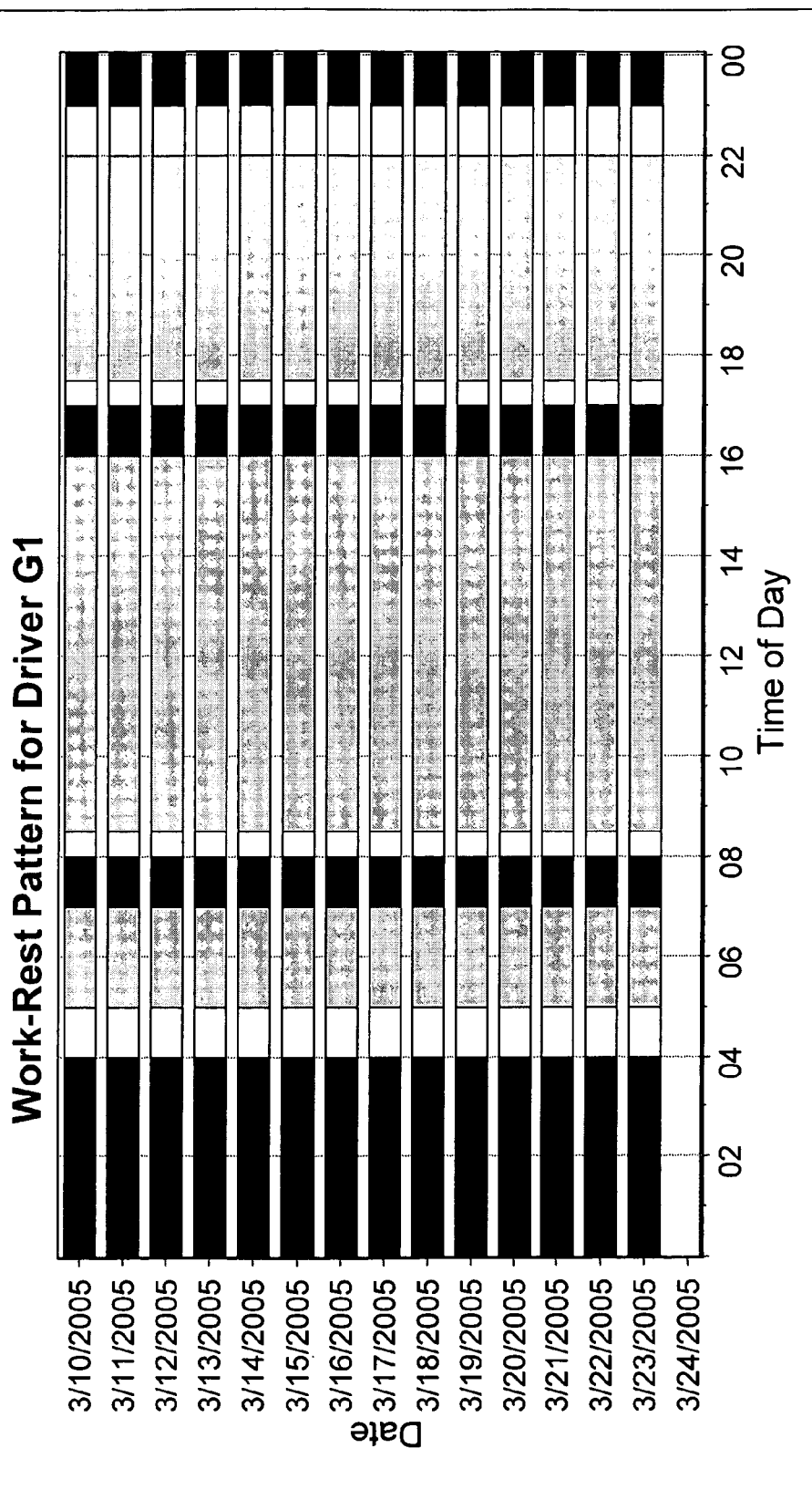
Figure 21:
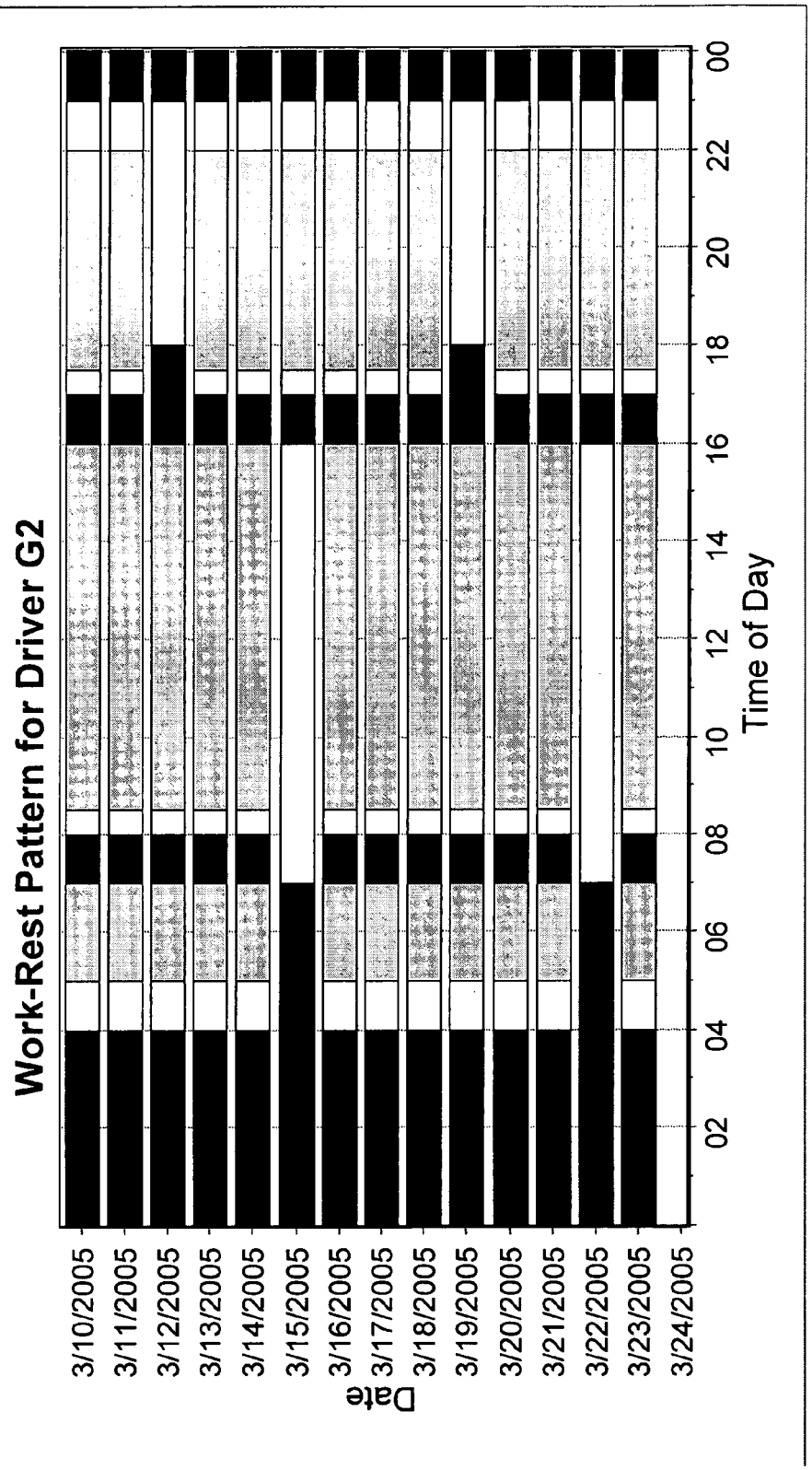

FIGS. 20-21 illustrate the work-rest patterns of Driver G, who represents a driver in violation of current HoS regulations, but less fatigued than Driver F, who is in compliance with HoS regulations. FIG. 20 illustrates Driver G having a first work-rest pattern, referred to as Driver G1, and FIG. 21 illustrates driver G having a second work-rest pattern, referred to as Driver G2. Driver G1 operates at the theoretical limit on his total weekly driving hours under Flexible Sleep Management rules, and Driver G2 has 84 hours on-duty in a 7-day span.

In FIG. 20, Driver G1 is on-duty for the maximum period allowed under the Flexible Sleep Management program. Specifically, Driver G1 is on duty 14 hours per day and finishes driving 17 hours after his day started. In particular, Driver G1 works from 5 AM until 7 AM, naps through the first part of the morning rush hour until 8:00 AM, resumes driving from 8:30 AM until 4 PM, naps during the evening rush hour until 5:00 PM, and resumes driving from 5:30 PM until 10 PM before sleeping from 11 PM until 4 AM. He repeats this pattern every day over the two week cycle. However, Driver G1 would violate the current HoS 11-hour rule, the 14-hour rule, the split sleeper rule, and the 60/70 hour as defined in 49 CFR Part 395. The 11-hour rule limits the total driving time per day that can be accomplished before requiring at least 10-hours rest; the 14 hour rule limits the consecutive amount of time a driver may be on duty, either driving or not driving, before he is required to rest; the split-sleeper rule limits the division of the minimum ten hours rest so that one portion must be of at least 8 consecutive hours, and the 60/70 hour rule limits the total number of hours driven in 7 days and 8 days respectively. While this does provide for a long day, Driver G1 uses two naps to break up the day and maintain alertness, and at the same time he is able to gain productivity by avoiding rush-hour driving. He sleeps for seven hours per day by means of a five-hour anchor sleep and two 60-minute naps, each timed around he time of the rush hour. However, because Driver G1 has chosen an effective sleep schedule to suit his needs, his CAS Fatigue Score is 31.9, indicating a relatively low fatigue risk in comparison to Driver F who had a 76.5 score. Yet Driver G1 is in violation of the daily driving limits prescribed by the HOS regulations.

As illustrated in FIG. 21, Driver G2 has a similar work-rest pattern as Driver G1, except that he only works 84 hours per week. Driver G2 takes the evening off on the $3^{rd}$ night of the week, and takes the morning and daytime driving off on the $6^{th}$ day of the week. On the third day, he extends his afternoon nap by an extra hour, and on the sixth day he uses the morning time to extend his night sleep three hours to 7 AM, and forego his usual 7 AM nap. Driver G2 commits the same HoS violations as Driver G1, but his weekly on-duty time totals 84 hours. His fatigue score is 30.5, indicating a low fatigue risk.

But like Driver G1, Driver G2 is in severe violation of the daily driving limits prescribed by the HOS regulations.

Figure 22:
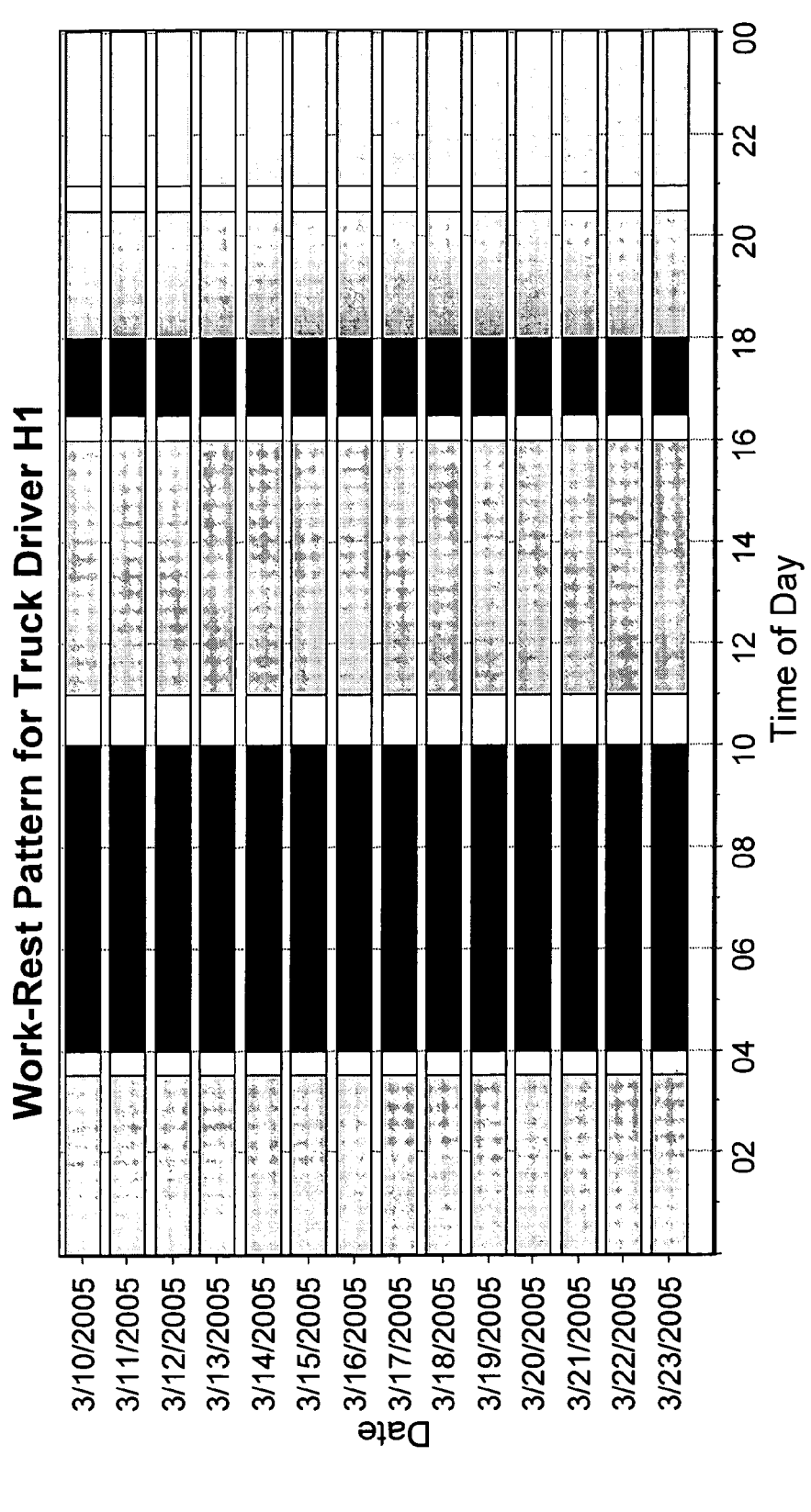
Figure 23:
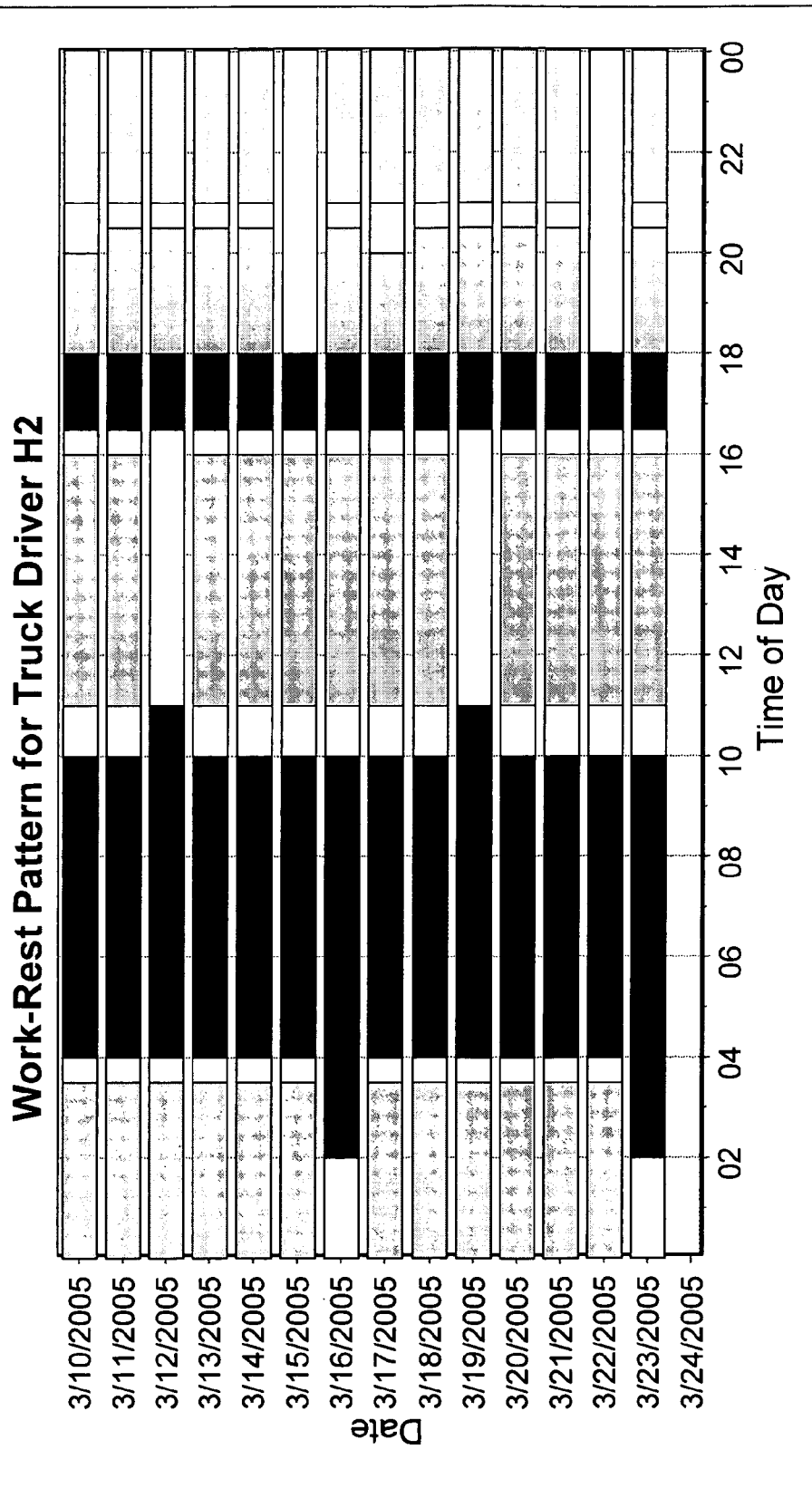

FIGS. 22-23 illustrate the work-rest patterns of Driver H1 and H2, who drive at night in violation of current HoS regulations, but are less fatigued than Driver F, who is in compliance with HoS regulations.

As shown in FIG. 22, Driver H1 is on duty 14 hours per day and finishes driving 16.5 hours after his day started. Driver H1 comes on-duty at 11 AM and drives until 4:00 PM. After a half-hour for lunch and 90 minutes to nap, he resumes driving at 6 PM. He drives until 8:30 PM, takes 30 minutes for dinner, then drives from 9 PM until 3:30 AM, covering good ground while the roads are clear of daytime travelers. He then sleeps from 4 AM until 10 AM. He repeats this pattern every day over a two week period. While Driver H1 maximizes his on-duty hours under the Flexible Sleep Management (FSM) program, but would violate the current HoS 11-hour rule the 14-hour rule, the split sleeper rule, and the 60/70 hour rule. Because Driver H1 has chosen an effective sleep schedule to suit his personal needs his CAS Fatigue Score is relatively low at 29.9.

Like Drivers G1 and G2, Driver H1 uses a napping strategy to combat the potential effects of fatigue. He too is able to gain productivity by avoiding rush-hour driving. He actually sleeps for 7.5 hours per day by means of a six-hour anchor sleep and one 90-minute nap. His fatigue score is only 29.9. But like Drivers G1 and G2, he is in severe violation of the daily driving under current hours of service.

As illustrated in FIG. 22, Driver H2 has a similar work-rest pattern as Driver H1, but only works 84 hours per week. Driver H2 takes time off during the day on the $3^{rd}$ day of the week, for example, Mar. 12, 2005, and takes the evening and morning off on the $6^{th}$ night/$7^{th}$ day of the week, for example, Mar. 15-16, 2005. On the third day, Driver H2 uses the extra time off to extend his morning sleep by an extra hour, and on the seventh morning he uses the morning time to extend his night sleep by going to bed two hours earlier than usual, at 2 AM. This driver commits the same HoS violations as Driver H1, but his weeks total 84 hours on duty. His fatigue score is 28.9, indicating a low fatigue risk. However, like Driver H1, he is in severe violation of the daily driving limits prescribed by the HOS regulations.

In sum, the field trials and simulations described herein demonstrate that FRISPB flexible sleep management (FSM) rules provide a reasonable expectation that an equivalent or greater safety level will be achieved as compared to the current HoS regulations. Indeed we have demonstrated that a large safety margin is created by operating with a Fatigue-Risk-Informed Safety-Performance-Based process using a fatigue risk assessment system. Therefore the allowance of FSM rules for NSIR drivers in place of the existing arbitrary and capricious Hours of Service regulatory limits is a reasonable accommodation. This provides significant benefits for the safety and health of NSIR drivers, and the reduction of the day to day stress of complying with HoS rules that often make little sense to these NSIR drivers.

10. Flexible Sleep Management Rules for NSIR Drivers with Appropriate Driver Training and with Compliance Ensured by a Scientifically-validated FRISPB Process Provide a Superior Approach to Managing the Risk of Truck Driver Fatigue.

As described herein, well-intended prescriptive HoS rules, while appropriate for many types of trucking operations, have significant risks of causing truck drivers to become sleep deprived just by obeying duty-driving and rest rules that are arbitrary and capricious for his own specific situation.

Figure 24:
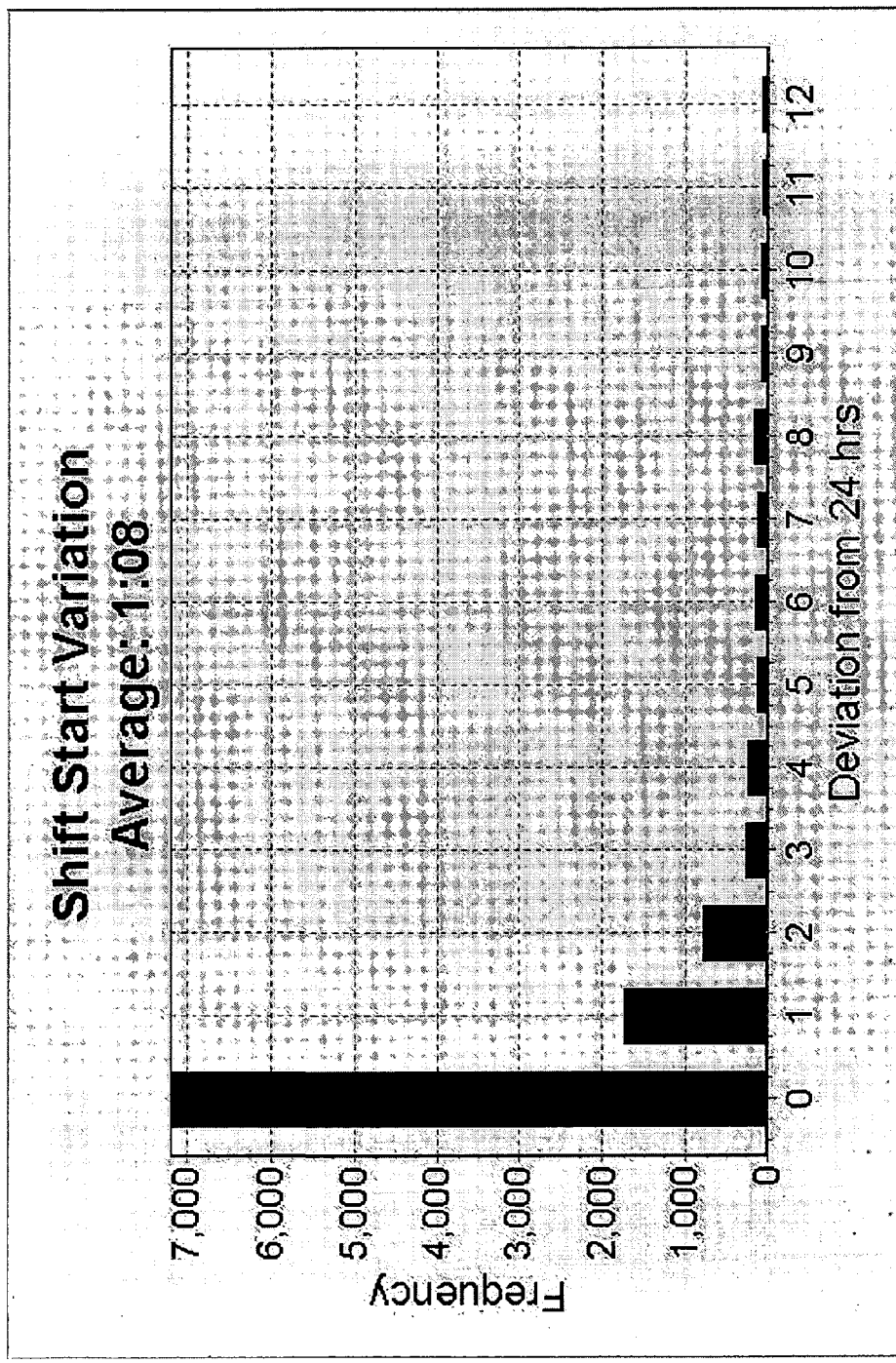
FIG. 24 contains a graph generated from a diagnostic report that shows how far drivers are deviating from the ideal 24-hour interval between successive daily times of starting to drive, according to an embodiment of the present invention.
Figure 25:
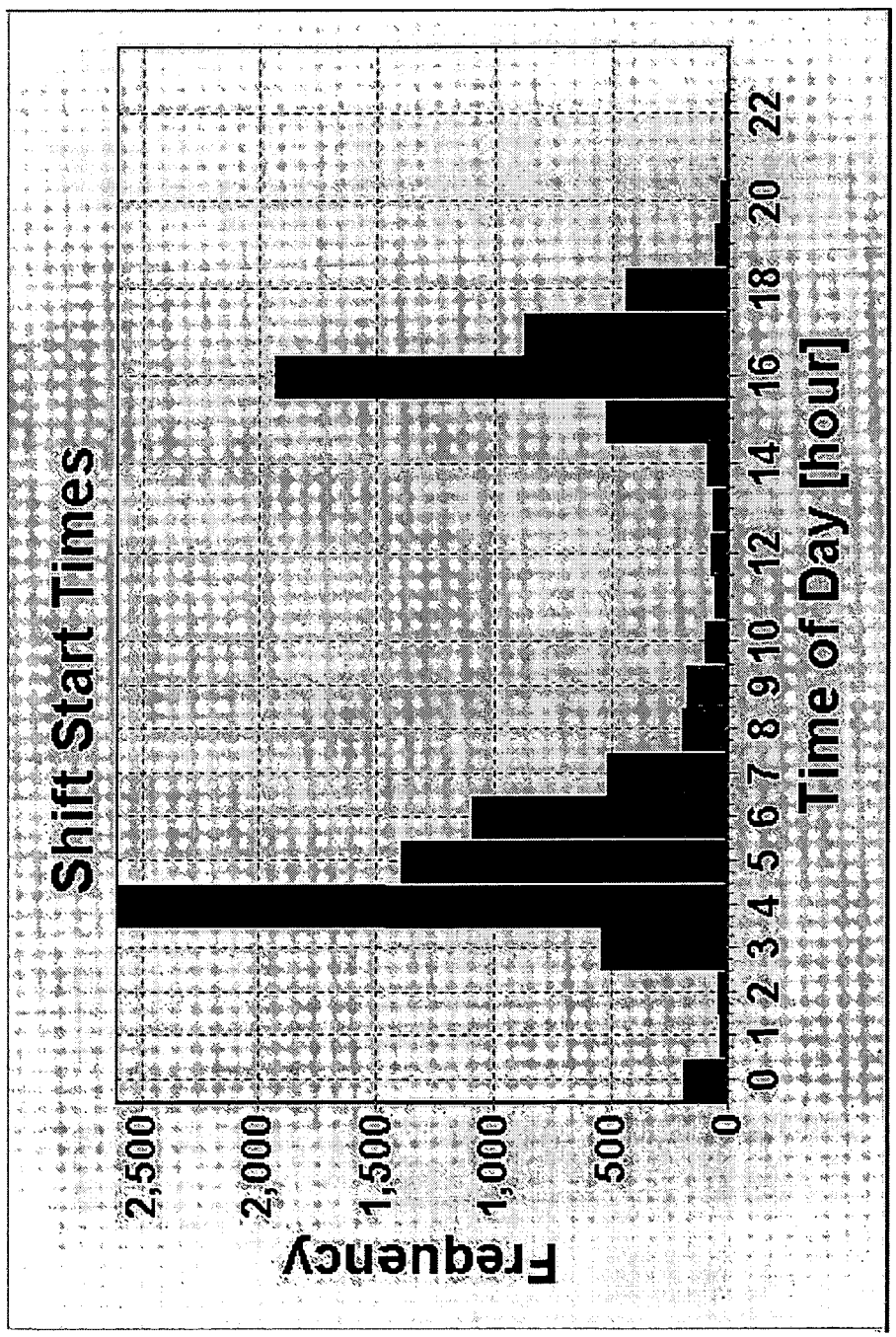
FIG. 25 contains a graph generated from a diagnostic report that shows the time of day distribution of duty start times, according to an embodiment of the present invention.
Figure 26:
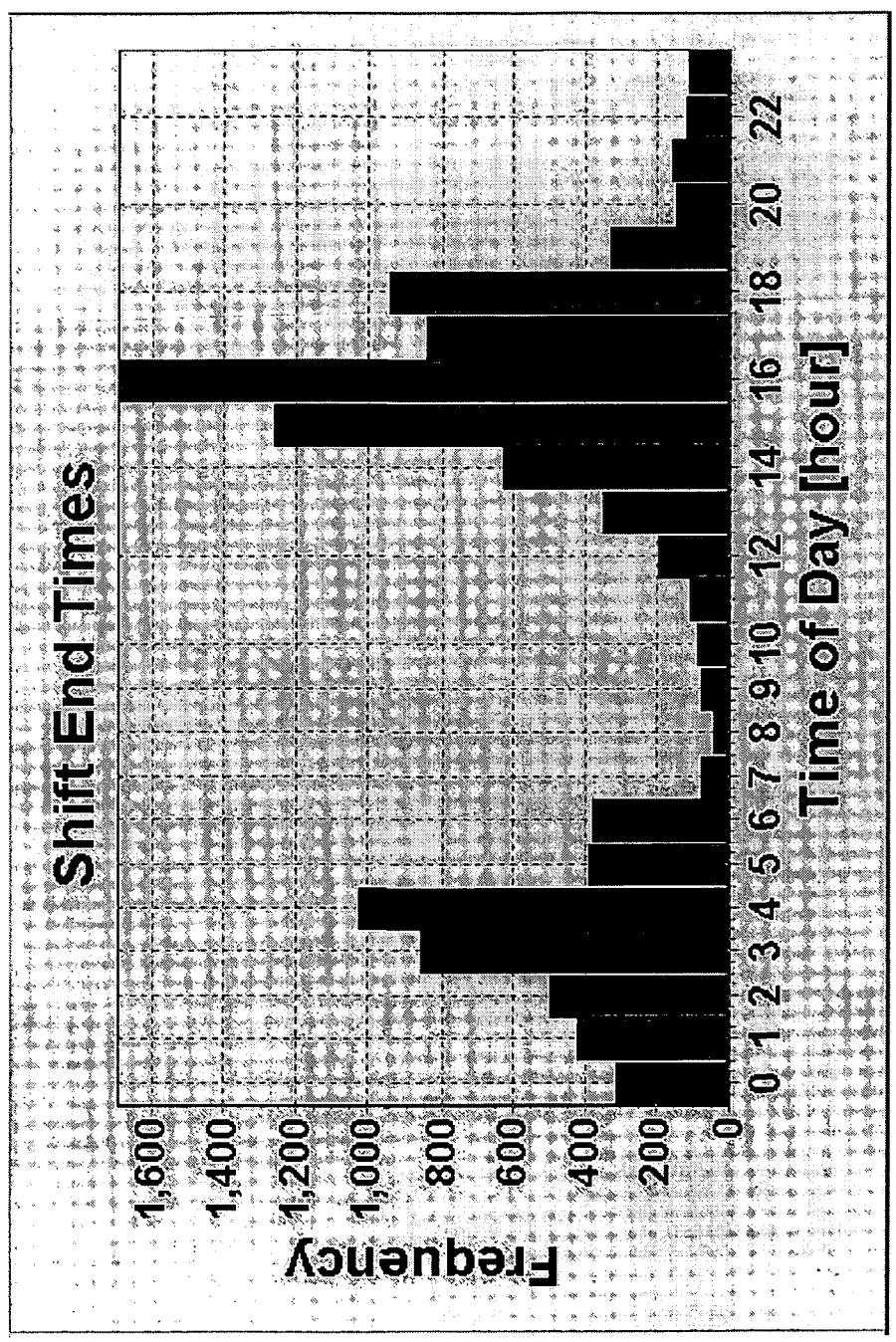
FIG. 26 contains a graph generated from a diagnostic report that shows the time of day distribution of duty end times, according to an embodiment of the present invention.
Figure 27:
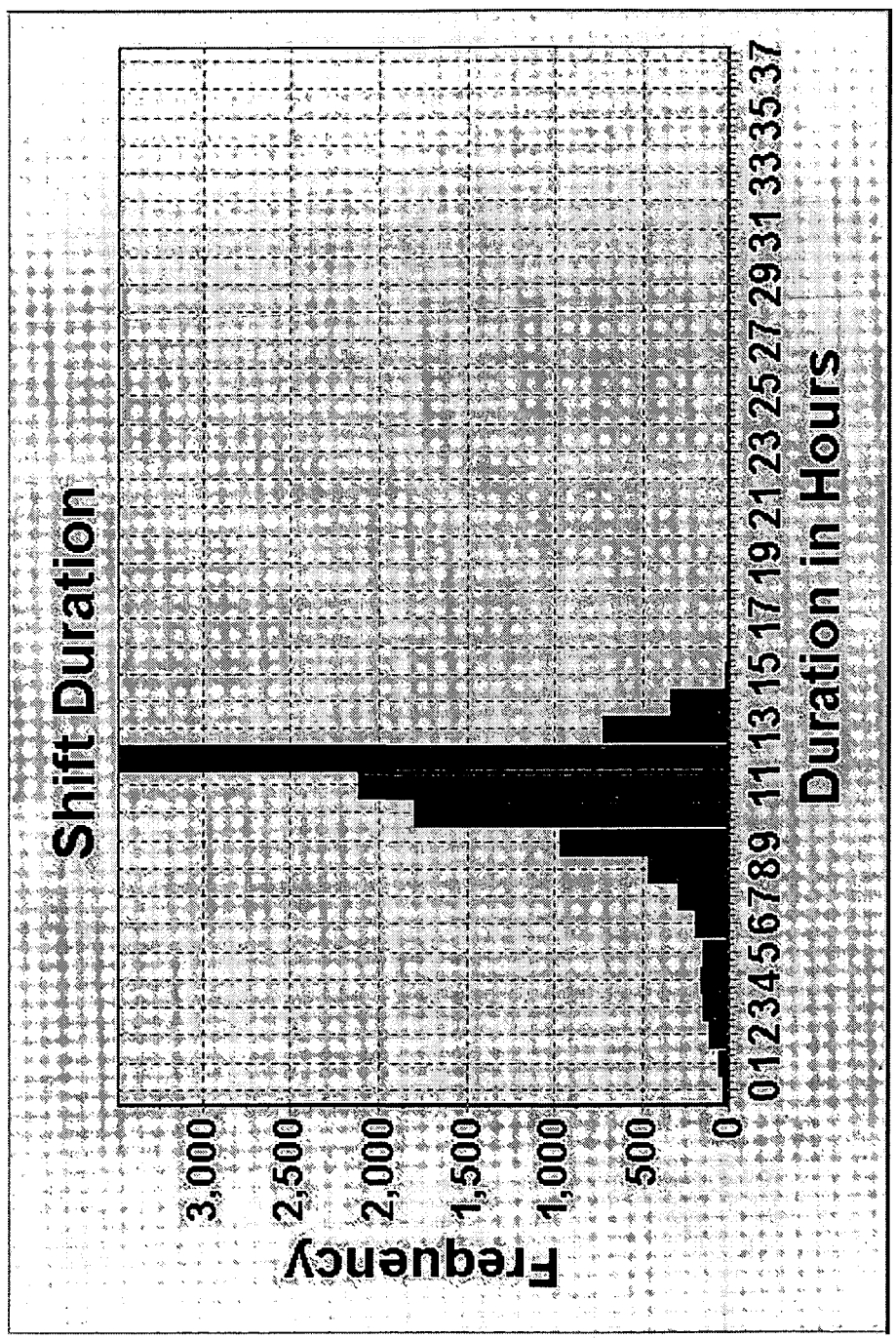
FIG. 27 contains a graph generated from a diagnostic report that shows the distribution of shift lengths, according to an embodiment of the present invention.
Figure 28:
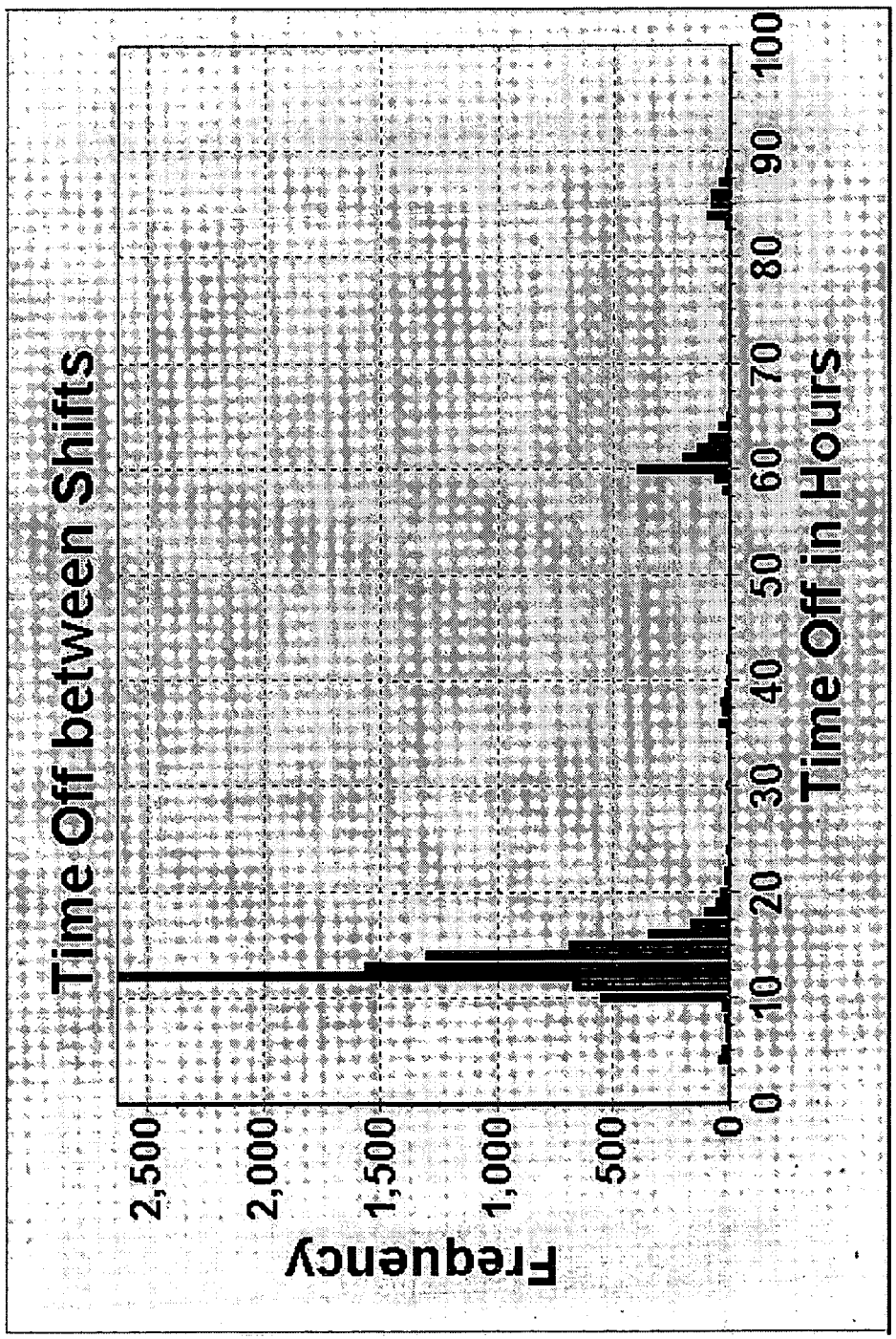
FIG. 28 contains a graph generated from a diagnostic report that shows the distribution of time off between successive shift times, according to an embodiment of the present invention.
Figure 29:
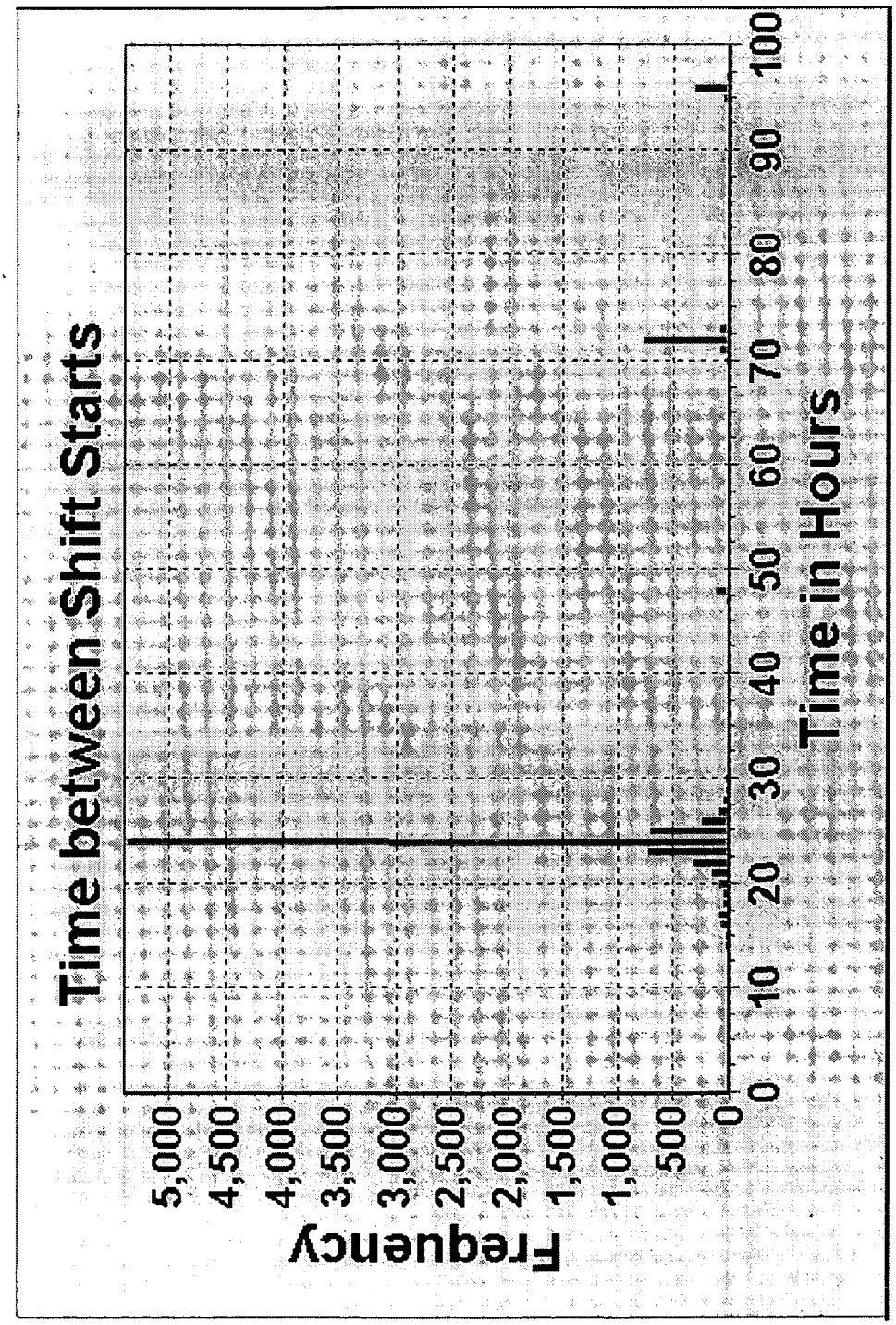
FIG. 29 contains a graph generated from a diagnostic report that shows the distribution of time between shift starts, according to an embodiment of the present invention.
Figure 30:
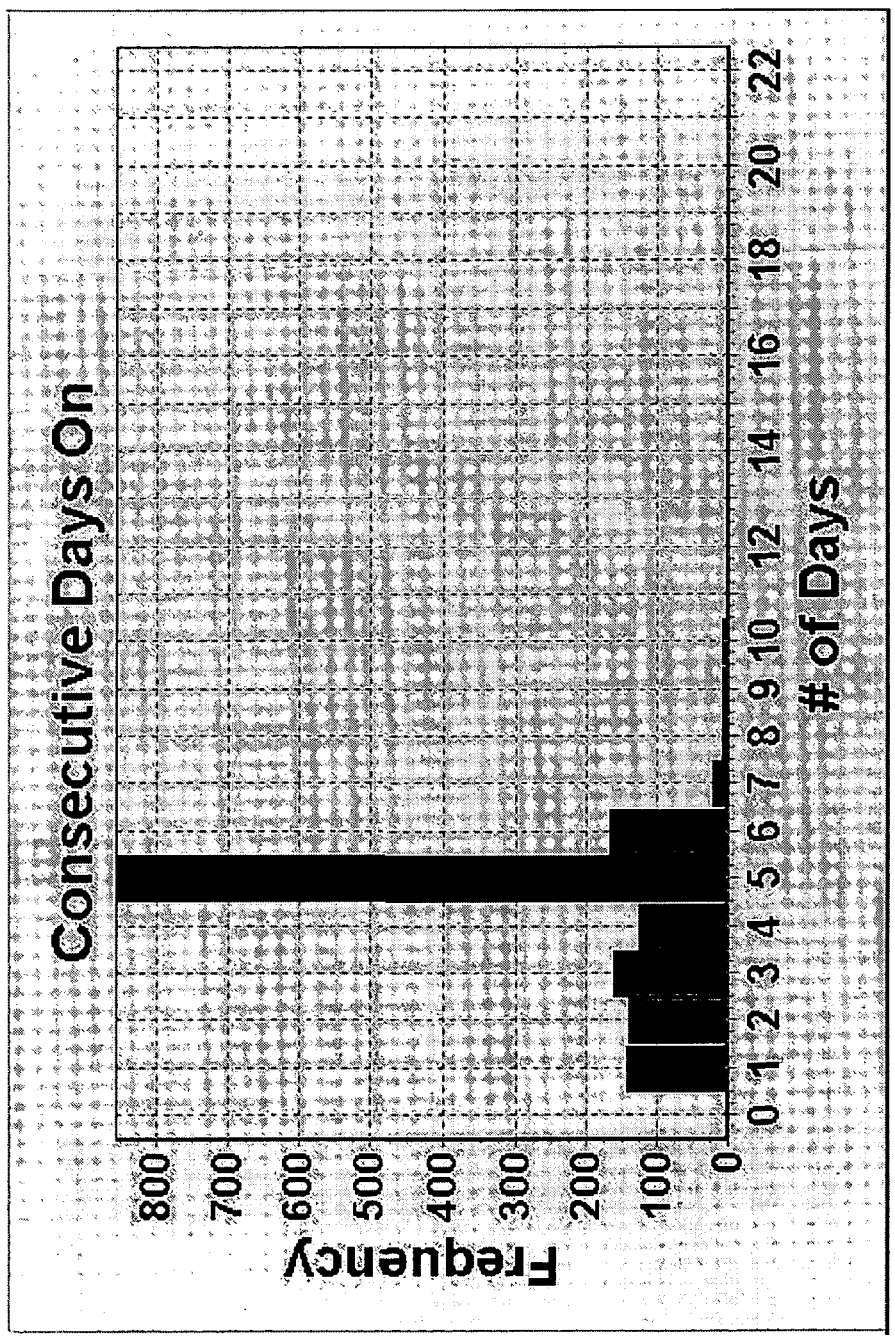
FIG. 30 contains a graph generated from a diagnostic report that shows the distribution of consecutive day work blocks, according to an embodiment of the present invention.
Figure 31:
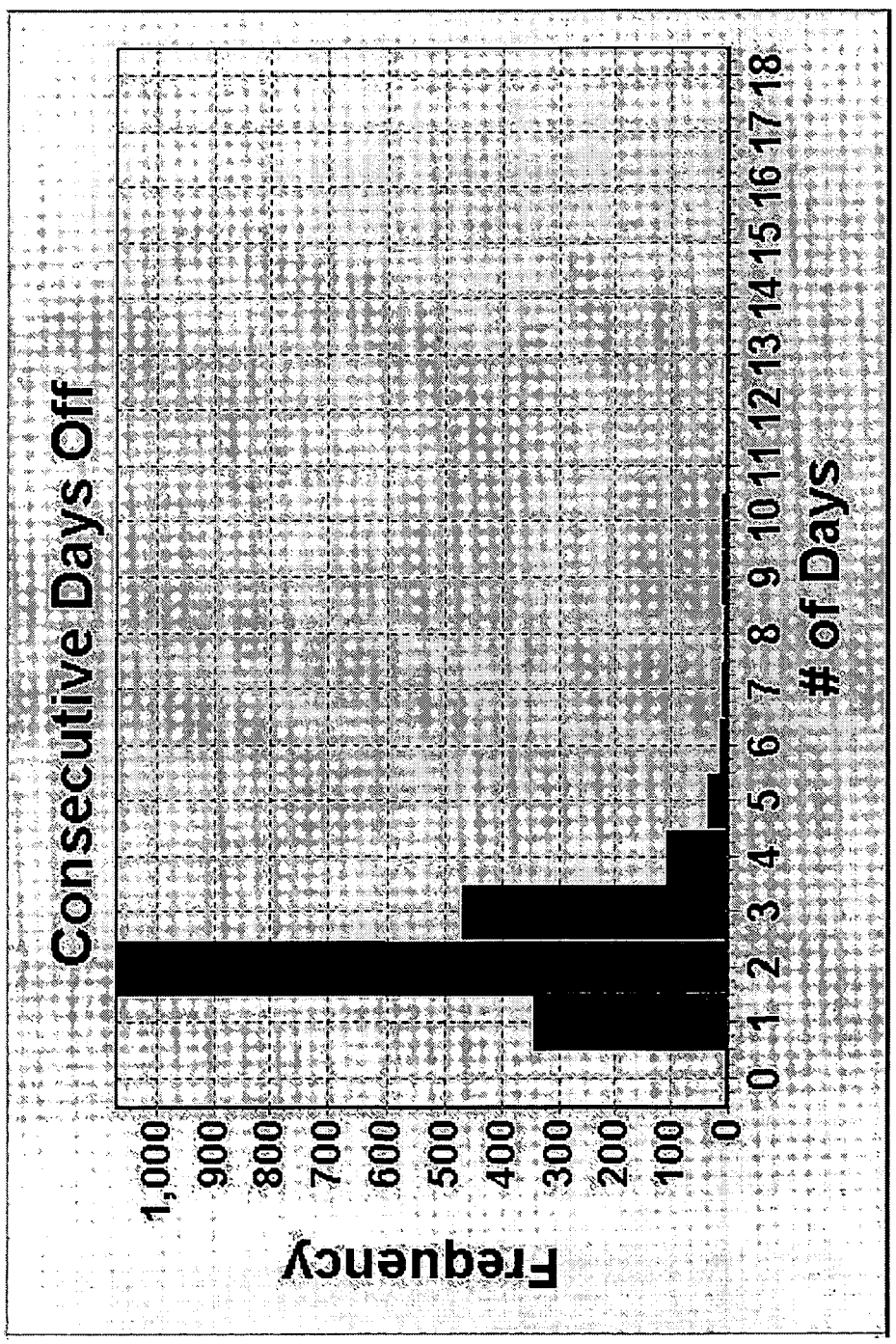
FIG. 31 contains a graph generated from a diagnostic report that shows the distribution of days off between work blocks, according to an embodiment of the present invention.
Figure 32:
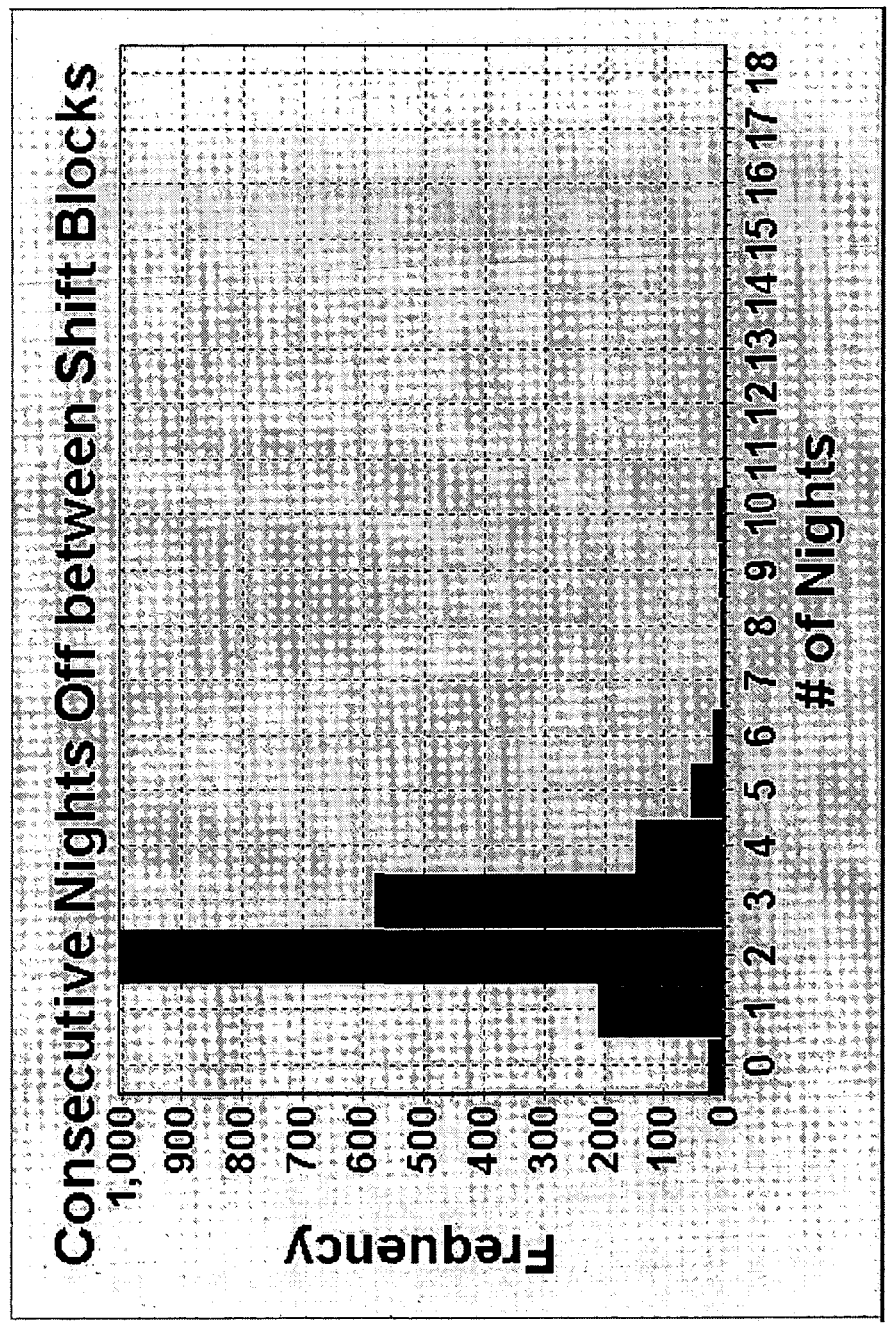
FIG. 32 contains a graph generated from a diagnostic report that shows the distribution of nights of between work blocks, according to an embodiment of the present invention.

In this manner, a different paradigm which uses Fatigue-Risk-Informed Safety-Performance-Based management of FSM rules can provide a viable alternative to current excessively prescriptive HoS rules for NSIR drivers by providing for 1. A revision of, or an exemption or waiver to HoS regulations for qualified trucking carriers to allow them to operate under FSM rules within a FRISPB program which permit the driver to adjust his sleep and nap schedule and driving schedule to minimize sleep deprivation fatigue risk, without being unnecessarily constrained by excessively prescriptive HoS rules.
2. Vehicles, for example CMVs, installed with telematics systems and a data capture process which provides for ongoing electronic monitoring to objectively confirm work-rest pattern and/or sleep data using telematics (GPS satellite, ECM uplink or other comparable Electronic On-Board Recorder (EOBR) system).
3. A special training program for NSIR drivers on circadian sleep and alertness physiology, flexible sleep management rules and maintaining good health on a NSIR driver lifestyle, with testing to establish their personal sleep personality, and subject matter testing to ensure they are qualified for the Flexible Sleep Management program.
4. Ongoing regular fatigue risk assessments of each driver using a scientifically-validated expert risk Fatigue Risk assessment system which has been validated in actual trucking operations and shown to reduce accidents and injuries, and regular (e.g. weekly or monthly) feedback of each driver's individual sleep deprivation Fatigue Risk score to him, his dispatchers and managers.
5. Management oversight procedures which hold each driver and his dispatchers and managers accountable for minimizing the Fatigue Risk score, and maintaining acceptable levels, including a process to provide a fatigue risk score to each driver and to his dispatchers and managers.
6. In addition to Fatigue Risk scores, drivers, their dispatchers and managers are provided with diagnostic reports and recommended interventions to aid them in reducing or maintaining fatigue risk scores at safe controlled levels. Examples of these diagnostic reports and corrective intervention reports are found in FIGS. 24-33. Specifically, FIG. 24 contains a diagnostic report generating a graph that shows how far drivers are deviating from the ideal 24-hour interval between successive daily times of starting to drive, according to an embodiment of the present invention. FIG. 25 contains a diagnostic report generating a graph that shows the time of day distribution of duty start times, according to an embodiment of the present invention. FIG. 26 contains a diagnostic report generating a graph that shows the time of day distribution of duty end times, according to an embodiment of the present invention. FIG. 27 contains a diagnostic report generating a graph that shows the distribution of shift lengths, according to an embodiment of the present invention. FIG. 28 contains a diagnostic report generating a graph that shows the distribution of time off between successive shift times, according to an embodiment of the present invention. FIG. 29 contains a diagnostic report generating a graph that shows the distribution of time between shift starts, according to an embodiment of the present invention. FIG. 30 contains a diagnostic report generating a graph that shows the distribution of consecutive day work blocks, according to an embodiment of the present invention. FIG. 31 contains a diagnostic report generating a graph that shows the distribution of days off between work blocks, according to an embodiment of the present invention. FIG. 32 contains a diagnostic report generating a graph that shows the distribution of nights of between work blocks, according to an embodiment of the present invention. FIG. 33 contains an output comprising a diagnostic assessment and a corrective report including supervisory interventions, according to an embodiment of the present invention.

7. In this manner, drivers, dispatchers and managers are "Fatigue-Risk Informed," and this "Fatigue-Risk Informed" process gives regular (e.g. daily, weekly or monthly) feedback of each driver's individual Fatigue Risk score, the diagnoses of the causation of any high fatigue flags and recommended specific interventions for him, his dispatchers and managers to correct the fatigue risk levels.

8. A "Safety-Performance-Based" system which evaluates on an ongoing basis each driver's success at managing his fatigue risk score using the diagnostic reports and recommended corrective interventions, and an ongoing commitment by the qualified trucking carrier to maintain a continuous improvement process that seeks to control sleep-deprivation related fatigue risk.

FRISPB Methods and Systems Provide Equivalent or Greater Safety

The FRISPB Flexible Sleep Management (FSM) program provides equivalent or greater safety because of the multiple additional components of safety management that are provided by FRISPB as compared to the current HoS regulations.

The safety equivalency or greater safety of FRISPB can be assessed by considering each of the six components of the FRISPB program by themselves because they would offer some benefit even if each was employed in isolation. But implementing all six components as complementary pieces of a broader strategy offers the maximum benefit and the greatest likelihood of redefining our outlook on acceptable accident risk in trucking operations. The beneficial effect of the group of components operating together in a FRISPB system we expect to be greater than the sum of its parts.

The Safety Benefits of Each Component of the FRISPB Safety Management System

1. CMVs installed with telematics systems and a data capture process which provides for ongoing electronic monitoring to objectively confirm work-rest pattern and/or sleep data using telematics (GPS satellite, ECM uplink or other comparable EOBR system). HoS regulatory requirements are exceeded because objective verification of work-rest patterns and/or sleep data using EOBRs or their telematics equivalent are a built-in part of the FRISPB process. Instead of relying on paper logs with their questionable reliability, the drivers' work-rest pattern and/or sleep data will be recorded electronically, and hence the times of day when the driver could not be sleeping will be verified. The risk of sleep deprivation with its safety and health risks is thereby reduced.

2. A special training program for NSIR drivers on circadian sleep and alertness physiology, flexible sleep management rules and maintaining good health on a NSIR driver lifestyle, with testing to establish their personal sleep personality, and subject matter testing to ensure they are qualified for the Flexible Sleep Management program. HoS regulatory requirements are exceeded by FRISPB management because there are considerable benefits to providing sleep management and alertness training to truck drivers. This is not required by current HoS regulations. Most drivers will be eager to learn techniques for making them less fatigued on the road while simultaneously increasing their efficiency within the FRISPB framework. While these training sessions offer far too many strategies and suggestions to enumerate here, some of the basics of fatigue management that will be particularly useful include:

Learning the importance of anchor sleep and managing a schedule so that the driver can expect some number of hours of sleep at a certain time of day or night. While the current HoS regulations were intended to force drivers onto 24-hour schedules compatible with circadian physiology, there are numerous ways drivers can fall off of these schedules and many do not understand the importance of attempting to maintain a relatively constant schedule.

Limiting attempts to sleep at points of the circadian phase that make sleep difficult. Drivers are helped by understanding when in the course of the day they can expect their bodies to obtain restorative anchor sleep and when they should attempt to limit sleep to shorter naps.

Avoiding going on duty after having been awake for extended period of time. One common source of fatigue is seen in the driver who has a day off work and then begins his duty period late in the evening. This means that by the time they finish their route the following morning, they have been awake for approximately 24 hours. In the NSIR training program, drivers will learn to adjust to different duty start times and plan sleep accordingly, so that they do not wind up awake for extended periods prior to getting behind the wheel.

3. Ongoing Fatigue Risk assessments of each driver using a scientifically-validated expert risk Fatigue Risk assessment system which has been validated in actual trucking operations and shown to reduce accidents and injuries. HoS regulatory requirements are exceeded by FRISPB because every driver is objectively assessed for Fatigue Risk on an ongoing basis. Other than compliance with HoS regulations, which is not well correlated with fatigue risk as discussed above, the current HoS regulations provide no ongoing assessment of sleep deprivation in the individual driver.

4. A "Fatigue-Risk-Informed" process which gives regular (e.g. weekly or monthly) feedback of each driver's individual fatigue risk score to him, his dispatchers and managers, also provides diagnostic reports and corrective intervention suggestions. HoS regulatory requirements are exceeded by the FRISPB because there are considerable benefits in giving drivers feedback in the form of a fatigue risk score on how well they are doing to manage sleep and fatigue. Not only are they kept continually aware of the importance of the issue, but they can learn what patterns of driving and rest contribute to better or worse sleep management, and fatigue reduction and improved health.

5. A "Safety-Performance-Based" system which evaluates on an ongoing basis each driver's success at managing his fatigue risk score, and an ongoing commitment by the qualified truckload carrier to maintain a continuous improvement process that seeks to control sleep-deprivation related fatigue risk. HoS regulatory requirements are exceeded by the FRISPB because every driver is not only objectively assessed for Fatigue Risk, but is also held accountable for optimizing his sleep, reducing fatigue and thereby improving his health. Furthermore HoS regulatory requirements are exceeded by FRISPB because qualified participating companies adopt a continuous risk data-driven improvement process to improve driver safety and health. There is no formal requirement for this under current HoS regulations.

In sum, not only does the FRISPB system described herein contribute to improved driver safety and health, but the combined effects of these working together is likely to have a safety and health benefit that is greater than the sum of the parts.

Fatigue Risk Assessment System

The fatigue risk assessment system of the present invention applies the Fatigue-Risk-Informed Safety-Performance-Based (FRISPB) paradigm described herein. As such, the fatigue risk assessment system of the present invention can apply one or more risk models to measure actual fatigue risk. In a preferred embodiment, a risk model can be implemented as an expert system, for example, the Circadian Alertness Simulator (CAS) expert system described herein. Additional examples are the Three-Process Model of Alertness, See Akerstedt T. Folkard S. and Portin, C. "Predictions from the three process model of alertness," Aviat. Space Environ Med 2004 75 (3 Suppl): A75-83)" incorporated herein in its entirety by reference; the Sleep Activity Fatigue and Task Effectiveness (SAFTE) Model, See Hursch S R et al. "Fatigue Models for Applied Research in Warfighting," Aviat. Space Environ Med 2004 75 (3 Suppl): A44-53 incorporated herein in its entirety by reference, and the Fatigue Audit InterDyne (FAID) model See Roach G D, Fletcher A, and Dawson, D, "A model to Predict Work-Related Fatigue Based on Hours of Work," Aviat. Space Environ Med 2004 75 (3 Suppl): A61-69 incorporated herein in its entirety by reference.

Figure 34:
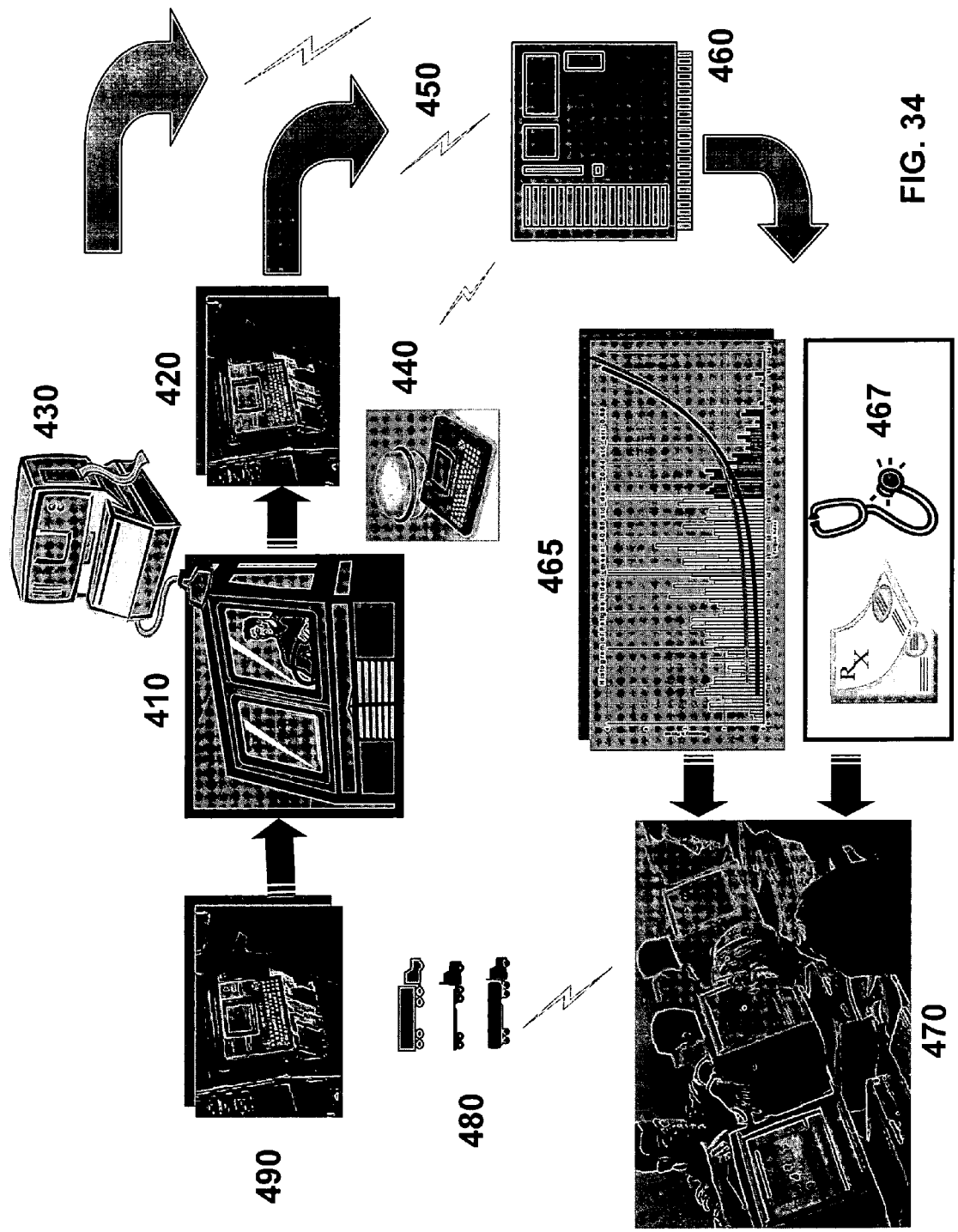
FIG. 34 contains a system level diagram of a fatigue risk assessment system, according to an embodiment of the present invention.

FIG. 34 contains a system level diagram of a fatigue risk assessment system 100, according to an embodiment of the present invention. The fatigue risk assessment system 400 comprises a driver in his truck cab 410, a work-rest pattern input device 420, and optionally a sleep data input device 430, and optionally a position verification device 440, a data transmission system from the vehicle to a central data processing center 450, a data aggregation and processing platform 460, a computed fatigue risk score for each driver 465, a optional diagnostic report on the causation of the drivers fatigue and intervention recommendations or intervention plan 467, an output display on dispatcher screens 470, a data transmissions system from the dispatch center to the truck cab 480, and a display of the individual driver's fatigue risk score and instructions on intervention recommendations to reduce fatigue risk on his truck cab monitor 490.

In one embodiment, the input devices 420 and 430, position verification device 440, data aggregation and processing platform 460, and output display 470 are separate from each other, and communicate with each other through a communications network 450 and 480. The fatigue risk assessment system 400 can be embedded in one or more devices that can be operated independently or together in a networked environment, where the network can include, for example, the communication networks 450 and 480. The communications networks 450 and 480 can be a satellite communications network, a wireless network, a telecommunications network, or a data communications network, such as a Local Area Network (LAN) or a wide area network (WAN), or a combination thereof.

One or more input devices 420, 430 receive current work-rest pattern data and/or sleep data from one or more individuals, respectively. In an embodiment, input devices 420, 430 generate a current record from the current work-rest pattern and/or sleep data. The current work-rest pattern and/or sleep data includes data that enables the data aggregation and processing platform 460 to generate at least one of a fatigue assessment result 465, a diagnostic report, and a recommended intervention plan 467 to reduce fatigue risk. In an embodiment, the data comprises actual work and rest hours of the driver during a pre-defined period, such as a 24-hour period, manually entered by the driver, for example, on an in-cab keyboard of the input device 420 or 430. The input data can further comprise additional data such as vehicle and/or individual location data. Additional data may be input into the input device 420, 430 and position verification device 440, depending on the risk model or models that are implemented by the data aggregation and processing platform. For example, additional parameters such as minimum required work hours, and maximum work hours may also input into the input device 420, and actual sleep time, may also input into the input device 420 or 430.

In one embodiment, each individual is a commercial motor vehicle (CMV) operator or machine operator, for example, a truck driver, bus driver, airline pilot or navigator, or boat operator, or any driver or machine operator who poses a safety risk as a result of being deprived of sleep while operating a machine or commercial motor vehicle (CMV) such as a truck, bus, or train, or other mode of transportation such as an airplane or boat. In another embodiment, the individual is an employee who performs a function, wherein a risk of fatigue can affect the employee's ability to effectively perform the function.

The input devices 420, 430, and 440 can be a telephone, cell phone, computer, data recorder, physiological sensor, telematics data entry screen, personal digital assistant (PDA), or other device that can interface with the data aggregation and processing platform. For example, the individual can enter the current work pattern into the input device 420 or sleep data into the input device 430 via a keyboard and display In one embodiment, the input device is a Qualcomm input device that interfaces with the data aggregation and processing platform from a commercially available Qualcomm system and communication network. In another embodiment it is a Cadec or a Geologics system or any other commercial system which transmits data and messages to and from the truck by remote communications including satellite communications, telecommunications, cell phone networks etc etc. Alternatively, the individual can radio or call a dispatcher or a manager, or fax or email a text message to the dispatcher or manager, whereby current work-rest pattern and/or sleep data can be entered in this manner by the dispatcher or manager.

In one embodiment, the current work pattern and sleep data is received from logs, for example, driver logs, pilot logs, and marine logs, and manually entered by the individual into the input device 10. In another embodiment, the current work-rest pattern and/or sleep data is retrieved electronically, for example, from a database. In another embodiment, the current work-rest pattern and/or sleep data is captured using a telematics system. In this embodiment, a CMV is installed with the telematics system which provides ongoing electronic monitoring to objectively confirm Hours of Rest data using telematics. The telematics system can be a system used in CMVs that combines wireless communication with GPS tracking. In another embodiment, the telematics system comprises at least one of Electronic Onboard Recorders, GPS systems, and electronic control modules (ECM), whereby data on vehicle use can be downloaded to the position verification device 440. In this manner, when a telematics is used, the data can further be verified, for example, to confirm that the vehicle did not move after the driver entered data indicating that she was resting or sleeping. Other methods may also be used, including fully automated processes that detect if a truck is moving or has stopped for more than a brief period of time, or sensors in the cab seat or sleeper berth of the truck.

For example, many trucks have an automated messaging system using Qualcomm, GeoLogics, or other product that permits a driver to enter text messages or macros on a screen in the vehicle. In one example, a driver can enter a time-stamped macro indicating that she is going on-duty, or going off-duty.

The position verification device 440 verifies the current work-rest pattern and/or sleep data that is entered into the input device 420 or 430 by detecting vehicle movements that could only occur if the driver was awake and operating the vehicle permits electronic monitoring to objectively verify the accuracy of the current work-rest pattern and/or sleep data entered by the individual to the input device 420 or 430. In one embodiment, the position verification device 440 comprises a telematics system that verifies hours that the commercial motor vehicle (CMV) is driven and at rest. In one embodiment, the position verification device 440 is collocated with the input device 420 and/or 430 in a commercial motor vehicle or machine. In another embodiment, the input device 420 and 430 and the position verification device 440 are the same, wherein verified data is output to the data aggregation and processing platform.

The data aggregation and processing platform 460 receives the current record containing the work-rest pattern and/or sleep data from the input devices 420 and/or 430. In one embodiment, the data aggregation and processing platform 460 receives current records, each record comprising work-rest pattern and/or sleep data relating to an individual, from a plurality of input devices. In another embodiment, data aggregation and processing platform 460 receives current work-rest pattern and/or sleep data from the input devices 420 and/or 430 and verifies it by comparing it with data from the position verification and/or vehicle movement detection device 440.

In one embodiment, the database stores current records generated by either input device 420, 430. In this manner, each current record of a given individual is aggregated in the database with previously collected records related to the individual.

In one embodiment, the data aggregation and processing platform is located at a central processing center. In another embodiment, the data aggregation and processing platform is co-located with the input device. In this manner, the input device and the data aggregation and processing system can comprise a mobile unit that is installed in a vehicle or in a stationary location, such as a home or office. In addition, the mobile unit can comprise the output display and the position verification device.

The data aggregation and processing platform 460 further comprises a fatigue risk processor that computes the fatigue assessment result from the current work-rest pattern and/or sleep data, and records and previously collected records. The fatigue risk processor computes the fatigue assessment result according to least one predictive model. In one embodiment, the fatigue risk processor comprises the Circadian Alertness Simulator (CAS) described herein, wherein the CAS is adapted to measure the risk of accidents caused by sleep deprivation in commercial truck drivers. The CAS includes a software-based expert system that offers a tool for managing a set of flexible sleep management rules for safe operation of trucking fleets, the flexible rules conforming with the FRISPB paradigm described herein. In one embodiment, the CAS expert fatigue risk software program is based on a risk model described herein with regard to the abovementioned U.S. Pat. No. 5,433,223, issued Jul. 18, 1995, entitled "Method for Predicting Alertness and Bio-Compatibility of Work Schedule of an Individual."

The predictive model can be a fatigue risk model and a driver profile model, or any model that predicts a rate of performance failures or accident rates. In one embodiment, the fatigue risk model computes the fatigue assessment result as a fatigue risk score, and may also generate for example, statistical data such as the probability of a driver having an accident. In another embodiment, the driver profile model computes a risk assessment result as a driver profile result, which provides additional value in predicting when drivers may have accidents. A driver risk processor can execute one or more processes to generate both the fatigue assessment result and driver profile result, which can be used by the individual, her dispatchers and her safety managers to provide regular feedback, for example, daily weekly or monthly, of each fatigue risk score and the driver profile score.

The driver profile model computes a driver profile result to predict a rate of performance failures or accident rates, for example, a probability of a driver or a group of drivers having an accident. The driver profile result is derived from factors other than fatigue-related factors, but may also contribute to risk, also referred to as non-fatigue causes of risk. Such non-fatigue causes of risk may include age, experience, and motor vehicle accident history. The driver profile result can likewise be output to the driver, his dispatcher, and managers responsible for safety via at least one output display in a user-readable format. In one embodiment, the driver profile result can be output to the same output display as the abovementioned fatigue risk scores.

The fatigue risk score and the driver profile result can be presented to managers, dispatchers, and/or the drivers so that the drivers can adjust their work-rest patterns in response to the fatigue assessment result in order to reduce their fatigue assessment result. For example, drivers can be trained to minimize their fatigue risk scores and to maximize utilization by modifying their work-rest schedules so that they get restorative rest, and reduce fatigue or accident risk. In addition, drivers, dispatchers, and managers can minimize fatigue risk scores by making decisions regarding duration of on-duty time, duty start time, night or day driving preferences, on-duty duration, and consecutive days off duty. This can be achieved by ongoing monitoring of risk for individual drivers, groups of drivers, or across an organization, and tracking and reporting of overall statistics related to fatigue risk. In addition, employers can maximize the efficient deployment of its drivers, while increasing customer satisfaction by using the data to determine customer delivery schedules, equipment availability, and driver availability.

The fatigue assessment result can be accumulated in the data aggregation and processing platform 460, and derived from the actual schedule of work and rest hours of an individual or group of individuals over a predefined period of time. This can be used to compute a cumulative fatigue risk score that can then be used to reliably predict truck and other transportation accident risk.

In one embodiment, the display output is a fleet management screen 470, by which a dispatcher or a manager can monitor fatigue risk in a fleet of drivers. In another embodiment, a fatigue risk score for each driver in the fleet is provided to the driver, his dispatcher and those operations and safety managers who make informed decisions based on the received fatigue risk score. In another embodiment, the output display comprises a computer having a computer program that outputs the fatigue assessment result in a user-readable format. In one embodiment, the output display is the same as the abovementioned input device. In this manner, a driver can enter current work-rest pattern and/or sleep data into the input device, and also receive a fatigue assessment result, for example, a fatigue risk score result.

Figure 35:
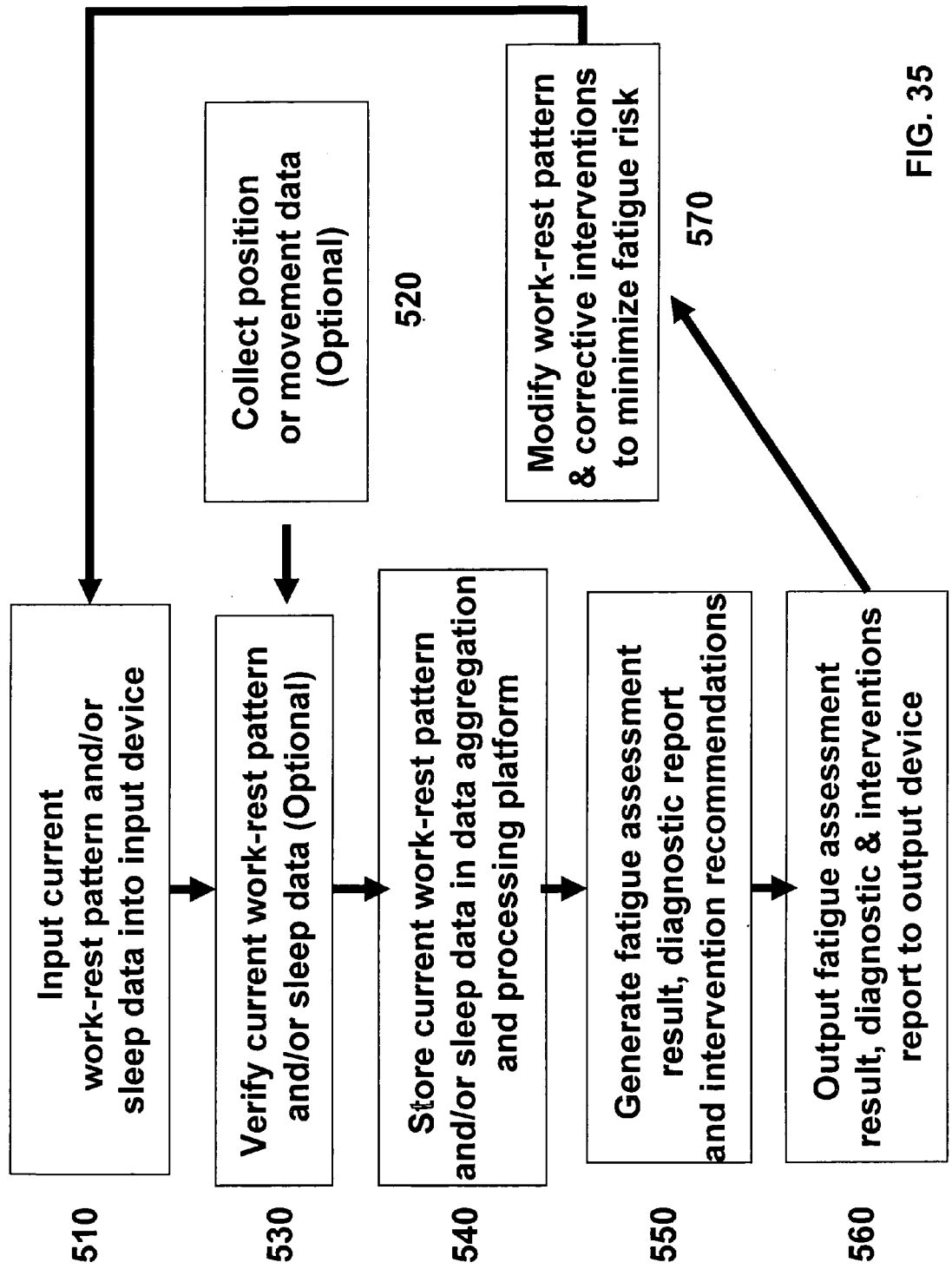
FIG. 35 contains a flowchart of the steps used to assess fatigue and to modify fatigue risk according to an embodiment of the present invention.

FIG. 35 contains a flowchart of the steps used to assess fatigue and to reduce fatigue risk according to an embodiment of the present invention. First, as shown in step 510, current work-rest pattern and/or sleep data is input into an input device. Optionally, as shown in step 520, position or movement data is collected which provides an option to verify the current work-rest pattern and/or sleep data as shown in step 530. Next, as shown in step 540, the current work-rest pattern and/or sleep data is stored in a data aggregation and processing platform. Next, as shown in step 550, a fatigue assessment result is generated together with a diagnostic report on the contributing causes to the driver fatigue as well as a set of recommended interventions. Next, as shown in step 560, the fatigue assessment result, diagnostic report and intervention recommendations are outputted to an output device. Next, as shown in step 570, the work-rest pattern is modified in an attempt to minimize fatigue risk. The results are then confirmed in steps 510, 520, 530, 540, 550 and 560, whereby the cycle comprising steps 510-570 is repeated in a continuous Fatigue-Risk-Informed Safety-Performance-Based (FRISPB) process While this invention has been particularly shown and described with references to preferred embodiments thereof, it will be understood to those skilled in the art that various changes in form and details may be made herein without departing from the spirit and scope of the invention as defined in the appended claims.

What is claimed is:

1. A method for assessing fatigue risk of an individual, the method comprising:
   receiving at least one of current work-rest pattern and sleep data of an individual;
   combining the at least one of the current work-rest pattern and the sleep data with previous data related to the individual;
   generating a fatigue risk assessment result from the combination of the at least one of the current work-rest pattern and the sleep data and previous data related to the individuals;
   generating a diagnostic assessment report on the causation of any excessive fatigue risk;
   generating a corrective intervention plan for reducing excessive fatigue risk of the individual based on at least one of the fatigue risk assessment result and the diagnostic assessment report; and
   outputting at least one of the fatigue risk assessment result, the diagnostic assessment report, and the corrective intervention plan in a user-readable format to a user.

2. The method of claim 1 further comprising:
   generating a current record from the at least one of the current work-rest pattern and the sleep data related to the individual; and
   storing the current record.

3. The method of claim 1, wherein the at least one of the current work-rest pattern and the sleep data is received of a group of individuals, and wherein the fatigue risk assessment result is generated for each individual.

4. The method of claim 1 further comprising verifying the at least one of the current work-rest pattern and the sleep data.

5. The method of claim 1 further comprising transmitting the at least one of the current work-rest pattern and the sleep data through a communications network.

6. The method of claim 5, wherein the communications network is one of a satellite communications network, a wireless network, a telecommunications network, and a data communications network.

7. The method of claim 1 further comprising applying at least one predictive model to compute the fatigue risk assessment result, the diagnostic assessment report, and the corrective intervention plan.

8. The method of claim 7, wherein the predictive model complies with a Fatigue-Risk-Informed Safety-Performance-Based (FRISPB) paradigm.

9. The method of claim 7 further comprising at least one of computing the fatigue risk assessment result as a fatigue risk score and computing a non-fatigue factor assessment result as a driver profile result.

10. The method of claim 9 further comprising generating a driver risk assessment from a combination of the fatigue risk score and the driver profile result.

11. The method of claim 1 comprising using the fatigue risk assessment result to control fatigue risk in the individual.

12. The method of claim 1 comprising combining at least one of the fatigue risk assessment result, the diagnostic assessment report, and the corrective intervention plan to reduce future fatigue risk.

13. The method of claim 1, wherein the individual is at least one of a machine operator and a driver.

14. The method of claim 1, wherein generating the diagnostic assessment report comprises generating a graph that identifies how far the individual is deviating from an ideal 24-hour interval between successive daily times of starting to drive a vehicle.

15. The method of claim 1, wherein generating the diagnostic assessment report comprises generating a graph that illustrates a distribution of duty start times according to time of day.

16. The method of claim 1, wherein generating the diagnostic assessment report comprises generating a graph that illustrates a distribution of duty end times according to time of day.

17. The method of claim 1, wherein generating the diagnostic assessment report comprises generating a graph that illustrates a distribution of shift lengths of the individual according to duration.

18. The method of claim 1, wherein generating the diagnostic assessment report comprises generating a graph that illustrates a distribution of time off between successive shifts of the individual according to time off.

19. The method of claim 1, wherein generating the diagnostic assessment report comprises generating a graph that illustrates a distribution of time between successive shift starts of the individual.

20. The method of claim 1, wherein generating the diagnostic assessment report comprises generating a graph that illustrates a distribution of consecutive days on for the individual.

21. The method of claim 1, wherein generating the diagnostic assessment report comprises generating a graph that illustrates a distribution of consecutive days off for the individual.

22. The method of claim 1, wherein generating the diagnostic assessment report comprises generating a graph that illustrates a distribution of consecutive nights off between shift blocks for the individual.

23. The method of claim 1, wherein generating the corrective intervention plan comprises generating at least one immediate action for reducing any excessive fatigue risk of the individual.

24. The method of claim 23 herein the at least one immediate action directs the individual to take a nap.

25. The method of claim 23 wherein the at least one immediate action directs the individual to reduce the individual's duty length.

26. The method of claim 23 wherein the at least one immediate action directs the individual to consolidate their sleep schedule.

27. The method of claim 23 wherein the at least one immediate action directs the individual to take a day off.

28. The method of claim 23 wherein the at least one immediate action directs the individual to stabilize their duty start times.

29. The method of claim 1, wherein generating the corrective intervention plan comprises generating at least one diagnostic flag that indicates the causation of any excessive fatigue risk.

30. The method of claim 29, wherein the at least one diagnostic flag is generated in response to the diagnostic assessment report.

* * * * *